(12) United States Patent  (10) Patent No.: US 8,101,764 B2
Amegadzie et al.  (45) Date of Patent: Jan. 24, 2012

(54) MCH RECEPTOR ANTAGONISTS

(75) Inventors: Albert Kudzovi Amegadzie, Moorpark, CA (US); Yen Dao, Indianapolis, IN (US); Kevin Matthew Gardinier, Fishers, IN (US); David Joseph Garmene, Indianapolis, IN (US); Steven James Green, Indianapolis, IN (US); Erik James Hembre, Indianapolis, IN (US); Jianliang Lu, Fishers, IN (US); Patrick Gianpietro Spinazze, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 392 days.

(21) Appl. No.: 12/296,557

(22) PCT Filed: Jun. 8, 2007

(86) PCT No.: PCT/US2007/070668
§ 371 (c)(1), (2), (4) Date: Aug. 13, 2009

(87) PCT Pub. No.: WO2007/146759
PCT Pub. Date: Dec. 21, 2007

(65) Prior Publication Data
US 2010/0016350 A1  Jan. 21, 2010

Related U.S. Application Data

(60) Provisional application No. 60/811,838, filed on Jun. 8, 2006.

(51) Int. Cl.
C07D 513/02 (2006.01)
(52) U.S. Cl. ........................................ 546/114
(58) Field of Classification Search .................. 546/114
See application file for complete search history.

(56) References Cited

FOREIGN PATENT DOCUMENTS
| | | |
|---|---|---|
| WO | WO 03/033476 | 4/2003 |
| WO | WO 2005/047293 | 5/2005 |
| WO | WO 2007/093364 | 8/2007 |

OTHER PUBLICATIONS

Dyck et al., Journal of Medicinal Chemistry, 2005, 49,(13), 3753-3756.*

Dyck, et al., "A Thienopyridazinone-Based Melanin-Concentrating Hormone Receptor 1 Antagonist with Potent in Vivo Anorectic Properties," Journal of Medicinal Chemistry, American Chemical Society, vol. 49, No. 13, pp. 3753-3756 (2006).

* cited by examiner

Primary Examiner — Nizal Chandrakumar
(74) Attorney, Agent, or Firm — Elizabeth Dingess-Hammond

(57) ABSTRACT

The present invention relates to a melanin concentrating hormone antagonist compound of formula (I): wherein $R^1$, $R^a$, $R^b$, $R^2$, $L^1$, $R^3$, $R^4$ and $R^5$ are as defined, or a pharmaceutically acceptable salt, enantiomer, diastereomer or mixture of diastereomers thereof useful in the treatment, obesity and related diseases.

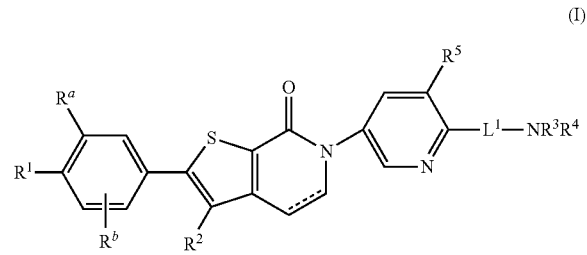

(I)

14 Claims, No Drawings

SEQUENCE LISTING

<160> NUMBER OF SEQ ID NOS: 2

<210> SEQ ID NO 1
<211> LENGTH: 28
<212> TYPE: DNA
<213> ORGANISM: artificial
<220> FEATURE:
<223> OTHER INFORMATION: synthetic

<400> SEQUENCE: 1
gccaccatgg acctggaagc ctcgctgc                                          28

<210> SEQ ID NO 2

```
<211> LENGTH: 24
<212> TYPE: DNA
<213> ORGANISM: artificial
<220> FEATURE:
<223> OTHER INFORMATION: synthetic

<400> SEQUENCE: 2
tggtgccctg acttggaggt gtgc                                          24
```

MCH RECEPTOR ANTAGONISTS

This application claims the benefit of U.S. Provisional Application Ser. No. 60/811,838, filed 8 Jun. 2006 and PCT Application Serial No. PCT/US2007/070668, filed 8 Jun. 2007, each hereby incorporated by reference in their entirety.

FIELD OF INVENTION

The present invention is in the field of medicine, particularly in the field of treating obesity and related diseases.

BACKGROUND OF THE INVENTION

Melanin concentrating hormone (MCH) is a 19 amino acid neuropeptide produced in the lateral hypothalamic area and zona incerta. Extensive evidence supports the orexigenic activity of MCH. MCHR1$^{-/-}$ mice have been reported to be lean and hyper metabolic, indicating that the R1 isoform mediates at least some of the metabolic effects of MCH.

PCT International publication WO 03/033476 A1 discloses pyrimidinones as melanin concentrating hormone receptor antagonists. PCT international publications WO2005/047293 A1 discloses compounds said to be useful as MCH antagonists. Dyck, B et al (*Journal of Medicinal Chemistry* (2006) 49(13) 3753-3756) entitled "*A Thienopyridazinone-Based Melanin-Concentrating Hormone Receptor 1 Antagonist with Potent In Vivo Anorectic Properties*" discloses thienopyridazinone compounds said to be useful as MCH antagonists.

There is a need for potent, selective and therapeutically effective agents to better control dietary habits, minimize the preponderance of obesity, treat, and/or ameliorate the effects of obesity and Related Diseases. The present invention provides particularly preferred compounds having high potency, selectivity and/or in-vivo efficacy as MCH antagonists useful for the treatment of obesity and related diseases.

SUMMARY OF THE INVENTION

The present invention relates to a compound of formula I:

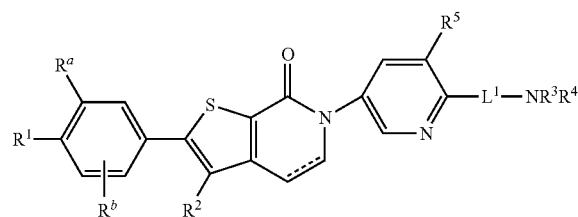

I wherein:
"-----" is optionally a bond to form a double bond;
$R^1$ is independently selected from the group consisting of hydrogen, $C_1$-$C_4$ alkyl, halo, $C_1$-$C_4$ haloalkyl, $C_1$-$C_4$ alkoxy, $C_1$-$C_4$ haloalkoxy, and —O—$C_3$-$C_4$ cycloalkyl;
$R^a$ and $R^b$ are independently hydrogen, fluoro, chloro, or methoxy;
$R^2$ is hydrogen or methyl;
$L^1$ is selected from the group consisting of a bond, —OCH$_2$CH$_2$—, —OCH$_2$CH$_2$CH$_2$—, —C(O)NCH$_2$CH$_2$—, —C(O)CH$_2$CH$_2$—, NHCO)CH$_2$CH$_2$—, and —NHC(O)CH$_2$CH$_2$—; —NHC(O)CH$_2$CH$_2$CH$_2$—, and —C(O)NHCH$_2$CH$_2$CH$_2$—

$R^3$ and $R^4$ combine together with the nitrogen atom to which they are attached to form an optionally substituted 4 to 7-member heterocyclic ring; or one of $R^3$ and $R^4$ combines with $L^1$ at a position α, β, γ, or, δ to the nitrogen of $NR^3R^4$ to form a nitrogen containing 4 to 7-member heterocyclic ring with $L^1$; wherein each 4 to 7 member nitrogen containing heterocyclic ring formed by $R^3$ and $R^4$ or $L^1$ and either of $R^3$ and $R^4$ is optionally substituted with one or two groups independently selected from the group consisting of oxo, hydroxy, —OR$^6$, $C_1$-$C_4$ alkyl, halo, $C_1$-$C_4$ haloalkyl, —$C_1$-$C_3$ alkylalcohol, —C(O)$C_1$-$C_3$ alkyl, $C_3$-$C_6$ cycloalkyl, $NR^6R^{6'}$, and $C_1$-$C_4$ alkyl$NR^6R^{6'}$;
$R^5$ is hydrogen, halo, cyano, methyl, and methoxy;
$R^6$ and $R^{6'}$ are independently selected from the group consisting of hydrogen, $C_1$-$C_4$ alkyl, —$C_1$-$C_3$ alkylalcohol, —$C_1$-$C_3$ haloalkyl, and $C_3$-$C_4$ cycloalkyl, or $R^6$ and $R^{6'}$ combine together with the nitrogen atom to which they are attached to form a 4 to 6 member nitrogen containing heterocyclic ring optionally substituted with a group selected from halo, $C_1$-$C_2$ alkyl, and hydroxy;
or a pharmaceutically acceptable salt, or enantiomer, diastereomer or mixture of diastereomers thereof.

The present invention also relates to a compound of formula

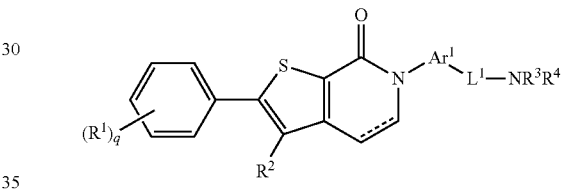

wherein:
"-----" is optionally a bond to form a double bond
q is 1 or 2;
$R^1$ is independently selected from the group consisting of hydrogen, $C_1$-$C_4$ alkyl, halo, hydroxy, $C_1$-$C_4$ haloalkyl, $C_1$-$C_4$ alkoxy, $C_1$-$C_4$ haloalkoxy, —O—$C_3$-$C_8$ cycloalkyl, amino, —SO$_2$$C_1$-$C_4$ alkyl, and $C_1$-$C_4$ alkyl$NR^6R^{6'}$;
$R^2$ is hydrogen or $C_1$-$C_4$ alkyl;
$Ar^1$ is thienyl or pyridyl each optionally substituted with one or two groups independently selected from the group consisting of $C_1$-$C_4$ alkyl, —$OC_1$-$C_4$ alkyl, halo, $C_1$-$C_4$ haloalkyl, and —$OC_1$-$C_4$ haloalkyl;
$L^1$ is selected from the group consisting of a bond, —OCH$_2$—, —OCHR$^7$CH$_2$—, —OCH$_2$CHR$^7$—, —OCHR$^7$CH$_2$CH$_2$—, —OCH$_2$CHR$^7$CH$_2$—, NR$^7$CH$_2$CH$_2$, —NR$^7$CH$_2$CH$_2$CH$_2$, —C(O)NR$^7$CHR$^8$—, —C(O)NR$^7$CH$_2$CHR$^8$—, and —C(O)NR$^7$CHR$^8$CH$_2$;
$R^3$ and $R^4$ are independently selected from the group consisting of hydrogen, $C_1$-$C_4$ alkyl, or $R^3$ and $R^4$ combine together with the nitrogen atom to which they are attached to form an optionally substituted 5 to 7-member heterocyclic ring; or one of $R^3$ and $R^4$ combine with $L^1$ at a position α, β, γ, or δ to the nitrogen of $NR^3R^4$ to form a nitrogen containing 5 to 7-member heterocyclic group with $L^1$ said heterocyclic group being optionally substituted with one to three substituents independently selected from the group consisting of oxo, hydroxy, —OR$^6$, $C_1$-$C_4$ alkyl, —C(O)O$C_1$-$C_4$ alkyl $C_1$-$C_4$ alkyl$NR^6R^{6'}$; and $NR^6R^{6'}$;
each $R^6$ and $R^{6'}$ is independently selected from the group consisting of hydrogen, $C_1$-$C_4$ alkyl, benzyl, $C_3$-$C_8$ cycloalkyl, and $C_4$-$C_8$ alkylcycloalkyl;

each $R^7$ is independently selected from the group consisting of hydrogen and $C_1$-$C_4$ alkyl or each $R^7$ or combines with one or both of $R^3$ and $R^4$ to form a 5-7 member nitrogen containing heterocycle;

each $R^8$ is independently selected from the group consisting of hydrogen and $C_1$-$C_4$ alkyl or each $R^8$ combines with one or both of $R^3$ and $R^4$ to form a 5-7 member nitrogen containing heterocycle; or a pharmaceutically acceptable salt, or enantiomer, diastereomer or mixture of diastereomers thereof.

The present invention also relates to a pharmaceutical composition comprising a compound of formula I.

In another embodiment, the pharmaceutical composition of the present invention may be adapted for use in treating obesity and related diseases.

The present invention also relates to a method for treating obesity and related diseases comprising administering a therapeutically effective amount of a compound of formula I to a patient in need thereof.

The present invention also relates to use of a compound according to formula I for treating obesity and related diseases.

The present invention is also relates to the use of a compound of formula I for therapy.

The present invention is related to the use of a compound of formula I for the manufacture of a medicament for treating obesity and related diseases.

DETAILED DESCRIPTION

For the purposes of the present invention, as disclosed and/or claimed herein, the following terms and definitions apply unless otherwise stated.

General chemical terms used in the description of compounds herein described bear their usual meanings. For example, the term "$C_1$-$C_4$ alkyl" refers to a straight or branched aliphatic chain of 1 to 4 carbon atoms (or as indicated) and isomers thereof including but not limited to methyl, ethyl, propyl, iso-propyl, n-butyl, and the like as indicated.

The term "$C_3$-$C_6$ cycloalkyl" refers to a saturated carbocyclic ring having from 3 to 6 carbon atoms including cyclopropyl, cyclobutyl, cyclopentyl and cyclohexyl. Similarly, the term "$C_3$-$C_4$ cycloalkyl" refers to the group consisting of cyclopropyl, and cyclobutyl. The term $C_3$-$C_6$ haloalkyl encompasses the term $C_3$-$C_5$ haloalkyl, etc.

The term "halo" refers to a halogen, i.e., chloro, bromo, iodo and fluoro.

The term "$C_1$-$C_4$ haloalkyl" refers to a $C_1$-$C_4$ alkyl group substituted with one, two, three or more halogen atoms as indicated or chemically appropriate. Examples of $C_1$-$C_4$ haloalkyl include but are not limited to trifluoromethyl, chloroethyl, and 2-chloropropyl. Similarly, a "$C_2$-$C_3$ haloalkyl" is a methyl or ethyl group substituted with from one to the maximum applicable number of halogen atoms, preferably chloro or fluoro. One of skill in the art is aware that a $C_1$-$C_4$ haloalkyl encompasses a $C_1$-$C_3$ haloalkyl, and a $C_2$-$C_3$ haloalkyl.

A "$C_1$-$C_4$ alkoxy" group is a $C_1$-$C_4$ alkyl (or as indicated) moiety connected through an oxy linkage. Examples of alkoxy groups include but are not limited to methoxy(-OMe), ethoxy(-OEt), propoxy(-OPr), isopropoxy(-OiPr), butoxy(-OBu), etc. Similarly, the term "$C_1$-$C_3$ alkoxy" includes methoxy(-OMe), ethoxy(-OEt), propoxy(-OPr), isopropoxy(-OiPr). Likewise, $C_1$-$C_2$ alkoxy includes OMe and OEt groups.

The term "$C_1$-$C_4$ haloalkoxy" encompasses $C_1$-$C_4$ alkoxy wherein one or more of the hydrogen atoms on the alkyl portion have been replaced with halogens. Examples of haloalkoxy groups include difluoromethoxy, trifluoromethoxy, 2-haloethoxy, 2,2,2-trifluoroethoxy, 4,4,4-trifluorobutoxy, up to and including like groups having the indicated number of carbon atoms. For example, $C_1$-$C_2$ haloalkoxy includes $OCF_3$ and $OCH_2CH_2F$ groups and others having one or two carbon atoms and appropriate number of halogens.

The term "$C_1$-$C_3$ alkylalcohol" encompasses a monovalent radical alcohol including methanol, ethanol, propanol and isopropanol used as a terminal appendage to the group to which it is attached. Similar terms encompass alcohols having the indicated number of carbon atoms. For example, $C_1$-$C_2$ alkylalcohol includes methanol and ethanol.

The invention also contemplates that the term $C_1$-$C_4$ alkyl encompasses the specified alkyl which may result in chirality as appended. Such resulting chiral compounds are also objects of the present invention.

The terms "α", "β", "γ", or "δ" refer respectively to a position 1, 2, 3, or 4 atom-positions from the nitrogen of $NR^3R^4$ counting backward on formula I. The terms "α", "β", "γ", or "δ" designate the position on a compound of formula I where one of $R^3$ and $R^4$ forms a heterocyclic ring with an atom on the $L^1$ chain (linker $L^1$). One of skill in the art is aware that the combination of $R^3$ and $R^4$ or combination of $R^3$ or $R^4$ with $L^1$ to form a 4 to 7 member nitrogen containing heterocyclic ring, as disclosed and used herein requires an implied abstraction of one or two hydrogen atoms from a CH, or $CH_2$ group as necessary from one or both combining groups. Furthermore, as used herein, it is contemplated that when one of $R^3$ and $R^4$ combines with $L^1$ to form a (4 to 7 member) nitrogen containing heterocyclic ring the other of $R^3$ and $R^4$ is either a hydrogen atom or an optional substituent on said ring wherein optional substituents are as defined below or as indicated for the particular group of compounds of formula I.

The term "nitrogen containing heterocyclic" means a saturated, partially unsaturated, fully unsaturated, or aromatic 4, 5, 6 or 7 membered (or as otherwise specified) optionally having additional heteroatoms selected from nitrogen and oxygen. Representative heterocyclic groups include azetidinyl, morpholinyl, piperidinyl, piperazinyl, diazepanyl, and pyrrolidinyl. Thus as used herein the term 4 to 7 member nitrogen containing heterocyclic group encompasses separately and/or collectively 4 to 6, 5-6, 5-7, and 4 to 7 member nitrogen containing heterocyclic groups.

The term "oxo" as used herein implies an oxygen atom attached to a carbon atom which is part of a ring or a chain to form a carbonyl group.

The present invention provides chemically stable compounds and one of skill in the art is aware of the particular combination of substituents within the scope defined herein that leads to chemical stability including implied addition or subtraction of hydrogen atom(s) to achieve the described and/or intended chemically stable compound.

The term "suitable solvent" refers to any solvent, or mixture of solvents, inert to the ongoing reaction, that sufficiently solubilizes the reactants to afford a medium within which to effect the desired reaction.

As used herein, the term "patient" refers to humans, companion animals (e.g. dogs and cats and the like), and livestock animals.

The terms "treatment" "treat" and "treating" include ameliorating, halting, restraining, slowing, and reversing the progression of, or reducing the severity of pathological symptoms of obesity and related diseases.

As used herein, the term "therapeutically effective amount" means an amount of a compound of the present invention, i.e., a compound of formula I that is capable of treating the symptoms of the various pathological conditions herein described.

The term "pharmaceutically acceptable" is used herein as an adjective and means substantially non-deleterious to the recipient patient.

The terms "diseases related to obesity" or "related diseases" as used herein refer to symptoms, diseases or conditions caused by, exacerbated by, induced by, or adjunct to the condition of being obese. Such diseases, conditions and/or symptoms include but are not limited to eating disorders (bulimia, anorexia nervosa, etc.), diabetes, diabetic complications, diabetic retinopathy, depression, anxiety, hypertension, cerebral hemorrhage, congestive heart failure, atherosclerosis, rheumatoid arthritis, stroke, hyperlipidemia, hypertriglycemia, hyperglycemia, and hyper lipoproteinemia.

Pharmaceutically acceptable salts and methodologies for preparing them are well known to one of skill in the art. See, e.g. P. Stahl, et al. Handbook of Pharmaceutical Salts: Properties, Selections and Use (VCHA/Wiley-VCH, 200); S. M. Berge, et al., "Pharmaceutical Salts" Journal of Pharmaceutical Sciences, Vol. 66, No. 1, January 1977.

Preferred Compounds of the Invention

Certain compounds of the invention are particularly interesting and preferred. The following listing sets out several groups of preferred compounds. It will be understood that each of the listings may be combined with other listings or groupings described herein to create additional groups of preferred compounds.

Preferred $R^1$ groups are independently selected from the group consisting of chloro, fluoro, methyl, trifluoromethyl, methoxy, trifluoromethoxy, propoxy, isopropoxy, and cyclopropoxy. More preferably, $R^1$ is selected from the group consisting of fluoro, chloro, cyclopropoxy, trifluoromethoxy, and methoxy.

Preferably $R^a$ and $R^b$ are independently hydrogen, chloro, fluoro, or methoxy.

$R^2$ is preferably hydrogen.

Preferably $L^1$ is selected from the group consisting of a bond, —OCH$_2$CH$_2$—, —OCH$_2$CH$_2$CH$_2$—, —C(O)CH$_2$CH$_2$—, —NHC(O)CH$_2$CH$_2$—, —NHC(O)CH$_2$CH$_2$CH$_2$—, —C(O)NHCH$_2$CH$_2$—, and —C(O)NHCH$_2$CH$_2$CH$_2$—. More preferably $L^1$ is selected from the group consisting of a bond, —OCH$_2$CH$_2$—, —OCH$_2$CH$_2$CH$_2$—, —C(O)CH$_2$CH$_2$—, —NHC(O)CH$_2$CH$_2$—, and —C(O)NHCH$_2$CH$_2$—. Particularly preferred $L^1$ is a bond or —OCH$_2$CH$_2$—, —OCH$_2$CH$_2$CH$_2$—, —C(O)CH$_2$CH$_2$—, or —NHC(O)CH$_2$CH$_2$—.

Preferably, $R^3$ and $R^4$ combine with each other and the nitrogen atom to which they are attached to form an optionally substituted 4 to 7 member nitrogen containing heterocyclic ring; or one of $R^3$ and $R^4$ combine with $L^1$ at a position α, β, or γ to the nitrogen of NR$^3$R$^4$ to form an optionally substituted 4 to 7 member nitrogen containing heterocyclic ring; wherein each 4 to 7 member nitrogen containing heterocyclic ring formed by $R^3$ and $R^4$ or $L^1$ and either of $R^3$ and $R^4$ is selected from the group consisting of morpholino, pyrrolidinyl, piperazinyl, piperidinyl, and diazepanyl; and wherein each 4 to 7 member nitrogen containing heterocyclic ring is optionally substituted with one or two groups independently selected from the group consisting of methyl, halo, oxo, hydroxy, amino, cyclopropyl, cyclobutyl, C(O)CH$_3$, C$_1$-C$_2$ haloalkyl, C$_1$-C$_2$ alkylalcohol, and NR$^6$R$^{6'}$.

Preferably $R^5$ is hydrogen, methyl, methoxy or cyano. More preferably, $R^5$ is hydrogen or methyl. Most preferably, $R^5$ is hydrogen.

A preferred $R^6$ or $R^{6'}$ is independently selected from hydrogen, C$_1$-C$_4$ alkyl, C$_1$-C$_2$ haloalkyl, C$_1$-C$_2$ alkylalcohol, and C$_3$-C$_4$ cycloalkyl. Also preferred are $R^6$ and $R^{6'}$ groups which combine with each other and the nitrogen atom to which they are attached to form 4 to 6 member nitrogen containing heterocyclic ring optionally substituted with methyl, fluoro or hydroxy.

Also preferred is a compound of formula I wherein
$R^1$ is chloro, methoxy, fluoro, trifluoromethyl, or cyclopropoxy;
$R^a$ and $R^b$ are independently hydrogen, fluoro, or methoxy;
$R^2$ is hydrogen;
$L^1$ is selected from the group consisting of a bond, —C(O)CH$_2$CH$_2$—, —NHC(O)CH$_2$CH$_2$—, —NHC(O)CH$_2$CH$_2$CH$_2$—, —C(O)NHCH$_2$CH$_2$—, and —C(O)NHCH$_2$CH$_2$CH$_2$—;
$R^3$ and $R^4$ combine together and with the nitrogen atom to which they are attached form an optionally substituted 4 to 7 member nitrogen containing heterocyclic ring; or one of $R^3$ and $R^4$ combine with $L^1$ at a position α, β, or γ to the nitrogen of NR$^3$R$^4$ to form a 4 to 7 member nitrogen containing heterocyclic ring with $L^1$; wherein each 4 to 7-member nitrogen containing heterocyclic ring formed by $R^3$ and $R^4$ or $L^1$ and either of $R^3$ and $R^4$ is selected from azetidinyl, pyrrolidinyl, morpholino, piperidinyl, piperazinyl, and diazepanyl, and wherein each 4 to 7 member nitrogen containing heterocyclic ring is optionally substituted with one or two groups independently selected from the group consisting of OH, OC$_1$-C$_3$ alkyl, OC$_1$-C$_2$ haloalkyl, NHC$_1$-C$_2$ alkylalcohol, NH$_2$, NHCH$_3$, N(CH$_3$)$_2$, NHcyclopropyl, N(cyclopropyl)$_2$, amino-substituted pyrrolidinyl, fluoro-substituted pyrrolidinyl, C(O)CH$_3$, and NHC$_2$-C$_3$ haloalkyl; and
$R^5$ is hydrogen or methyl.

Also preferred is a compound of formula I wherein
$R^1$ is chloro, methoxy, fluoro, trifluoromethyl, or cyclopropoxy;
$R^a$ and $R^b$ are independently hydrogen, fluoro, or methoxy;
$R^2$ is hydrogen;
$L^1$ is a bond;
$R^3$ and $R^4$ combine together and with the nitrogen atom to which they are attached to form a 4 to 7 member nitrogen containing heterocyclic ring selected from the group consisting of pyrrolidinyl, morpholino, piperidinyl, and piperazinyl, each optionally substituted with one or two groups independently selected from the group consisting of OH, fluoro, OC$_1$-C$_3$ alkyl, OC$_1$-C$_2$ haloalkyl, NHC$_1$-C$_2$ alkylalcohol, NH$_2$, NHCH$_3$, N(CH$_3$)$_2$, NHcyclopropyl, N(cyclopropyl)$_2$, fluoro-substituted pyrrolidinyl, C(O)CH$_3$, and NHC$_2$-C$_3$ haloalkyl;
$R^5$ is hydrogen or methyl.

Also preferred is a compound of formula I wherein
$R^1$ is chloro, methoxy, fluoro, trifluoromethyl, or cyclopropoxy;
$R^a$ and $R^b$ are independently hydrogen fluoro or methoxy
$R^2$ is hydrogen;
$L^1$ is selected from the group consisting of a bond, —C(O)CH$_2$CH$_2$—, —NHC(O)CH$_2$CH$_2$—, —NHC(O)CH$_2$CH$_2$CH$_2$—, —C(O)NHCH$_2$CH$_2$—, and —C(O)NHCH$_2$CH$_2$CH$_2$—.
$R^3$ and $R^4$ combine together and with the nitrogen atom to which they are attached form an optionally substituted 4 to 7 member nitrogen containing heterocyclic ring; or one of $R^3$ and $R^4$ combine with $L^1$ at a position α, β, or γ to the nitrogen of $NR^3R^4$ to form a 4 to 6 member nitrogen containing heterocyclic ring with $L^1$; wherein each 4 to 7-member nitrogen containing heterocyclic ring formed by $R^3$ and $R^4$ or $L^1$ and either of $R^3$ and $R^4$ is selected from azetidinyl, pyrrolidinyl, morpholino, piperidinyl, piperazinyl, and diazepanyl, each 4 to 7 member nitrogen containing heterocyclic ring is optionally substituted with one or two groups independently selected from the group consisting of OH, fluoro, $OC_1$-$C_3$ alkyl, $OC_1$-$C_2$ haloalkyl, $NHC_1$-$C_2$ alkylalcohol, $NH_2$, $NHCH_3$, $N(CH_3)_2$, NHcyclopropyl, $N(cyclopropyl)_2$, amino-substituted pyrrolidinyl, fluoro-substituted pyrrolidinyl, $C(O)CH_3$, and $NHC_2$-$C_3$ haloalkyl; and
$R^5$ is hydrogen or methyl.

Also preferred is a compound of formula I wherein:
$R^1$ is chloro, methoxy, fluoro, trifluoromethyl, or cyclopropoxy;
$R^a$ and $R^b$ are independently hydrogen, fluoro, or methoxy;
$R^2$ is hydrogen;
$L^1$ is a bond;
$R^3$ and $R^4$ combine with each other and with the nitrogen atom to which they are attached to form a 4 to 7 member heterocyclic ring selected from pyrrolidinyl, morpholino, piperidinyl, and piperazinyl, each optionally substituted with one or two groups independently selected from OH, fluoro, $OC_1$-$C_3$ alkyl, $OC_1$-$C_2$ haloalkyl, $NHC_1$-$C_2$ alkylalcohol, $NH_2$, $NHCH_3$, $N(CH_3)_2$, NHcyclopropyl, $N(cyclopropyl)_2$, amino-substituted pyrrolidinyl, fluoro-substituted pyrrolidinyl, $C(O)CH_3$, $NR^6R^{6'}$, $NHCH_2CHF_2$, and $NHCH_2CH_2F$;
$R^6$ and $R^{6'}$ are independently hydrogen, methyl, ethyl, 2-fluoroethyl, 2,2-difluoroethyl, cyclopropyl, cyclobutyl, or $R^6$ and $R^{6'}$ combine to form a 4 to 6 member nitrogen containing heterocyclic ring optionally substituted with a group selected from hydroxy, fluoro, and methyl.

Also preferred is a compound of formula I wherein:
$R^1$ is chloro, methoxy, fluoro, trifluoromethyl, or cyclopropoxy;
$R^a$ and $R^b$ are independently hydrogen, fluoro, or methoxy;
$R^2$ is hydrogen;
$L^1$ is $OCH_2CH_2$—, —$NHC(O)CH_2$—, —$NHC(O)CH_2CH_2$—, or —$C(O)NHCH_2CH_2$—;
$R^3$ and $R^4$ combine with each other to form a 4 or 7 member heterocyclic ring selected from pyrrolidinyl, morpholino, piperidinyl, and piperazinyl wherein each 4 to 7 member nitrogen containing heterocyclic ring is optionally substituted with one or two groups independently selected from OH, $NR^6R^{6'}$, halo, $C_1$-$C_3$ alkyl and $C_1$-$C_3$ haloalkyl;
$R^5$ is hydrogen;
$R^6$ and $R^{6'}$ are independently hydrogen, methyl, ethyl, 2-fluoroethyl, 2,2-difluoroethyl, cyclopropyl, cyclobutyl, or $R^6$ and $R^{6'}$ combine to form a 4 to 6 member heterocyclic ring optionally substituted with a group selected from hydroxy, fluoro, and methyl.

Also preferred is a compound of formula I wherein:
$R^1$ chloro, methoxy, fluoro, trifluoromethyl, or cyclopropoxy;
$R^a$ and $R^b$ are independently hydrogen, fluoro, or methoxy;
$R^2$ is hydrogen;
$L^1$ is a bond;
$R^3$ and $R^4$ combine with each other to form a 4 to 7 member nitrogen containing heterocyclic ring selected from pyrrolidinyl, morpholino, piperidinyl, and piperazinyl wherein each nitrogen containing heterocyclic ring is optionally substituted with one or two groups independently selected from OH, $NR^6R^{6'}$, halo, $C_1$-$C_3$ alkyl and $C_1$-$C_3$ haloalkyl;
$R^5$ is hydrogen or methyl;

$R^6$ and $R^{6'}$ are independently hydrogen, $CH_2CHF_2$, methyl, cyclopropyl or cyclobutyl.

Also preferred is a compound of formula I wherein:
$R^1$ is chloro, methoxy, fluoro, trifluoromethyl, or cyclopropoxy;
$R^a$ and $R^b$ are independently hydrogen, fluoro, or methoxy;
$R^2$ is hydrogen;
$L^1$ is $OCH_2CH_2$—, or —$OCH_2CH_2CH_2$—;
$R^3$ and $R^4$ combine with each other to form a 4 or 7 member heterocyclic ring selected from pyrrolidinyl, morpholino, piperidinyl, diazepanyl, and piperazinyl wherein each 4 to 7 member nitrogen containing heterocyclic ring is optionally substituted with one or two groups independently selected from OH, $NR^6R^{6'}$, halo, $C_1$-$C_3$ alkyl and $C_1$-$C_3$ haloalkyl;
$R^5$ is hydrogen;
$R^6$ and $R^{6'}$ are independently hydrogen, methyl, ethyl, 2-fluoroethyl, 2,2-difluoroethyl, cyclopropyl, cyclobutyl, or $R^6$ and $R^{6'}$ combine to form a 4 to 6 member heterocyclic ring optionally substituted with a group selected from hydroxy, fluoro, and methyl.

Also preferred is a compound of formula I wherein:
$R^1$ is chloro, methoxy, fluoro, trifluoromethyl, or cyclopropoxy;
$R^a$ and $R^b$ are independently hydrogen, fluoro, or methoxy;
$R^2$ is hydrogen;
$L^1$ is —$NHC(O)CH_2$—, —$NHC(O)CH_2CH_2$—, or —$C(O)NHCH_2CH_2$—;
$R^3$ and $R^4$ combine with each other to form a 4 or 7 member heterocyclic ring selected from pyrrolidinyl, morpholino, piperidinyl, and piperazinyl wherein each 4 to 7 member nitrogen containing heterocyclic ring is optionally substituted with one or two groups independently selected from OH, $NR^6R^{6'}$, halo, $C_1$-$C_3$ alkyl and $C_1$-$C_3$ haloalkyl;
$R^5$ is hydrogen;
$R^6$ and $R^{6'}$ are independently hydrogen, methyl, ethyl, 2-fluoroethyl, 2,2-difluoroethyl, cyclopropyl, cyclobutyl, or $R^6$ and $R^{6'}$ combine to form a 4 to 6 member heterocyclic ring optionally substituted with a group selected from hydroxy, fluoro, and methyl.

Also preferred is a compound of formula I wherein:
$R^1$ is chloro, fluoro, trifluoromethyl, or cyclopropoxy;
$R^a$ and $R^b$ are independently hydrogen, fluoro, or methoxy;
$R^2$ is hydrogen;
$L^1$ is selected from the group consisting of a bond, —$OCH_2CH_2$—, —$NHC(O)CH_2$—, —$NHC(O)CH_2CH_2$—, and —$C(O)NHCH_2CH_2$—;
$R^3$ and $R^4$ combine with each other and with the nitrogen atom to which they are attached to form a 4 to 7 member nitrogen containing heterocyclic ring; or one of $R^3$ and $R^4$ combine with $L_1$ at a position α, β, or γ from the nitrogen of $NR^3R^4$ to form a heterocyclic ring; wherein each 4 to 7-member nitrogen containing heterocyclic ring formed by the combination of $R^3$ and $R^4$ or $L^1$ and either of $R^3$ and $R^4$ is selected from azetidinyl, pyrrolidinyl, morpholino, piperidinyl, and piperazinyl, and wherein each 4 to 7 member nitrogen containing heterocyclic ring is optionally substituted with one or two groups independently selected from the group consisting of methyl, fluoro, OH, $OCH_3$, $NHCH_2CH_2F$, $NH_2$, $NHCH_3$, $N(CH_3)_2$, NHcyclopropyl, and $N(cyclopropyl)_2$; and
$R^5$ is hydrogen.

Preparing Compounds of the Invention

The compounds of formula I can be prepared by a variety of procedures known in the art and those described below. The products of each step in the Scheme below can be recovered by conventional methods including extraction, evaporation, precipitation, chromatography, filtration, trituration, crystallization, and the like. In the Schemes below all substituents, unless otherwise indicated, are as previously defined and suitable reagents are well known and appreciated in the art.

Scheme 1

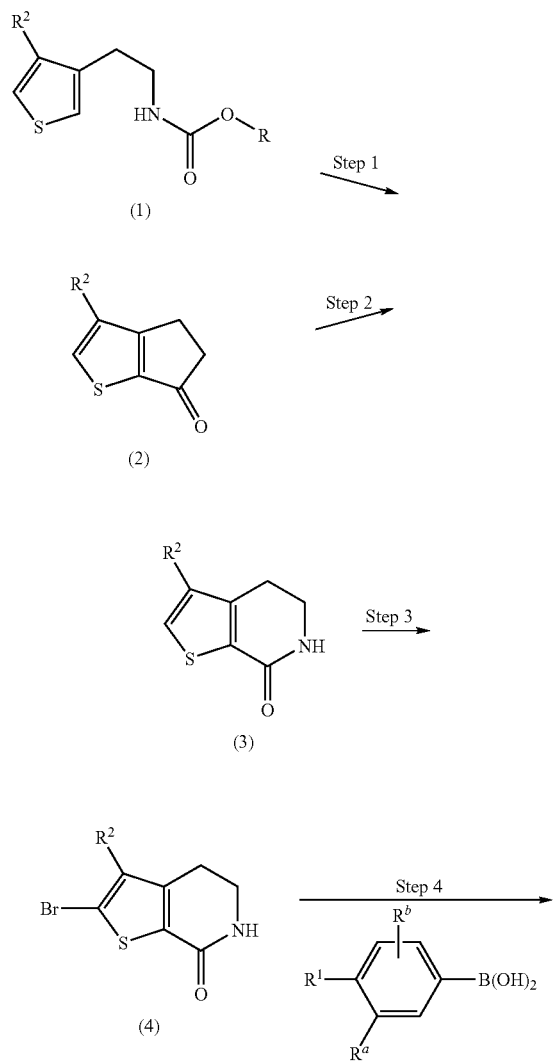

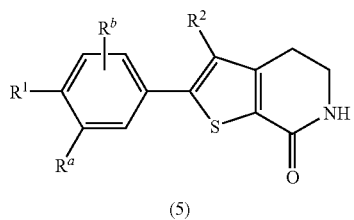

Formation of an intermediate of formula (5) can be carried out in accordance with reactions as depicted in Scheme 1.

In Scheme 1, Step 1, a carbamate of formula (I) is converted to a lactam of formula (3) using a Friedel-Crafts acylation. For example, carbamate (1) is dissolved in excess phosphorous oxychloride and treated with phosphorous pentoxide at about 100-130° C.

Alternatively, in Step 2, the lactam of formula (3) can be obtained by ring expansion of a ketone of formula (2) by treating with hydroxylamine and excess sodium acetate in an alcohol solvent such as MeOH or EtOH. The intermediate imine is isolated by filtration and treated with a strong acid, such as polyphosphoric acid at about 100-150° C. to provide the lactam (3).

The bromination of the thiophene ring to provide bromo-thiophene (4) is achieved by treatment with bromine, in a suitable solvent such as acetic acid, water, or carbon tetrachloride.

The bromo-thiophene of formula (4) is functionalized in Step 4 to an aryl thiophene of formula (5) by using a suitable metal-catalyzed cross-coupling reaction well known to those skilled in the art. For example, the bromo-thiophene (4) is treated with an aryl boronic acid in a solvent such as acetonitrile, DMF, toluene, water, etc. Included in the arylation reaction is a base such as potassium carbonate and a palladium catalyst such as $Pd(OAc)_2$, $Pd(PPh_3)_4$, or $Pd(PPh_3)_2Cl_2$, etc., typically with the addition of a phosphine ligand, such as $PPh_3$.

As will be readily appreciated, compounds of formula (1) and (2) can be readily prepared by methods similar to those described herein using procedures that are well-known and appreciated in the art. For example, compounds of formula (1) are prepared by reduction of a thiophene-3-acetonitrile to the amine and subsequent reaction with ethyl chloroformate. The ketone of formula (2) is readily prepared according to Aparajithan, K., et. al. *J. Heterocyclic Chem.* 1966, 3, 466.

Scheme 2

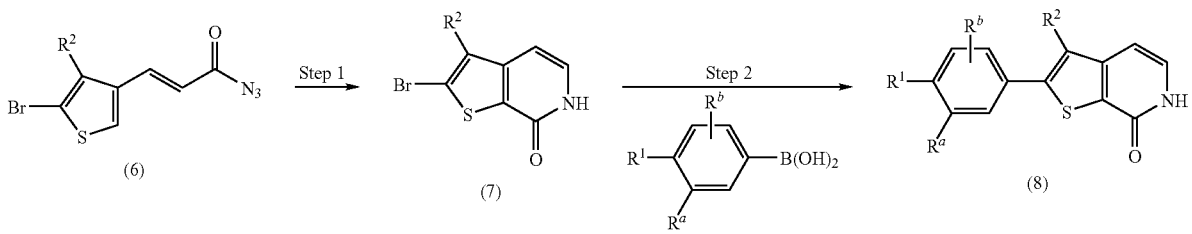

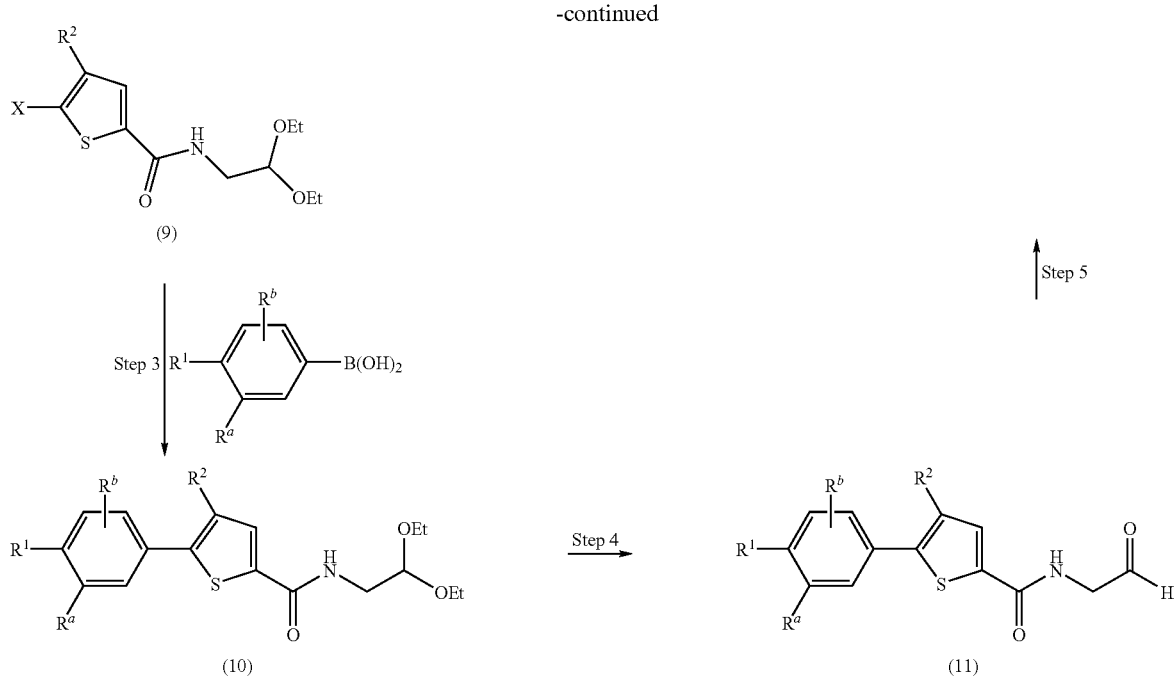

Formation of compounds of formula (8) can be carried out in accordance with methods depicted in Scheme 2. An appropriate compound of formula (9) is one in which X=Cl or Br and $R^2$ is as defined for formula (I). An appropriate compound of formula (8) is one in which $R^1$, $R^a$, $R^b$, and $R^2$ are as defined for formula (I).

In Scheme 2, Step 1, an acyl azide of formula (6) is cyclized under thermal conditions to a thienopyridinone of formula (7). For example, the acyl azide (6) is dissolved in dioxane and added dropwise to a preheated flask (230° C.) containing Dowtherm A®. The bromo-thienopyridinone of formula (7) is functionalized to an aryl-thienopyridinone using a metal-catalyzed cross-coupling reaction as described for Scheme 1, Step 4, above.

In Scheme 2, compounds of formula (8) can also be obtained by methods depicted in Steps 3, 4, and 5. In Step 3, a 5-halothiophene of formula (9) is converted to an aryl-thiophene of formula (10) using a metal catalyzed cross coupling reaction with an arylboronic acid. For example, a 5-halothiophene of formula (9), wherein X=Cl is dissolved in a solvent such as ethanol and treated with an arylboronic acid in the presence of a base such as sodium, potassium, or cesium carbonate. A palladium catalyst is added such as [1,3-bis(2,6-diisopropylphenyl)imidazol-2-ylidene)(3-chloropyridyl)] palladium (II) dichloride and the reaction carried out at a temperature range of about room temperature to about the reflux temperature of the chosen solvent.

In Step 4, an acetal of formula (10) is converted to an aldehyde of formula (11) using acidic conditions commonly known in the art. The preferred conditions use trifluoroacetic acid.

In Scheme 2, Step 5, an aldehyde of formula (11) is cyclized in an intramolecular condensation to afford a thienopyridinone of formula (8) under acidic conditions. The preferred conditions use trifluoromethane sulfonic acid as solvent at a temperature range of about 50 to 150° C. for about 1 to 5 h. The product is isolated by pouring the reaction onto cold water followed by filtration.

As will be readily appreciated compounds of formula (6) and (9) can be prepared by methods and procedures that are described herein or that are known in the art. For example, compounds of formula (6) are prepared by conversion of the corresponding acid (Gronowitz, S.; Ander, I. *Chemica Scripta* 1980, 15, 145) to the acid chloride and subsequent reaction with sodium azide to obtain the acyl azide of formula (6). Compounds of formula (9) are prepared by acylation of a 5-halothiophene-2-carboxylic acid with 2,2-diethoxyethylamine Scheme 3

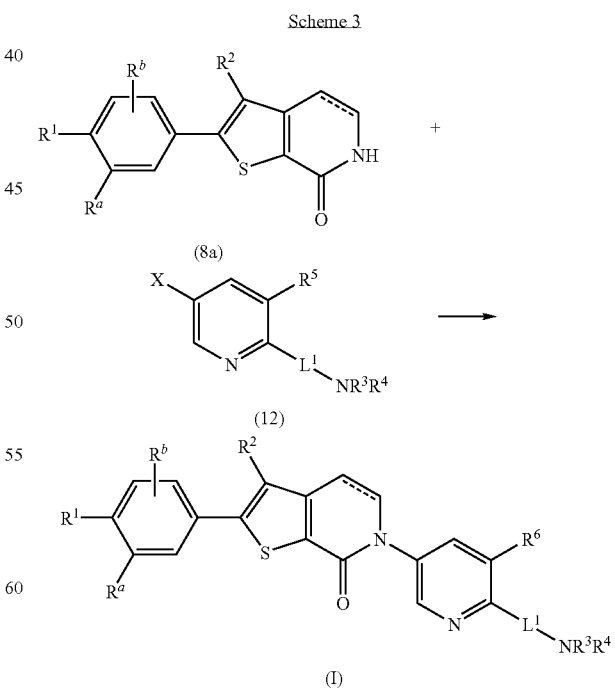

Formation of compounds of formula (I) can be carried out in accordance with methods depicted in Scheme 3. An appropriate compound of formula (8a) is one in which $R^1$, $R^a$, $R^b$, and $R^2$ are as defined for formula (I) and an appropriate compound of formula (12) is one in which $L^1$, $R^3$, $R^4$, and $R^5$ are as defined for formula (I) and X=Br, I, or $OS(O_2)CF_3$ (triflate).

pound of formula (8a), such that the later carried out displacements, acylations, arylations, alkylation, reductive aminations, etc., provide a compound of formula (I). Thus $R^3$ and $R^4$ can be further functionalized after coupling using standard methods known in the art.

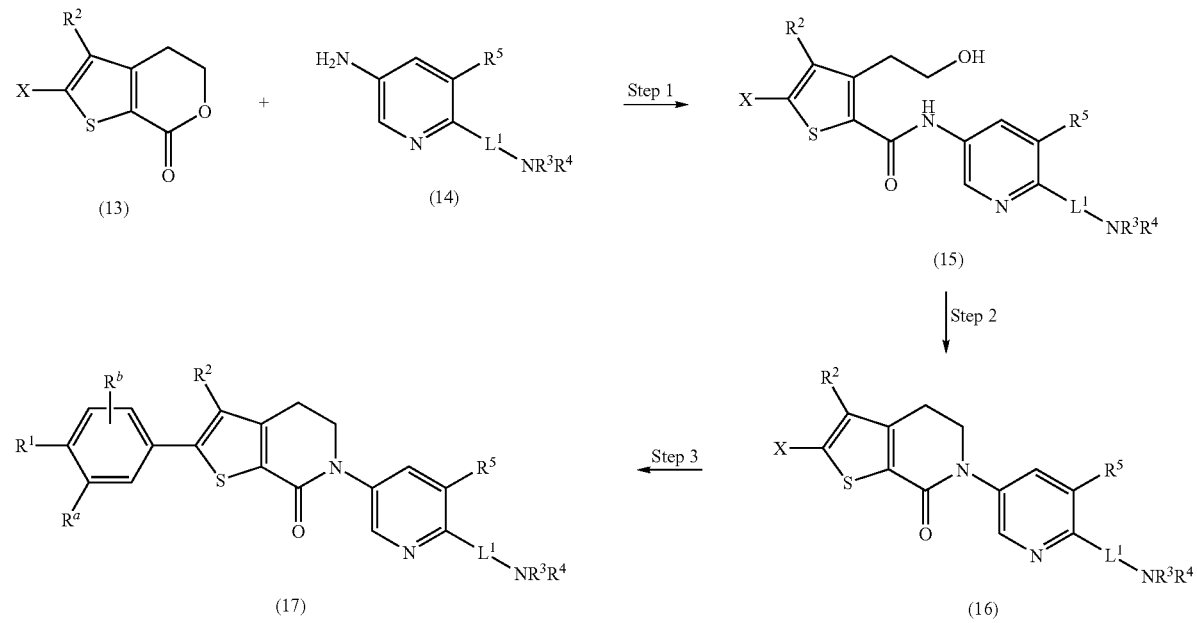

Scheme 4

For example, a compound of formula (8a) is reacted with a compound of formula (12) using catalytic cross-coupling conditions, such as Buchwald arylation of an amide (Yin, J.; Buchwald, S. J. *J. Am. Chem. Soc.* 2002, 124(21), 6043-6048). The coupling reaction uses a base, for example $Cs_2CO_3$, a palladium reagent, for example $Pd_2dba_3$, and a phosphine ligand, for example Xantphos, in a non-protic solvent such as dioxane, toluene, or benzene. The reaction is generally carried out at a temperature range of about RT to about the reflux temperature of the chosen solvent.

Alternatively, the reaction is performed using copper-mediated conditions. For example, a compound of formula (8a) is dissolved in toluene or dioxane and treated with a compound of formula (12), using $K_2CO_3$ or preferably $Cs_2CO_3$ (1.5 to 2.0 eq), N,N'-dimethyl-ethane-1,2-diamine (0.2 to 0.5 eq), and CuI (0.1 to 0.5 eq). The reaction is stirred at a temperature between about 80 to 110° C.

As will be readily appreciated compounds of formula (12) can be readily prepared by methods similar to those described herein or by using procedures that are well-known and established in the art. For example, compounds of formula (12) are prepared by reaction of a pyridyl fluoride or chloride with an alcohol or amine in a nucleophilic displacement. An amide linkage is prepared by acylation of a pyridyl carboxylic acid with an alkyl amine. Compounds of formula (12) wherein $L^1$ contains ketone functionality can be obtained by reaction of a Weinreb amide with (5-bromo-2-pyridinyl) lithium. It will be appreciated by one skilled in the art that the nature and sequence of reactions depends on the nature of $L^1$. Also, it is recognized that the steps required to prepare a compound of formula (12) can be carried out in any order, including after reaction of a partial compound of formula (12) with a com- Formation of compounds of formula (17) can be carried out in accordance with methods depicted in Scheme 4. An appropriate compound of formula (13) is one in which $R^2$ is as defined for formula (I), and X is Br or I.

In Scheme 4, Step 1, a thiophene lactone of formula (13) is converted to an amide of formula (15) using a typical Weinreb protocol (Basha, Anwer; Lipton, M.; Weinreb, Steven M. *Tetrahedron Letters*, 1977, 48, 4171). For example, an aminopyridine of formula (14) is dissolved in an aprotic solvent, such as $CH_2Cl_2$ or toluene, and treated with a 2-2.5M solution of $Me_3Al$ in hexanes. The resulting solution is stirred at a temperature from about 0° C. to room temperature and then treated with a lactone of formula (13). The resulting solution is stirred at a range of between about room temperature and 110° C. for about 3 to 24 hours to give the amide.

In Scheme 4, Step 2, the cyclization reaction to form the lactam of formula (16) can be carried out by at least two variants as discussed below.

In the first variant, the alcohol of formula (15) is converted to a leaving group, preferably mesylate, by reaction with methanesulfonyl chloride in the presence of a suitable base, like triethylamine. The intermediate mesylate is isolated by aqueous work-up and immediately dissolved in a polar anhydrous solvent such as DMF and treated with a base such as sodium hydride (1.5 eq) at about 0-25° C.

In a second variant, Mitsunobu conditions (Maligres, P. E.; et. al. *J. Het. Chem.* 2003, 40(2), 229-241) can also be employed. For example, the amide of formula (12) is dissolved in a suitable anhydrous solvent like THF, $CH_2Cl_2$, toluene, etc., and treated with a trialkyl- or triarylphosphine such as $Me_3P$, $Bu_3P$, or $Ph_3P$ and a dialkylazo-dicarboxylate, such as DEAD or DIAD, at a temperature of about 0° C. to RT.

In Scheme 4, Step 3, the lactam of formula (16) is further functionalized using a metal-catalyzed cross-coupling reaction as described for Scheme 1, Step 4 to obtain an aryl thiophene of formula (17).

As will be appreciated compounds of formula (13) and (14) can be readily prepared by methods similar to those described herein or by using procedures that are well-known and established in the art. For example, a 2-thiophen-3-yl-ethanol can be converted to the chloroformate using triphosgene, followed by cyclization to the lactone (thiophene lactone) using a Lewis acid, such as $AlCl_3$. The thiophene lactone is then halogenated, for example, by treatment with iodine and bis(trifluoroacetoxy)iodobenzene to give a compound of formula (13). Halogenation of the thiophene lactone to afford compound (13) results in a mixture of 2- and 3-halogeno-thiophene latones. The desired 2-halogeno thiophene lactone fraction (13, $R^2$=H) may be isolated by chromatography (confirmable by $H^1NMR$). Compounds of formula (13) wherein $R^2$ is $C_1$-$C_4$ alkyl may be prepared by use of the 3-halogeno thiophene lactone fraction from above. The 3-halogenothiophene lactone is alkylated with an appropriately substituted alkyl substrate using a coupling method such as for example, the Suzuki coupling (with alkyl boronic acid) to afford the 3-alkylthiophene lactone. The 3-alkylthiophene lactone is then halogenated to afford the desired compound of formula (13) wherein $R^2$ is $C_1$-$C_4$ alkyl. Compounds of formula (14) are prepared by nucleophilic aromatic displacement of a p-halo-nitro-pyridine with an alcohol or amine. Subsequent reduction of the nitro group provides an aminopyridine of formula (14).

butyl nitrite in the presence of an inert solvent, such as acetonitrile, from about room temperature to the reflux temperature of the solvent.

In Step 2, a bromothiophene of formula (19) is reacted with (trimethylsilyl)acetylene in a palladium mediated cross-coupling reaction to afford an ethynylthiophene of formula (20). For example, the bromo-thiophene (19) is treated with (trimethylsilyl)acetylene in an inert solvent, such as acetonitrile, DMF, or toluene with addition of a base, such as diisopropylamine and a palladium catalyst such as $Pd(OAc)_2$, $Pd(PPh_3)_4$, or $Pd(PPh_3)_2Cl_2$, etc., typically with the addition of a phosphine ligand, such as $PPh_3$. Preferred conditions use DMF and $Pd(PPh_3)_2Cl_2$ with the addition of CuI at a temperature of about 50 to 150° C. Most preferred is to run the reaction in a microwave reactor for about 30 min.

In Scheme 5, Step 3, an ethynylthiophene of formula (20) is reacted with an aminopyridine of formula (14) to afford an amide and subsequently cyclized in situ to afford a thienopyridinone of formula (21). Typical conditions use the Weinreb protocol as described for Scheme 4, Step 1, using $Me_3Al$ in an inert solvent such as toluene.

As will be readily understood, the steps to prepare the compounds of formula (I), (17) and (21), as depicted in the previous schemes, are dependent upon the particular compound being synthesized, the starting compound, and the relative lability of the substituted moieties. Also contemplated are various protection and deprotection steps as may be required or beneficial for carrying out the reactions above. For example, intermediates of formula (12) and (14) need not be

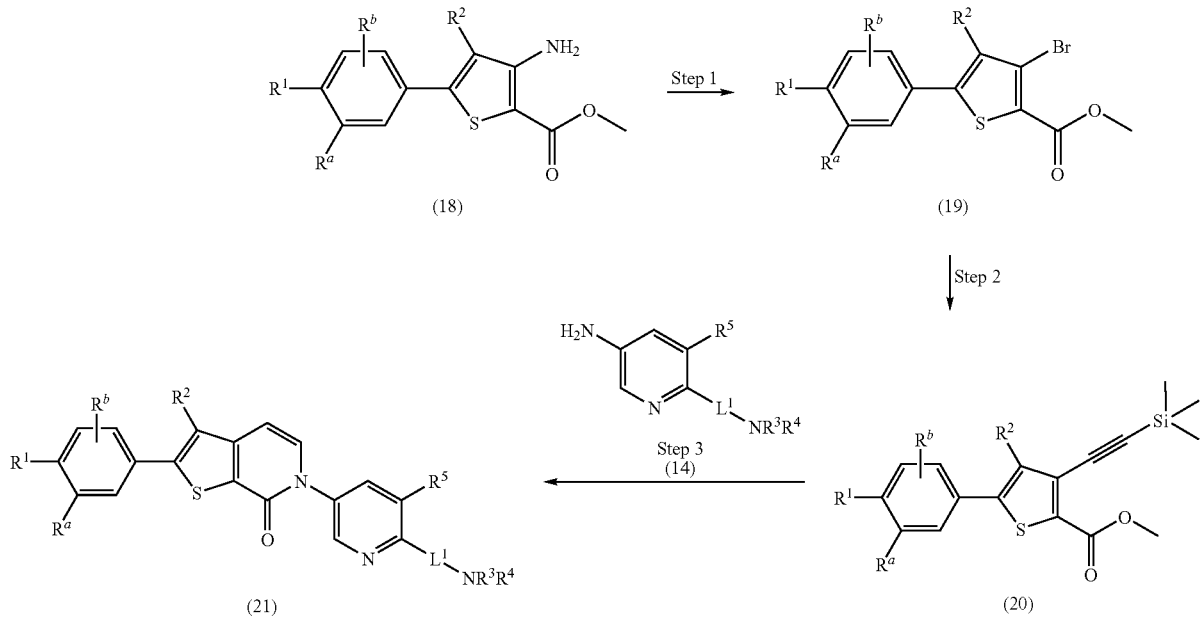

Scheme 5

Formation of compounds of formula (21) can be carried out in accordance with methods depicted in Scheme 5. An appropriate compound of formula (18), (14), and (21) is one in which all variables are as defined for formula (I).

In Scheme 5, Step 1, an aminothiophene of formula (18) is converted to a bromothiophene of formula (19) using a Sandmeyer-like reaction. Preferred conditions use $CuBr_2$ and tertfully elaborated prior to the various coupling or acylation steps described herein. Such intermediates may also have protected amine or hydroxyl functionality that is subsequently deprotected and further reacted to obtain compounds of the invention. The selection and use of suitable protecting groups is well known and appreciated in the art (see for example, Protecting Groups in Organic Synthesis, Theodora Greene (Wiley-Interscience)).

Demonstration of Function

All ligands, radioligands, solvents and reagents useful in these assays are readily available from commercial sources or can be readily prepared by those skilled in the art.

The full-length cDNA for human MCHR1 is cloned from a human adult brain cDNA library (Edge Biosystems, Cat. 38356) by standard polymerase chain reaction (PCR) methodology employing the following primers: sense, 5'-GC-CACCATGGACCT GGAAGCCTCGCTGC-3' (SEQ ID NO:1); anti-sense, 5'-TGGTGCCCTGACTTGGAGGT-GTGC-3' (SEQ ID NO:2). The PCR reaction is performed in a final volume of 50 µL containing 5 µL of a 10× stock solution of PCR buffer, 1 µL of 10 mM dNTP mixture (200 µM final), 2 µL of 50 mM Mg(SO$_4$) (2 mM final), 0.5 µL of 20 µM solutions of each primer (0.2 µM final), 5 µL of template cDNA containing 0.5 ng DNA, 0.5 µL of Platinum Taq High Fidelity DNA polymerase (Gibco Life Technologies) and 36 µL of H$_2$O. PCR amplification is performed on a Perkin Elmer 9600 thermocycler. Perform denaturation for 90 sec at 94° C., and repeat an amplification sequence consisting of 94° C. for 25 sec, 55° C. for 25 sec and 72° C. for 2 mM 30 times, followed by a final elongation step at 72° C. for 10 min. The desired PCR product (1.1 Kb) is confirmed by agarose gel electrophoresis and the band is extracted from the gel by Geneclean (Bio101) following the manufacturer's instructions. Following extraction, clone the cDNA fragment was into pCR2.1-TOPO plasmid (Invitrogen Corp) to confirm the identity and sequence.

In order to generate cell lines stably expressing MCHR1, subclone the insert into the Xba I and Not I sites of pcDNA (+)-3.1-neomycin (Invitrogen). Purify by Qiagen Maxi-prep kit (QIAGEN, Inc.), transfect the plasmid by Fugene 6 (Roche Applied Science) into AV12 cells that has been previously transfected with the promiscuous G protein G$_{\alpha15}$. The transfected cells are selected by G418 (800 µg/mL) for 10-14 days and single colonies are isolated from culture plates. The G418-resistant colonies are further selected for MCHR1 expression by measuring MCH-stimulated Ca$^{2+}$ transients with a fluorometric imaging plate reader (FLIPR, Molecular Devices).

Typically, individual clones are plated out in 96-well plates at 60,000 cells per well in 100 µL of growth medium (Dulbecco's modified Eagle's medium (DMEM), 5% fetal bovine serum, 2 mM L-glutamine, 10 mM HEPES, 1 mM sodium pyruvate, 0.5 mg/ml Zeocin, and 0.5 mg/mL Geneticin). After 24 h at 37° C., remove medium and replace with 50 µL of dye loading buffer (Hank's balanced salt solution (HBSS) containing 25 mM HEPES, 0.04% Pluronate 127 and 8 µM Fluo3 Both from Molecular Probes)). After a 60 min incubation with the dye loading buffer at room temperature, aspirate the dye loading buffer and replace with 100 µL of HEPES/HBBS. Place the cell plate and the compound plate containing 2 µM MCH in buffer in the FLIPR and take a basal reading for 10 sec. The FLIPR then transfers 100 µl of the 2 µM MCH (for a final concentration in the assay of 1 µM MCH) to the cell plate and reads for 105 sec for a complete calcium flux peak in response to the agonist (1 µM MCH). To correct for variations between clones in numbers of cells per well, normalize the MCH response to the response induced by epinephrine.

Both the $^{125}$I-MCH binding and functional GTPγ$^{35}$S binding assays employ membranes isolated from a clone designated as clone 43. Typically, cells from 20 confluent T225 flasks are processed by washing the monolayers in cold phosphate-buffered saline (PBS), scraping the cells into same and re-suspending the cell pellet in (10 ml/gram of paste) in membrane prep buffer, pH 7.4 (250 mM Sucrose, 50 mM HEPES, pH 7.5, 1 mM MgCl$_2$, and protease inhibitors (1 Complete® tablet-EDTA (Roche Diagnostics), per 100 ml of membrane prep buffer). The cells were homogenized with a motor-driven Teflon-glass Potter-Elvehjem homogenizer using 5-10 strokes, followed by centrifugation at 260×g for 15 min at 4° C. The supernatant is collected and the pellets are resuspended in the membrane prep buffer and rehomogenized and centrifuged again at 260×g for 15 min at 4° C. for a total of 3 times. The pellets may then be discarded. The combined supernates are centrifuged at 30,000×g for 60 mins at 4° C. The membrane pellet is resuspended in membrane prep buffer, to achieve a protein concentration of ~3-5 mg/mL (Pierce BCA assay with Bovine serum albumin as standard). Store aliquots at −80° C.

Binding of compounds to MCHR1 is assessed in a competitive binding assay employing $^{125}$I-MCH, compound and clone 43 membranes. Perform assays in 96-well Costar 3632 white clear bottom plates in a total volume of 200 µL containing 25 mM HEPES, pH 7.4, 10 mM CaCl$_2$, 2 mg/mL bovine serum albumin, 0.5% dimethyl sulfoxide (DMSO), 4-12 µg of clone 43 membranes, 200 pM $^{125}$I-MCH(NEN), 2.5 mg/mL of wheat germ agglutinin scintillation proximity assay beads (WGA-SPA beads, Amersham Inc., now GE Healthcare) and a graded dose of test compound. Non-specific binding is assessed in the presence of 0.1 µM unlabeled MCH. Bound $^{125}$I-MCH is determined by placing sealed plates in a Microbeta Trilux (Perkin Elmer Life and Analytical Sciences Inc.) and counting after a 12 h delay.

IC$_{50}$ values (defined as the concentration of test compound required to reduce specific binding of $^{125}$I-MCH by 50%) are determined by fitting the concentration-response data to a 4-parameter model (max response, min response, Hill coefficient, IC$_{50}$) using Excel® (Microsoft Corp.). K$_i$ values are calculated from IC$_{50}$ values using the Cheng-Prusoff approximation as described by Cheng et al. (Relationship between the inhibition constant (K$_i$) and the concentration of inhibitor which causes 50% inhibition (IC$_{50}$) of an enzymatic reaction, *Biochem. Pharmacol.*, 22: 3099-3108 (1973)). Exemplified compounds show a Ki of <1 µM under the binding assay conditions. Specifically, the compound of Example 55 exhibits an average MCHR1 Ki of about 9 nM.

Functional antagonism of MCH activity is assessed by measuring the ability of test compound to inhibit MCH-stimulated binding of GTPγ$^{35}$S to clone 43 membranes. outperform assays in Costar 3632 white clear bottom plates in a total volume of 200 µl containing 50 mM Hepes, pH 7.4, 5 mM MgCl$_2$, 10 µg/ml saponin, 1.0 mg/mL bovine serum albumin, 100 mM NaCl, 3 µM GDP, 0.3 nM GTPγ$^{35}$S, 10 nM MCH (approximately equal to EC$_{90}$), 0.4 mg/ml of clone 43 membranes, 5.0 mg/ml of wheat germ agglutinin scintillation proximity assay beads (WGA-SPA beads, Amersham Inc., now GE Healthcare) and a graded dose of test compound. Seal the plates and leave for 16-18 h at 4° C. After a 1 h delay to allow plates to equilibrate to ambient temperature, determine bound GTPγ$^{35}$S by counting in a Microbeta Trilux (Perkin Elmer Life and Analytical Sciences Inc).

Determine IC$_{50}$ values (defined as the concentration of test compound required to reduce MCH-stimulated GTPγ$^{35}$S binding by 50%) by fitting the concentration-response data to a 4-parameter model (max response, min response, Hill coefficient, IC$_{50}$) using Excel (Microsoft). After verifying competitive antagonism by Schild analysis, calculate K$_b$ values from the IC$_{50}$ values for each antagonist and the EC$_{50}$ for MCH (determined independently) using a modification of the Cheng-Prusoff approximation as described by Leff and Dougal (*Trends Pharmacol. Sci.* (1993) 14: 110-112). Exemplified compounds show K$_b$ values of <1 µM under the functional assay conditions disclosed herein. Specifically, the compound of Example 5 shows a MCHR1 Kb value of about 7 nM.

To demonstrate in vivo efficacy, administer compounds of the invention by oral gavage to diet-induced obese male Long-Evans rats (Harlan, IN) weighing 450-500 g. Vehicle consisted of 10% acacia and 0.15% saccharin in water.

House animals individually in a temperature regulated room (24° C.) with a reverse 12 hour light/dark cycle (dark 10:00/22:00). Make water and food (Teklad 95217, Harlan, WI) available ad libitum. Dose compounds orally once a day before onset of dark for 3 days. Measure daily food intake and body weight change for the 3 day period. The compound of Example 5 produced an average body weight reduction of about 11 grams @ 10 mg/Kg versus vehicle control.

Utility

As antagonists of the MCHR1 binding, a compound of the present invention is useful in treating conditions in human and non-human (especially companion) animals in which the MCHR1 receptor has been demonstrated to play a role. By inhibiting MCH activity the compounds of the present invention provide anorexic effects. That is, the compounds of the invention are useful as appetite suppressants and/or weight loss agents for the treatment of obesity. The compounds are thus useful for treating conditions caused, exacerbated, resulting from, or adjunct to obesity.

In treating non-human, non-companion animals, the compounds of the present invention are useful for reducing weight gain and/or improving the feed utilization efficiency and/or increasing lean body mass.

The compounds of the present invention may be administered by a variety of routes including oral, rectal, transdermal, subcutaneous, intravenous, intramuscular, and intranasal. These compounds preferably are formulated prior to administration, the selection of which formulation to use for a particular patient will be decided by the attending physician. Thus, another aspect of the present invention is a pharmaceutical composition comprising an effective amount of a compound of formula I, or a pharmaceutically acceptable salt thereof, and a pharmaceutically acceptable carrier, diluent, or excipient.

The specific dose administered is determined by the particular circumstances surrounding each situation. These circumstances include, the route of administration, the prior medical history of the patient, the pathological condition or symptom being treated, the severity of the condition/symptom being treated, and the age and sex of the recipient. However, it will be understood that the therapeutic dosage administered will be determined by the physician in the light of the relevant circumstances, or by the veterinarian for non-human recipients.

Generally, an effective minimum daily dose of a compound of formula I is about 10 to 200 mg per day. Typically, an effective maximum dose is about 200 to 1000 mg per day. The exact dose may be determined, in accordance with the standard practice in the medical arts of "dose titrating" the recipient; that is, initially administering a low dose of the compound, and gradually increasing the dose until the desired therapeutic effect is observed.

The pharmaceutical compositions of the present invention may be adapted for these various routes and may be administered to the patient, for example, in the form of tablets, capsules, cachets, papers, lozenges, wafers, elixirs, ointments, transdermal patches, aerosols, inhalants, suppositories, solutions, and suspensions. The total active ingredients in such composition comprises from 0.1% to 99.9% by weight of the formulation (see *Remington's Pharmaceutical Sciences,* 18th Edition, Mack Publishing Co. (1990) for a general discussion of formulations, drug delivery methods, etc).

Examples

The following examples are only illustrative of the preparation protocols and Applicants' ability to prepare compounds of the present invention based on the schemes presented and/or known modifications thereof. The examples are not intended to be exclusive or exhaustive of compounds made or obtainable. The abbreviations used herein are defined according to Aldrichimica Acta, Vol 17, No. 1, 1984 and are generally known to one of skill in the art or may be readily ascertained with minimal effort. Other abbreviations used in the experimentals are: N-methyl-2-pyrrolidinone (NMP), methyl t-butyl ether (MTBE), and room temperature (RT). The names of the compounds of the present invention are provided by ChemDraw Ultra®, version 7.0.1. Salts are named as the free base plus the conjugate acid.

Preparation 1

2-Thiophene-3-yl-ethylamine hydrochloride

Slowly add borane methyl sulfide complex (30.4 mL, 304.4 mmol) to a solution of thiophen-3-yl-acetonitrile (25.0 g, 203.0 mmol) in tetrahydrofuran (450 mL). Heat the reaction at reflux for 16 h and then cool to RT. Slowly quench the reaction with methanol (50 mL) until no foaming is observed. To this mixture slowly add methanol (100 mL) which is saturated with hydrogen chloride. Stir the mixture at RT for 20 min before concentrating in vacuo. Add methanol (100 mL) to the mixture and concentrate in vacuo. Suspend the resulting solid in diethyl ether (200 mL) and filter to afford 31.1 g (94%) of the crude title compound. MS/ES m/z 128.3 $[M+H]^+$.

Preparation 2

(2-Thiophen-3-yl-ethyl)-carbamic acid ethyl ester

Add diisopropylethylamine (54.0 g, 418.0 mmol) to a suspension of 2-thiophene-3-yl-ethylamine hydrochloride in dichloromethane (400 mL) and stir the mixture for 40 min at RT. Cool the mixture to 0° C. and add dropwise ethyl chloroformate (22.7 g, 209.0 mmol) over 15 min. After the addition is complete, stir the reaction for 1 h at 0° C. Wash with 10% sodium bisulfate (500 mL). Extract the aqueous portion with dichloromethane (2×100 mL) and dry the combined organic portions over $Na_2SO_4$, filter and concentrate in vacuo. Purify the resulting residue by silica gel chromatography, using an eluent of 100% dichloromethane to give 22.6 g (60%) of the title compound. MS/ES m/z 200.3 $[M+H]^+$.

Preparation 3

5,6-Dihydro-4H-thieno[2,3-c]pyridin-7-one

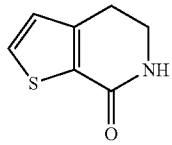

Prepare the title compound by essentially following procedures as found in Aparajithan, K.; Thompson, A. C.; Sam, J. *J. Heterocyclic. Chem.* 1966, 3, 466. Dissolve 4,5-dihydro-cyclopenta[b]thiophen-6-one (Bonini, B. F.; et. al. *Eur. J. Org. Chem.* 2004, 4442 and references cited therein) (0.658 g, 4.77 mmol) in MeOH (50 mL), and add hydroxylamine hydrochloride (0.365 g, 5.25 mmol) and NaOAc (2.35 g, 28.62 mmol). Stir the reaction at RT overnight. Remove the organic solvent in vacuo, and treat the residue with EtOAc (60 mL). Filter through silica gel, wash with EtOAc, and concentrate. Treat the residue with PPA (30 g), heating to 130° C. in an oil bath and with occasional stirring over 30 min. Allow the reaction to cool to RT and pour into ice water (100 mL). Extract with $CH_2Cl_2$ (3×150 mL). Wash the combined organic layers with 0.1 M NaOH (100 mL), dry over $Na_2SO_4$ and concentrate. Purify the material by chromatography, eluting with 75% EtOAc/hexanes to give 0.521 g (71%) of the title compound. MS/ES m/z 154.1 [M+H]+.

Alternate Procedure: 5,6-Dihydro-4H-thieno[2,3-c]pyridin-7-one

Add phosphorus pentoxide (32.1 g, 225.8 mmol) to a solution of 2-thiophen-3-yl-ethyl)-carbamic acid ethyl ester (22.5 g, 112.9 mmol) in phosphorus oxychloride (167 ml) and heat the reaction at 110° C. for 3 h 45 min. Cool the mixture to RT and concentrate in vacuo. Dissolve the residue in dichloromethane (50 mL) and pour into 300 g of ice. Adjust the mixture to pH=7 with 5N sodium hydroxide and extract with dichloromethane (4×100 mL). Dry the combined organic portions ($Na_2SO_4$), filter, and concentrate in vacuo. Purify the resulting residue by silica gel chromatography, eluting with 0% to 70% ethyl acetate/hexane to afford 8.38 g (48%) of the title compound. MS/ES m/z 154.3 [M+H]+.

Preparation 4

2-Bromo-5,6-dihydro-4H-thieno[2,3-c]pyridin-7-one

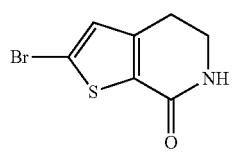

Dissolve 5,6-dihydro-4H-thieno[2,3-c]pyridin-7-one (4.80 g, 31.37 mmol) in HOAc (40 mL) and water (30 mL). Cool to 0° C. and add $Br_2$ (1.8 mL, 34.51 mmol) dropwise. Stir the reaction at 0° C. for 1 h. Dilute the reaction mixture with water (100 mL) and extract with EtOAc (3×100 mL). Wash the combined organic layers with 5% $Na_2SO_3$ (2×50 mL), saturated $NaHCO_3$ (2×100 mL), dry over $Na_2SO_4$, filter and concentrate to give 6.20 g (85%) of the title compound. MS/ES m/z ($^{81}Br$) 233.9 [M+H]+.

Preparation 5

2-Bromo-6H-thieno[2,3-c]pyridin-7-one

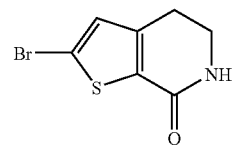

Suspend (E)-3-(5-bromo-thiophen-3-yl)-acrylic acid (Gronowitz, S.; Ander, I. *Chemica Scripta* 1980, 15, 145) (2.04 g, 8.79 mmol) in $CH_2Cl_2$ (30 mL). Treat with oxalyl chloride (1.5 mL, 17.58 mmol) followed by the addition of DMF (3 drops). Stir the reaction at RT for 30 min to obtain a clear solution and continue stirring for 1.5 h. Remove the excess reagent and solvent in vacuo. Dissolve the resulting residue in 1,4-dioxane (10 mL), place in an addition funnel, and add dropwise to a solution of $NaN_3$ (1.8 g, 26.37 mmol) in water (10 mL) and acetone (10 mL) at 0° C. During the addition, maintain the internal temperature below 5° C. Stir the mixture at 0° C. for 1 h. Dilute with water (15 mL), and extract with EtOAc (3×30 mL). Combine the organic layers and concentrate in vacuo without heating. Dissolve the resulting residue in EtOAc (50 mL), and wash with water (30 mL) and brine (20 mL). Dry over $Na_2SO_4$, filter, and concentrate in vacuo without heat to give the crude acyl azide intermediate.

Dissolve the crude acyl azide in 1,4-dioxane (10 mL) and place in an addition funnel which is attached to a flask containing Dowtherm A® (15 mL) and a Dean-Stark trap with a condenser. Heat the Dowtherm A® mixture to 230° C., and add the acyl azide solution dropwise. The internal temperature of the reaction drops to 160° C. during the addition and raises to 230° C. afterwards. Collect the low boiling solvent in the Dean-Stark trap. Stir the reaction at 230° C. for 1 h. Cool to RT and dilute with hexane (40 mL). Collect the precipitate by filtration and wash with hexanes (2×20 mL) to give 1.838 g (91%) of the title compound. $^1$H NMR (DMSO-d6) δ 6.64 (d, 1H, J=6.8 Hz), 7.29 (d, 1H, J=6.8 Hz), 7.57 (s, 1H), 11.64 (bs, 1H). MS/ES m/z ($^{81}Br$) 229.8 [M−H]−.

Preparation 6

5-Chloro-thiophene-2-carboxylic acid (2,2-diethoxyethyl) amide

Add 5-chlorothiophene-2-carboxylic acid (100 g, 0.60 mol) and dichloromethane (1000 mL) to a 3 L three-necked round bottom flask equipped with an overhead stirrer, nitrogen inlet/outlet, addition funnel, and thermocouple. Stir the resulting solution under nitrogen while cooling to 4° C. Add via addition funnel 2,2-diethyoxyethylamine (88.5 ml, 0.60 mol) in dichloromethane (35 mL) over 12 min. Add 1-(3-dimethylaminopropyl)-3-ethylcarbodiimide hydrochloride (123 g, 0.64 mol) to the chilled mixture. Add additional dichloromethane (165 mL) and stir the reaction mixture for 22 h at RT. Quench the reaction with water (1000 mL) and separate the resulting layers. Back extract the aqueous layer with dichloromethane (500 mL) and combine the organic layers. Dry over sodium sulfate and purify through a silica gel bed eluting with dichloromethane followed by a mixture of 1% MeOH in dichloromethane and then a mixture of 10% MeOH in dichloromethane to afford 108 g (65%) of the title compound as a white solid. $^1$H NMR (500 MHz, CDCl$_3$): δ 1.19 (t, J=7.5 Hz, 6H), 3.48-3.57 (m, 4H), 3.68-3.74 (m, 2H), 3.68-3.74 (m, 2H), 6.37 (bs, 1H), 6.85 (d, J=3.5 Hz, 1H), 7.26 (d, J=3.5 Hz, 1H).

Preparation 7

5-(4-chlorophenyl)-thiophene-2-carboxylic acid (2,2-diethyoxyethyl) amide

Add 5-chloro-thiophene-2-carboxylic acid (2,2-diethoxyethyl) amide (50.15 g, 0.18 mol), 4-chlorophenylboronic acid (29.84 g, 0.18 mol), potassium carbonate (50 g, 0.36 mol), [1,3-bis(2,6-diisopropylphenyl)imidazol-2-ylidene)(3-chloropyridyl)]palladium (II) dichloride (4.40 g, 0.006 mol), and EtOH (1000 mL) to a 2 L three-necked round bottom flask equipped with a overhead stirrer, reflux condenser, nitrogen inlet/outlet, addition funnel, and thermocouple. Heat the resulting slurry for 35 min, then add activated carbon (5.8 g) and heat for an additional 30 min. Filter the resulting slurry through glass microfibre filter and rinse solids with EtOH (500 mL). Remove solvent from the filtrate under reduced pressure until 15-20% solvent remains. To this filtrate, add water (1300 mL) and stir the resulting slurry at room temperature for 1 h, then at 0-5° C. for 0.5 h. Filter the slurry, rinse the solids with water (1000 mL), and dry to afford 66 g of crude 5-(4-chlorophenyl)-thiophene-2-carboxylic acid (2,2-diethyoxyethyl) amide. Reflux the crude 5-(4-chlorophenyl)-thiophene-2-carboxylic acid (2,2-diethyoxyethyl) amide in heptane (1625 mL) for 1 h, then filter through a glass microfibre filter. Transfer the filtrate to a round bottom flask and remove solvent until 725 mL of solvent remained. Stir the mixture under chilled conditions for 40 minutes. Filter the resulting slurry, rinse with heptane (100 mL), and dry to afford 41 g (64%) as a white solid. $^1$H NMR (500 MHz, CDCl$_3$): δ 1.25 (t, J=7.0 Hz, 6H), 3.57-3.62 (m, 4H), 3.73-3.79 (m, 2H), 4.62 (t, J=5.5 Hz, 1H), 6.20 (bs, 1H), 7.24 (d, J=4.5 Hz, 1H), 7.38 (d, J=9.0 Hz, 2H), 7.45 (d, J=4.5 Hz, 1H), 7.54 (d, J=9.0 Hz, 2H).

Preparation 8

5-(4-Chlorophenyl)-thiophene-2-carboxylic acid (2-oxoethyl) amide

Add water (21 mL) followed by trifluoroacetic acid (100 g) to a 250 mL three-necked round bottom flask equipped with an overhead stirrer, nitrogen inlet/outlet, and thermocouple. To the stirring TFA solution, add 5-(4-chlorophenyl)-thiophene-2-carboxylic acid (2,2-diethyoxyethyl) amide (25 g, 0.07 mol) in one portion. Stir the reaction mixture for 4 h, pour onto ice/water (1200 mL), and stir for 1.25 h. Filter the resulting slurry and rinse the solid with water (500 mL) and heptane (500 mL), and then dry to give 18.65 g (95%) of the title compound as a yellow-white solid. LC-MS/ES m/z ($^{35}$Cl) 278 (M−H)$^-$. $^1$H NMR (500 MHz, CDCl$_3$): δ 4.40 (d, J=4.0 Hz, 2H), 6.69 (bs, 1H), 7.26 (d, J=3.0 Hz, 1H), 7.40 (d, J=9.0 Hz, 2H), 7.53-7.58 (m, 3H), 9.78 (s, 1H).

Preparation 9

2-(4-Methoxy-phenyl)-5,6-dihydro-4H-thieno[2,3-c]pyridin-7-one

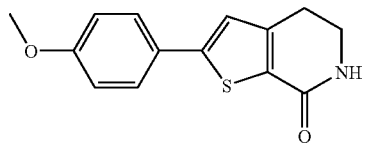

Combine 2-bromo-5,6-dihydro-4H-thieno[2,3-c]pyridin-7-one (1.024 g, 4.42 mmol), 4-methoxyphenyl boronic acid (0.671 g, 4.42 mmol), Na$_2$CO$_3$ (0.94 g, 8.83 mmol), in water (10 mL), dimethoxyethane (75 mL) and CH$_3$OH (50 mL). Purge with nitrogen for 5 min. Add Pd(PPh$_3$)$_4$ (0.153 g, 0.1325 mmol) and reflux the resulting mixture overnight. Cool the reaction to RT and dilute with water (100 mL). Extract with EtOAc (3×100 L), and concentrate. Treat the residue with EtOAc (40 mL), collect the solid and wash with EtOAc (20 mL) and Et$_2$O (2×20 mL) to give the title compound (0.950 g). Concentrate the filtrate and purify the resulting residue by chromatography to give additional product (0.140 g). The overall yield is 1.090 g (95%). MS/ES m/z 260.0 [M+H]$^+$.

Preparation 10

2-(4-Fluoro-phenyl)-5,6-dihydro-4H-thieno[2,3-c]pyridine-7-one

Add tetrakis(triphenylphosphine) palladium(0) (0.075 g, 0.065 mmol) to a degassed solution of 2-bromo-5,6-dihydro-4H-thieno[2,3-c]pyridin-7-one (0.5 g, 2.15 mmol), 4-fluorophenylboronic acid (0.30 g, 2.15 mmol), and sodium carbonate (0.46 g, 4.30 mmol) in N,N-dimethylformamide (21 mL), methanol (5 mL) and water (1 mL). Heat the reaction at 90° C. for 16 h. Allow the reaction to cool to RT and pour into water (75 mL). Filter the resulting solid and dry in vacuo at 80° C. to give 0.40 g (75%) of the title compound. MS/ES m/z 248.0 [M+H]$^+$.

Prepare the intermediates in the table below by following the procedures of the Suzuki coupling essentially as described in Preparation 9 or Preparation 10 using the appropriate arylboronic acid and 2-bromo-5,6-dihydro-4H-thieno[2,3-c]pyridin-7-one or 2-bromo-6H-thieno[2,3-c]pyridin-7-one.

| Prep | Chemical Name | MS (m/z) |
| --- | --- | --- |
| 11 | 2-(4-Chloro-phenyl)-5,6-dihydro-4H-thieno[2,3-c]pyridin-7-one | ($^{35}$Cl) 264.8 [M + H]$^+$ |
| 12 | 2-(4-Trifluoromethoxy-phenyl)-5,6-dihydro-4H-thieno[2,3-c]pyridine-7-one | 314.0 [M + H]$^+$ |
| 13 | 2-(2-Fluoro-4-methoxy-phenyl)-5,6-dihydro-4H-thieno[2,3-c]pyridin-7-one | 278.0 [M + H]$^+$ |

-continued

| Prep | Chemical Name | MS (m/z) |
|---|---|---|
| 14 | 2-(4-Methoxy-phenyl)-5,6-dihydro-4H-thieno[2,3-c]pyridin-7-one | 260.0 [M + H]+ |
| 15 | 2-(3-Fluoro-4-methoxy-phenyl)-5,6-dihydro-4H-thieno[2,3-c]pyridin-7-one | 278.0 [M + H]+ |
| 16 | 2-(4-Cyclopropoxy-phenyl)-5,6-dihydro-4H-thieno[2,3-c]pyridin-7-one | 286.0 [M + H]+ |
| 17 | 2-(3,4-Difluoro-phenyl)-5,6-dihydro-4H-thieno[2,3-c]pyridin-7-one | 266.0 [M + H]+ |
| 18 | 2-(2,4-Difluoro-phenyl)-5,6-dihydro-4H-thieno[2,3-c]pyridin-7-one | 266.0 [M + H]+ |
| 19 | 2-(3,5-Difluoro-phenyl)-5,6-dihydro-4H-thieno[2,3-c]pyridin-7-one | 266.0 [M + H]+ |
| 20 | 2-(4-Trifluoromethyl-phenyl)-5,6-dihydro-4H-thieno[2,3-c]pyridin-7-one | 298.0 [M + H]+ |
| 21 | 2-(4-Trifluoromethoxy-phenyl)-6H-thieno[2,3-c]pyridin-7-one | 312 [M + H]+ |
| 22 | 2-(3-Fluoro-4-methoxy-phenyl)-6H-thieno[2,3-c]pyridin-7-one | 276.0 [M + H]+ |
| 23 | 2-(2-Fluoro-4-methoxy-phenyl)-6H-thieno[2,3-c]pyridin-7-one | 276 [M + H]+ |
| 24 | 2-(4-Fluoro-phenyl)-6H-thieno[2,3-c]pyridin-7-one | 246 [M + H]+ |
| 25 | 2-(3,4-Difluoro-phenyl)-6H-thieno[2,3-c]pyridin-7-one | 264.2 [M + H]+ |
| 26 | 2-(3,4-Dimethoxy-phenyl)-6H-thieno[2,3-c]pyridin-7-one | 288.2 [M + H]+ |
| 27 | 2-(4-Cyclopropoxy-phenyl)-6H-thieno[2,3-c]pyridin-7-one | 284.0 [M + H]+ |
| 28 | 2-(2,4-Difluoro-phenyl)-6H-thieno[2,3-c]pyridin-7-one | 264.0 [M + H]+ |
| 29 | 2-(4-Chloro-phenyl)-6H-thieno[2,3-c]pyridin-7-one | (35Cl) 262.0 [M + H]+ |

Preparation 29, Alternate Prep

Add trifluoromethane sulfonic acid (3 mL, 0.03 mol) and 5-(4-chlorophenyl)-thiophene-2-carboxylic acid (2-oxoethyl) amide (1 g, 0.004 mol) to a 25 mL three-necked round bottom flask equipped with a stir bar, Dean-Stark trap, nitrogen inlet/outlet, and thermocouple. Heat the reaction mixture to 95° C. for 2 h, then cool to 40° C., and pour onto cold water (20 mL, 1.11 mol). Stir the mixture for 10 min. Filter the resulting slurry and rinse the solids with water (100 mL). Dry to afford crude 2-(4-chlorophenyl)-6H-thieno[2,3-c]pyridine-7-one (0.95 g, 0.004 mol) as a brown solid. LC-MS/ES m/z ($^{35}$Cl) 262 [M+H]+.

Preparation 30

(5'-Bromo-3,4,5,6-tetrahydro-2H-[1,2']bipyridinyl-4-yl)-dimethyl-amine

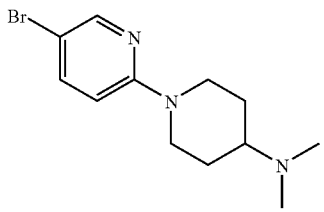

Mix 5-bromo-2-fluoro-pyridine (1.00 g, 5.68 mmol) and N,N-dimethyl-piperidin-4-yl-amine (1.50 g, 11.70 mmol) together and heat to 80° C. for 64 h. Partition the reaction between $CH_2Cl_2$ (5 mL) and 1N NaOH (8 mL). Collect the organic phase and extract the aqueous phase with additional $CH_2Cl_2$ (2×20 mL). Combine the organic solutions, then dry, filter, and concentrate. Purify the crude material by flash chromatography using an eluent of 5% MeOH (2N $NH_3$)/$CH_2Cl_2$ to give 1.49 g (92%) of the title compound as a white solid. $^1$H NMR (CDCl$_3$) δ 1.46 (dq, 2H, J=4.0, 11.8 Hz), 1.86 (br d, 2H, J=12.8 Hz), 2.26 (s, 6H), 2.32 (m, 1H), 2.80 (dt, 2H, J=2.7, 12.8 Hz), 4.23 (br d, 2H, J=13.2 Hz), 6.53 (d, 1H, J=8.9 Hz), 7.46 (dd, 1H, J=2.8, 9.0 Hz), 8.13 (d, 1H, J=2.6 Hz).

Prepare the intermediates in the table below by following the procedure essentially as described in Preparation 30 using 5-bromo-2-fluoro-pyridine and the appropriate amine or alcohol.

| Prep | Chemical Name | NMR or MS/ES m/z |
|---|---|---|
| 31 | 5'-Bromo-3,4,5,6-tetrahydro-2H-[1,2']bipyridinyl-4-ol | $^1$H NMR (CDCl$_3$) δ 1.54 (m, 1H), 1.57 (m, 2H), 1.94 (m, 2H), 3.15 (dt, 2H, J = 2.9, 9.4 Hz), 3.91 (m, 1H), 3.98 (m, 2H), 6.56 (d, 1H, J = 8.8 Hz), 7.46 (dd, 1H, J = 2.8, 9.3 Hz), 8.16 (d, 1H, J = 2.4 Hz) |
| 32 | (R)-3-(5-Bromo-pyridin-2-yloxy)-pyrrolidine-1-carboxylic acid tert-butyl ester | ($^{81}$Br) 289.0 [M − tBu + H]+ |

| Prep | Chemical Name | NMR or MS/ES m/z |
|---|---|---|
| 33 | (S)-3-(5-Bromo-pyridin-2-yloxy)-pyrrolidine-1-carboxylic acid tert-butyl ester | ($^{81}$Br) 289.0 [M − tBu + H]$^+$ |
| 34 | (S)-3-(5-Bromo-pyridin-2-yloxy)-piperidine-1-carboxylic acid tert-butyl ester | ($^{79}$Br) 357.0 [M + H]$^+$ |
| 35 | (R)-3-(5-Bromo-pyridin-2-yloxy)-piperidine-1-carboxylic acid tert-butyl ester | ($^{79}$Br) 357.0 [M + H]$^+$ |
| 36 | 4-(5-Bromo-pyridin-2-yloxy)-piperidine-1-carboxylic acid tert-butyl ester | ($^{79}$Br) 301.0 [M − tBu + H]$^+$ |

Preparation 37

[(S)-1-(5-Bromo-pyridin-2-yl)-pyrrolidin-3-yl]-dimethyl-amine

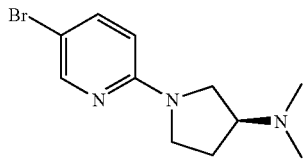

Heat a mixture of dimethyl-pyrrolidin-3-(S)-yl-amine (3.0 g, 26.3 mmoL), 5-bromo-2-fluoro-pyridine (4.62 g, 26.3 mmol), potassium carbonate (7.98 g, 57.8 mmol) in acetonitrile (91 mL) at 80° C. overnight. Allow the mixture to cool to RT, filter with CH$_2$Cl$_2$, and concentrate. Purify the crude material by flash chromatograph, eluting with 5% MeOH (2N NH$_3$)/CH$_2$Cl$_2$ to give 3.55 g (50%) of the title compound. LC-MS/ES m/z ($^{81}$Br) 272.3 [M+H]$^+$.

Prepare the intermediates in the table below by following the procedure essentially as described for Preparation 37 using the appropriate amine and 5-bromo-2-fluoro-pyridine.

| Prep | Chemical Name | LC-MS/ES m/z |
|---|---|---|
| 38 | [(R)-1-(5-Bromo-pyridin-2-yl)-pyrrolidin-3-yl]-dimethyl-amine | ($^{81}$Br) 272.3 [M + H]$^+$ |
| 39 | 1-(5-Bromo-pyridin-2-yl)-4-methyl-[1,4]diazepane | ($^{81}$Br) 272.0 [M + H]$^+$ |

Preparation 40

(±)-3-(Methoxy-methyl-carbamoyl)-pyrrolidine-1-carboxylic acid tert-butyl ester

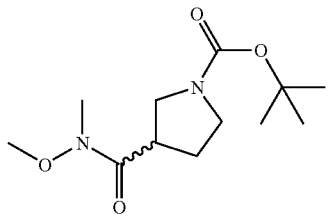

Add in one portion 1,1'-carbonyldiimidazole (8.3 g, 51 mmol) to a solution of pyrrolidine-1,3-dicarboxylic acid 1-tert-butyl ester (10.0 g, 46.5 mmol) in dichloromethane (155 mL) at RT. Allow the mixture to stir for 15 min. Add slowly N,O-dimethylhydroxylamine hydrochloride (5.4 g, 55.8 mmol). Stir the reaction mixture at RT overnight. Dilute the mixture with dichloromethane (200 mL), wash with water (2×300 mL), brine (200 mL), dry over Na$_2$SO$_4$, filter, and concentrate. Purify the crude material by flash chromatograph and elute with 50-100% ethylacetate/hexane to give 10.8 g (90%) of the title compound. LC-MS/ES m/z 203.0 [M-tert-Bu+H]$^+$.

Preparation 41

(±)-2-(Methoxy-methyl-carbamoyl)-morpholine-4-carboxylic acid tert-butyl ester

Prepare the title compound by following the procedure essentially as described for Preparation 40, using morpholine-2,4-dicarboxylic acid 4-tert-butyl ester as the starting material. LC-MS/ES 219 [M-tert-Bu+H]$^+$.

Preparation 42

(±)-3-(5-Bromo-pyridine-2-carbonyl)-pyrrolidine-1-carboxylic acid tert-butyl ester Prepare the title compound as found in J. Org. Chem. 2004, 69, 250-262 and Tetrahedron Letter 2000, 41, 4335-4338.

Add dropwise n-BuLi (3.2 mL, 5.1 mmol) to an suspension of 2,5-dibromopyridine (1.0 g, 4.2 mmol) in dry toluene (50 mL) at −80° C. under nitrogen. Allow the mixture to stir at −80° C. for 2 h. Slowly add a solution of 3-(methoxy-methyl-carbamoyl)-pyrrolidine-1-carboxylic acid tert-butyl ester (1.4 g, 5.5 mmol) in dry toluene (10 mL). Allow the reaction mixture to stir for 1 h at −78° C., then warm to −10° C. Quench the mixture with saturated NH$_4$Cl (1 mL) and warm to RT. Separate the organic layer and concentrate. Purify the crude material by flash chromatography, eluting with 10-20% ethylacetate/hexane to give 0.61 g (43%) of the title compound. LC-MS/ES m/z ($^{79}$Br) 299 [M-tert-Bu+H]$^+$.

Preparation 43

(±)-2-(5-Bromo-pyridine-2-carbonyl)-morpholine-4-carboxylic acid tert-butyl ester Prepare the title compound by following the procedure essentially as described for Preparation 42, using 2-(methoxy-methyl-carbamoyl)-morpholine-4-carboxylic acid tert-butyl ester as the starting material. LC-MS/ES ($^{81}$Br) 317.0 [M-t-Bu+H]$^+$.

Preparation 44

(±)-(5-Bromo-pyridin-2-yl)-pyrrolidin-3-yl-methanone

Stir a solution of 3-(5-bromo-pyridine-2-carbonyl)-pyrrolidine-1-carboxylic acid tert-butyl ester (0.65 g, 1.8 mmol) in 4 M HCl in dioxane (3.7 mL) at 0° C. for 1 h. Concentrate the reaction mixture, dilute the mixture with $CH_2Cl_2$, wash with 5 N NaOH (15 mL), and back-extract the aqueous with $CH_2Cl_2$. Wash the combined organic layer with brine, dry over $Na_2SO_4$, filter and concentrate. Purify the crude material by flash chromatography, eluting with 10% MeOH (2N $NH_3$)/$CH_2Cl_2$ to give 0.4 g (85%) of the title compound. LC-MS/ES m/z ($^{81}Br$) 257.0 [M+H]$^+$.

Preparation 45

(±)-(5-Bromo-pyridin-2-yl)-morpholin-2-yl-methanone

Prepare the title compound by following the procedure essentially as described for Preparation 44, using 2-(5-bromo-pyridine-2-carbonyl)-morpholine-4-carboxylic acid tert-butyl ester as the starting material. GC ($^{81}Br$) 272 [M$^+$].

Preparation 46

(±)-(5-Bromo-pyridin-2-yl)-(1-methyl-pyrrolidin-3-yl)-methanone

To a solution of (5-bromo-pyridin-2-yl)-pyrrolidin-3-yl-methanone (0.35 g, 1.35 mmol) in methanol (68 mL), add acetic acid (0.15 mL, 2.7 mmol), and formaldehyde (0.33 g, 4.1 mmol, 37% aqueous solution). After 15 min, add sodium triacetoxyborohydride (0.86 g, 4.1 mmol) and allow the mixture to stir at RT for 1 h. Concentrate the reaction mixture, dissolve in $CH_2Cl_2$, and wash with saturated $NaHCO_3$. Back-extract the aqueous with $CH_2Cl_2$. Wash the combined organic layer with water, dry over $Na_2SO_4$, filter, and concentrate. Purify the crude material by flash chromatography, eluting with 5-10% MeOH (2N $NH_3$)/$CH_2Cl_2$ to give 0.17 g (47%) of the title compound. LC-MS/ES m/z ($^{79}Br$) 270 [M+H]$^+$.

Preparation 47

(±)-(5-Bromo-pyridin-2-yl)-(4-methyl-morpholin-2-yl)-methanone

Prepare the title compound by following the procedure essentially as described for Preparation 46, using (5-bromo-pyridin-2-yl)-morpholin-2-yl-methanone as the starting material. GC-MS ($^{81}Br$) 286 [M$^+$].

Preparation 48

[(R)-1-(5-Bromo-3-methyl-pyridin-2-yl)-pyrrolidin-3-yl]-dimethyl-amine

Combine 2,5-dibromo-3-methyl-pyridine (2.00 g, 7.97 mmol) with dimethyl-(R)-pyrrolidin-3-yl-amine (2.40 g, 20.72 mmol) and p-toluenesulfonic acid monohydrate (0.39 g, 2.07 mmol) in a sealed tube and heat at 100° C. overnight. Dilute with EtOAc (100 mL), wash with saturated $NaHCO_3$ (3×40 mL), dry over $Na_2SO_4$, filter and concentrate. Purify the crude material by chromatography, eluting with 2% $NH_3H_2O$ in 1:1 $CH_3OH$:EtOAc to give 2.09 g (99%) of the title compound. LC-MS/ES m/z ($^{79}Br$) 284.3 [M+H]$^+$.

Preparation 49

[(S)-1-(5-Bromo-pyridin-2-yl)-pyrrolidin-3-yl]-carbamic acid tert-butyl ester

Dissolve 5-bromo-2-fluoro-pyridine (5.20 g, 29.53 mmol), and (S)-pyrrolidin-3-yl-carbamic acid tert-butyl ester (5.50 g, 29.53 mmol) in acetonitrile (100 mL) and reflux with $K_2CO_3$ (8.90 g, 64.96 mmol) for 3 h. Filter the reaction mixture and wash with EtOAc (100 mL). Concentrate the filtrate and purify the resulting crude material by silica gel chromatography, eluting with 40% EtOAc/hexanes to give 2.76 g (27%) of the title compound. LC-MS/ES m/z ($^{81}Br$) 344.3 [M+H]$^+$.

Preparation 50

[(R)-1-(5-Bromo-pyridin-2-yl)-pyrrolidin-3-yl]-carbamic acid tert-butyl ester

Prepare the title compound by essentially following the procedure as described for Preparation 49, using 5-bromo-2-fluoro-pyridine (6.26 g, 35.61 mmol), and (R)-pyrrolidin-3-yl-carbamic acid tert-butyl ester (6.632 g, 35.61 mmol) to give 3.77 g (30%) of the title compound. LC-MS/ES m/z ($^{81}Br$) 344.3 [M+H]$^+$.

Preparation 51

(R)-1-(5-Bromo-pyridin-2-yl)-pyrrolidin-3-ylamine

Dissolve [(R)-1-(5-bromo-pyridin-2-yl)-pyrrolidin-3-yl]-carbamic acid tert-butyl ester (9.17 g, 26.9 mmol) in $CH_2Cl_2$ (45 mL), add TFA (10 mL) and stir at RT overnight. Remove the excess reagent in vacuo. Dilute the residue with $CH_2Cl_2$ (100 mL) and wash with 1.0 M NaOH (100 mL). Extract the aqueous layer with $CH_2Cl_2$ (3×100 mL). Combine the organic layers, dry with $Na_2SO_4$, filter and concentrate to give 6.03 g (93%) of the title compound. MS/ES m/z ($^{79}Br$) 242 [M+H]$^+$.

Preparation 52

(S)-1-(5-Bromo-pyridin-2-yl)-pyrrolidin-3-ylamine

Prepare the title compound by essentially following the procedure as described in Preparation 51 using [(S)-1-(5-bromo-pyridin-2-yl)-pyrrolidin-3-yl]-carbamic acid tert-butyl ester as the starting material. MS/ES m/z ($^{79}Br$) 242 [M+H]$^+$.

Preparation 53

(S)-1-(5-Bromo-pyridin-2-yl)-pyrrolidin-3-ol

Heat 5-bromo-2-fluoro-pyridine (10.33 g, 57.39 mmol) in THF (50 mL) with (S)-3-hydroxypyrrolidine (5.00 g, 57.39 mmol) and $Et_3N$ (9.2 mL, 68.87 mmol) in a microwave reactor at 120° C. for 45 min. Dilute with EtOAc (150 mL), and wash with saturated $NaHCO_3$ (2×50 mL) and water (100 mL). Dry with $Na_2SO_4$, filter, and concentrate. Purify the crude material by chromatography, eluting with 100% EtOAc to give 10.13 g (72%) of the title compound. MS/ES m/z ($^{79}Br$) 244.0 [M+H]$^+$.

Preparation 54

Methanesulfonic acid (R)-1-(5-bromo-pyridin-2-yl)-pyrrolidin-3-yl ester

Dissolve (R)-1-(5-bromo-pyridin-2-yl)-pyrrolidin-3-ol (6.8 g, 27.64 mmol), (prepare according to Stenkamp, D. et al WO 2005103032) in $CH_2Cl_2$ (50 mL), and cool to 0° C. Treat the mixture with $Et_3N$ (5.0 mL, 35.93 mmol), followed by MsCl (2.4 mL, 30.4 mmol). Stir the mixture at 0° C. for 30 min and then at RT for 1 h. Dilute with $CH_2Cl_2$ (100 mL), and wash with $H_2O$ (100 mL), and brine (100 mL). Dry with $Na_2SO_4$, filter, and concentrate. Purify the crude material by chromatography, eluting with 50-70% EtOAc/hexane, to give 8.86 g (97%) of the title compound. MS/ES m/z ($^{79}Br$) 321.0 $[M+H]^+$.

Preparation 55

Methanesulfonic acid (S)-1-(5-bromo-pyridin-2-yl)-pyrrolidin-3-yl ester

Prepare the title compound by essentially following the procedure as described in Preparation 54, from (S)-1-(5-bromo-pyridin-2-yl)-pyrrolidin-3-ol (10.13 g, 41.19 mmol) to give 12.54 g (94%) of the title compound. MS/ES m/z ($^{79}Br$) 321.0 $[M+H]^+$.

Preparation 56

(3R,3'S)-1'-(5-Bromo-pyridin-2-yl)-3-fluoro-[1,3']bipyrrolidinyl

Dissolve methanesulfonic acid (R)-1-(5-bromo-pyridin-2-yl)-pyrrolidin-3-yl ester (0.23 g, 0.71 mmol) and (R)-3-fluoro-pyrrolidine hydrochloride (107 mg, 0.85 mmol) in DMF (5 mL) and add $Cs_2CO_3$ (0.69 g, 2.13 mmol). Warm to 70° C. overnight. Dilute with EtOAc (100 mL) and wash with $H_2O$ (3×100 mL). Dry with $Na_2SO_4$, filter, and concentrate. Purify the crude material by chromatography, eluting with 75-100% EtOAc/hexane to give 0.22g (100%) of the title compound. $^1$H-NMR ($CDCl_3$), δ 1.87-2.00 (m, 1H), 2.00-2.09 (m, 1H), 2.18-2.30 (m, 2H), 3.40-3.80 (m, 9H), 5.10-5.28 (m, 1H), 5.34-5.40 (m, 1H), 6.28 (d, J=9.0 Hz, 1H), 7.51 (dd, J=9.0, 2.4 Hz, 1H), 8.18 (d, J=2.4 Hz, 1H).

Prepare the following compound by essentially following the procedures as described in Preparation 56 using the corresponding amine and methanesulfonic acid (S)-1-(5-bromo-pyridin-2-yl)-pyrrolidin-3-yl ester.

| Prep | Chemical Name | 1H-NMR ($CDCl_3$) |
|---|---|---|
| 57 | (3S,3'R)-1'-(5-Bromo-pyridin-2-yl)-3-fluoro-[1,3']bipyrrolidinyl | δ 1.87-2.00 (m, 1H), 2.00-2.09 (m, 2H), 2.18-2.30 (m, 2H), 3.40-3.80 (m, 9H), 5.10-5.28 (m, 1H), 5.34-5.40 (m, 1H), 6.28 (d, J = 9.0 Hz, 1H), 7.51 (dd, J = 9.0, 2.4 Hz, 1H), 8.18 (d, J = 2.4 Hz, 1H). |

Preparation 58

[(R)-1-(5-Bromo-pyridin-2-yl)-pyrrolidin-3-yl]-cyclopropyl-amine

Dissolve methanesulfonic acid (S)-1-(5-bromo-pyridin-2-yl)-pyrrolidin-3-yl ester (3.07 g, 9.48 mmol) and cyclopropylamine (1.7 mL, 23.68 mmol) in THF (20 mL). Microwave the mixture at 130° C. for 6 h. Dilute the mixture with EtOAc (100 mL) and wash with saturated $NaHCO_3$ (25 mL). Dry the organic portion over $Na_2SO_4$, filter, and concentrate. Purify the crude material by chromatography, eluting with a gradient of 75-100% EtOAc/hexane to give 1.638 g (61%) of the title compound. LC-MS/ES m/z ($^{79}Br$) 283.0 $[M+H]^+$.

Preparation 59

N—[(R)-1-(5-Bromo-pyridin-2-yl)-pyrrolidin-3-yl]-2,2-difluoro-acetamide

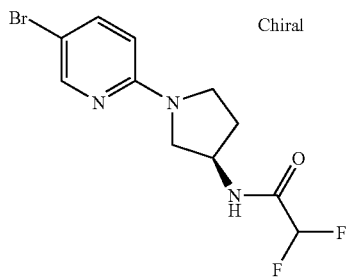

Dissolve [(R)-1-(5-bromo-pyridin-2-yl)-pyrrolidin-3-yl]-carbamic acid tert-butyl ester (4.24 g, 12.43 mmol) in $CH_2Cl_2$ (10 mL) and add TFA (5 mL). Stir at RT for 1 h. Evaporate the excess reagent. Dissolve the resulting crude material in $CH_2Cl_2$ (50 mL) and cool to 0° C. Add difluoroacetic acid (1.78 g, 18.64 mmol), EDCI (3.57 g, 18.64 mmol), HOBt (2.52 g, 18.64 mmol) and $Et_3N$ (5.2 mL, 37.3 mmol). Stir the reaction at 0° C. for 30 min and at RT overnight. Dilute with $CH_2Cl_2$ (100 mL) and wash with 0.1 M NaOH (2×50 mL) and $H_2O$ (100 mL). Dry the solution with $Na_2SO_4$, filter, and concentrate. Purify the crude material, eluting with 100% EtOAc to give 1.98 g (50%) of the title compound. MS/ES m/z ($^{79}Br$) 321.0 $[M+H]^+$.

Prepare the intermediates below by following the procedure as essentially described for Preparation 59, using (R) or (S)-[1-(5-bromo-pyridin-2-yl)-pyrrolidin-3-yl]-carbamic acid tert-butyl. For Preparation 61 use trifluoroacetic anhydride (1 eq) and triethylamine (1.2 eq).

| Prep | Chemical Name | MS/ES m/z |
|---|---|---|
| 60 | N-[(S)-1-(5-Bromo-pyridin-2-yl)-pyrrolidin-3-yl]-2,2-difluoro-acetamide | ($^{79}Br$) 320.0 $[M + H]^+$ |
| 61 | N-[(R)-1-(5-Bromo-pyridin-2-yl)-pyrrolidin-3-yl]-2,2,2-trifluoro-acetamide | ($^{79}Br$) 339.8 $[M + H]^+$ |

Preparation 62

[(R)-1-(5-Bromo-pyridin-2-yl)-pyrrolidin-3-yl]-(2,2-difluoro-ethyl)-amine

Dissolve N—[(R)-1-(5-bromo-pyridin-2-yl)-pyrrolidin-3-yl]-2,2-difluoro-acetamide (1.98 g, 6.19 mmol) in THF (50 mL) and cool to 0° C. Add 1.0 M $BH_3$ THF complex in THF (18.6 mL, 18.6 mmol) dropwise. Stir the mixture at 0° C. for 10 min and then reflux for 4 h. Cool the mixture to 0° C. and quench with $CH_3OH$ (5 mL) and saturated $NH_4Cl$ (20 mL). Stir the mixture at 0° C. for 5 min and at RT for 30 min. Dilute with H$_2$O (50 mL) and extract with EtOAc (2×80 mL). Dry the organic portion with Na$_2$SO$_4$, filter, and concentrate. Purify the crude material by chromatography, eluting with 50-70% EtOAc/hexane to give 1.01 g (50%) of the title compound. MS/ES m/z ($^{79}$Br) 306.0 [M+H]$^+$.

Preparation 63

[(S)-1-(5-Bromo-pyridin-2-yl)-pyrrolidin-3-yl]-(2,2-difluoro-ethyl)-amine

Add via syringe 1M BH$_3$-THF (78 mL, 78 mmol) to a solution of N—[(S)-1-(5-bromo-pyridin-2-yl)-pyrrolidin-3-yl]-2,2-difluoro-acetamide (8.3 g, 25 mmol) in tetrahydrofuran (65 mL) and heat the mixture at reflux overnight. Cool the reaction to 0° C. and slowly quench with 5N NaOH until no gas evolution is observed. Concentrate the material in vacuo to remove THF. Dilute the residue with water (150 mL) and extract with CH$_2$Cl$_2$ (3×150 mL). Dry the combined organics over Na$_2$SO$_4$, filter, and concentrate to dryness. Add sodium triacetoxyborohydride (35.4 g, 167 mmol) to the residue in dichloromethane (75 mL). Add dropwise trifluoroacetic acid (150 mL) with vigorous stirring. After 10 min concentrate the mixture in vacuo and dilute with CH$_2$Cl$_2$ (150 mL). Cool the mixture in an ice bath and slowly basify to pH 9 with 5N NaOH. Stir the basic mixture overnight. Dilute the mixture with water (200 mL) and extract with CH$_2$Cl$_2$ (3×150 mL). Dry the combined organics over Na$_2$SO$_4$, filter, and concentrate to dryness. Purify by chromatography to afford 6.38 g (85%) of the title compound. MS/ES m/z ($^{79}$Br) 306.0 [M+H]$^+$.

Preparation 64

[(R)-1-(5-Bromo-pyridin-2-yl)-pyrrolidin-3-yl]-(2,2,2-trifluoro-ethyl)-amine

Prepare the titled compound by following the procedure as essentially described in Preparation 62, using N—[(R)-1-(5-bromo-pyridin-2-yl)-pyrrolidin-3-yl]-2,2,2-trifluoro-acetamide (1.25g, 3.55 mmol) to give 1.07 g (93%) of the title compound. MS/ES m/z ($^{79}$Br) 324 [M+H]$^+$.

Preparation 65

[(R)-1-(5-Bromo-pyridin-2-yl)-pyrrolidin-3-yl]-dicyclopropyl-amine

Dissolve (R)-1-(5-bromo-pyridin-2-yl)-pyrrolidin-3-ylamine (1.60 g, 6.63 mmol) in CH$_3$OH (915 mL). Add (1-ethoxy-cyclopropoxy)-trimethyl-silane (2.7 mL, 13.49 mmol) and HOAc (1.9 mL, 33.15 mmol) and stir at RT for 3 h. Add NaBH$_3$CN (4.2 g, 66.30 mmol) and reflux overnight. Cool the mixture to 0° C., quench with 2.0 M NaOH (15 mL), and dilute with H$_2$O (100 mL). Extract with EtOAc (3×100 mL). Wash the combined organic layers with 1.0 M NaOH (50 mL), H$_2$O (100 mL), and brine (50 mL). Dry the solution with Na$_2$SO$_4$, filter, and concentrate. Purify the crude material by chromatography, eluting with 0.5% Et$_3$N, 5% CH$_3$OH and 95% CHCl$_3$ to give 1.20 g (56%) of the title compound. MS/ES m/z ($^{79}$Br) 322 [M+H]$^+$.

Preparation 66

N—[(R)-1-(5-Bromo-pyridin-2-yl)-pyrrolidin-3-yl]-2-methoxy-acetamide

Add methoxyacetyl chloride (208 µL, 2.27 mmol) to a 0° C. solution of (R)-1-(5-bromo-pyridin-2-yl)-pyrrolidin-3-ylamine (0.5 g, 2.07 mmol) and triethylamine (317 µL, 2.27 mmol) in dichloromethane (10 mL). Remove the ice bath and stir the reaction overnight. Wash the reaction mixture with 10% aqueous NaHSO$_4$ (20 mL). Separate the organic portion and extract the aqueous portion with dichloromethane (2×10 mL). Dry the combined organics over Na$_2$SO$_4$, filter, and concentrate to dryness. Purify using chromatography (0 to 5% MeOH/CH$_2$Cl$_2$) to afford 525 mg (81%) of the title compound. LC-MS/ES m/z ($^{79}$Br) 314.0 [M+H]$^+$.

Preparation 67

2-[(R)-1-(5-Bromo-pyridin-2-yl)-pyrrolidin-3-ylamino]-ethanol

Add dropwise via an addition funnel a solution of iodine (727 mg, 2.86 mmol) in tetrahydrofuran (5 mL) over 15 min to a mixture of N—[(R)-1-(5-bromo-pyridin-2-yl)-pyrrolidin-3-yl]-2-methoxy-acetamide (500 mg, 1.59 mmol) and sodium borohydride (217 mg, 6.05 mmol) in tetrahydrofuran (5 mL). Heat the colorless mixture at reflux overnight, then cool to room temperature and slowly quench with MeOH until no foaming is observed. Concentrate the material in vacuo. Add 1N NaOH (20 mL) to the residue and extract the mixture with dichloromethane (3×20 mL). Dry the combined organics over Na$_2$SO$_4$, filter, and concentrate to dryness. Purify using chromatography (0 to 10% MeOH/CH$_2$Cl$_2$) to afford 120 mg (26%) of the title compound. LC-MS/ES m/z ($^{79}$Br) 286.2 [M+H]$^+$.

Preparation 68

1-(5-Bromo-pyridin-2-yl)-4-methyl-piperazine

Heat 2-fluoro-5-bromopyridine (2.15 g, 12.22 mmol) with 1-methyl-piperazine (3.4 mL, 30.54 mmol) in THF (10 mL) in a microwave reactor at 120° C. for 45 min. Dilute with EtOAc (60 mL), then wash with NaHCO$_3$ (2×30 mL) and brine (20 mL). Dry with Na$_2$SO$_4$, filter, and concentrate to give 2.01 g (64%) of the title compound. MS/ES m/z ($^{79}$Br) 256 [M+H]$^+$.

Preparation 69

(±)-trans-4'-Hydroxy-[1,3']bipyaolidinyl-1'-carboxylic acid tert-butyl ester

Dissolve 6-oxa-3-aza-bicyclo[3.1.0]hexane-3-carboxylic acid tert-butyl ester (prepare according to Syn. Comm. V26 (8) p 1499, 1996) (1.25 g, 6.75 mmol) in pyrrolidine (8 mL) and water (12 mL). Warm to 50° C. and stir in a sealed vessel for 3 days. Dilute the mixture with saturated sodium bicarbonate and extract three times with dichloromethane. Dry the organics over sodium sulfate, filter, and evaporate. Purify by silica gel chromatography, eluting with 0-15% methanol (2N NH$_3$)/CH$_2$Cl$_2$ to give 1.73 g (100%) of the title compound as a yellow oil. $^1$H NMR(CDCl$_3$) δ 1.43 (s, 9H), 1.77 (m, 4H), 2.08 (bs, 1H), 2.60 (m, 4H), 2.72 (bs, 1H), 3.27 (m, 1H), 3.65 (m, 1H), 4.29 (m, 1H).

Preparation 70

(±)-trans-3-Dimethylamino-4-hydroxy-pyrrolidine-1-carboxylic acid tert-butyl ester Prepare the title compound by essentially following the procedures as described in Preparation 69 to obtain 0.676 g (95%) of a yellow oil. MS/ES m/z 231 [M+H]$^+$.

Preparation 71

(±)-cis-4'-Fluoro-[1,3']bipyrrolidinyl-1'-carboxylic acid tert-butyl ester

Dissolve 4'-hydroxy[1,3']bipyrrolidinyl-1'-carboxylic acid tert-butyl ester (573 mg, 2.24 mmol) in dichloromethane (15 mL) and cool the mixture to −78° C. Add diethylaminosulfur trifluoride (504 mg, 3.13 mmol) dropwise and then allow the mixture to warm to room temperature. Stir the mixture overnight. Evaporate the solution and purify by silica gel chromatography, eluting with 0-3% methanol (2N $NH_3$)/$CH_2Cl_2$ to give 520 mg (89%) of the title compound as a yellow oil. $^1$H NMR(DMSO-$d_6$): δ 1.37 (s, 9H), 1.61-1.67 (m, 4H), 2.43-2.54 (m, 4H), 2.86 (bs, 1H), 3.30-3.41 (m, 1H), 3.45-3.60 (m, 1H), 5.09-5.25 (m, 1H).

Preparation 72

(±)-cis-3-Dimethylamino-4-fluoro-pyrrolidine-1-carboxylic acid tert-butyl ester

Prepare the title compound by essentially following the procedure as described in Preparation 71 to obtain 1.9 g (78%) of product as a yellow oil. $^1$H NMR(DMSO-$d_6$) δ 1.44 (s, 9H), 2.28 (s, 6H), 2.89 (m, 1H), 3.29 (m, 1H), 3.42-3.81 (m, 3H), 5.26-5.35 (m, 1H).

Preparation 73

(±)-trans-[1,3']Bipyrrolidinyl-4'-ol

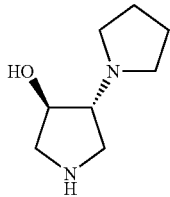

Dissolve 4'-hydroxy-[1,3']bipyrrolidinyl-1'-carboxylic acid tert-butyl ester (751 mg, 2.93 mmol) in dichloromethane (13 mL) and cool the mixture to 0° C. Add trifluoroacetic acid (2.5 mL, 33.1 mmol) and warm the mixture to room temperature for one hour. Remove the volatiles via reduced pressure and then purify by applying to two 10 g SCX cartridges. Wash the material with methanol then elute the material with 2N ammonia in methanol to give 460 mg (99%) of the title compound as a clear oil. $^1$H NMR(DMSO-$d_6$) δ 1.60 (m, 4H), 2.31 (s, 1H), 2.41 (m, 5H), 2.53 (m, 1H), 2.81 (m, 1H), 2.93 (m, 1H), 3.94 (s, 1H).

Prepare the following compounds by deprotection of the corresponding carbamates using trifluoroacetic acid essentially as described in Preparation 73.

| Prep | Chemical Name | $^1$H NMR(DMSO-d6) |
|---|---|---|
| 74 | (±)-cis-4'-Fluoro-[1,3']bipyrrolidinyl | δ 1.75-1.81 (m, 4H), 1.87 (bs, 1H), 2.57 (m, 4H), 2.7-283 (m, 2H), 2.99-3.30 (m, 3H), 4.96-5.13 (m, 1H) |
| 75 | (±)-trans-4-Dimethylamino-pyrrolidin-3-ol | δ 2.47 (s, 6H), 2.84 (d, J = 12.1 Hz, 1H), 2.97 (dd, J = 12.1, 4.5 Hz, 1H), 3.06-3.08 (m, 4H), 4.18 (bs, 1H). |
| 76 | (±)-cis-(4-Fluoro-pyrrolidin-3-yl)-dimethyl-amine | δ 2.13 (s, 6H), 2.38-2.43 (m, 1H), 2.45-2.58 (m, 1H), 2.75-2.98 (m, 2H), 3.02-3.08 (m, 1H), 4.87-5.04 (m, 1H) |

Preparation 77

(±)-trans-1'-(5-Bromo-pyridin-2-yl)-[1,3']bipyrrolidinyl-4'-ol

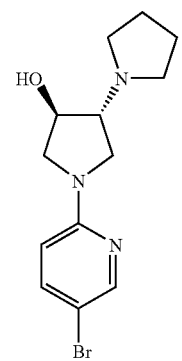

Dissolve [1,3']bipyrrolidinyl-4'-ol (452 mg, 2.89 mmol) in acetonitrile (10 mL) and add 5-bromo-2-fluoro-pyridine (764 mg, 4.34 mmol) and diisopropylethylamine (1.26 mL, 7.23 mmol). Reflux the mixture for 3 days. Dilute the mixture with saturated sodium bicarbonate and extract with dichloromethane (3×). Combine the organic fractions, dry over sodium sulfate, filter, and evaporate. Purify by silica gel chromatography, eluting with 0-7.5% methanol (2N $NH_3$)/$CH_2Cl_2$ to give 610 mg (67%) of the title compound as a yellow foam. MS/ES m/z ($^{79}$Br) 312.0 [M+H]$^+$.

Prepare the following compounds essentially as in Preparation 77 using the 5-bromo-2-fluoro-pyridine and the corresponding pyrrolidines.

| Prep | Chemical Name | MS/ES m/z |
|---|---|---|
| 78 | (±)-trans-1'-(5-Bromo-pyridin-2-yl)-4'-fluoro-[1,3']bipyrrolidinyl | ($^{81}$Br) 315.0 [M$^+$] |
| 79 | (±)-trans-1-(5-Bromo-pyridin-2-yl)-4-dimethylamino-pyrrolidin-3-ol | ($^{81}$Br) 288.0 [M + H]$^+$ |
| 80 | (±)-cis-[1-(5-Bromo-pyridin-2-yl)-4-fluoro-pyrrolidin-3-yl]-dimethyl-amine | ($^{79}$Br) 288.0 [M + H]$^+$ |

Preparation 81

(±)-trans-1-(5-Bromo-pyridin-2-yl)-4-methylamino-pyrrolidin-3-ol

Dissolve 6-oxa-3-aza-bicyclo[3.1.0]hexane-3-carboxylic acid tert-butyl ester (1.50 g, 8.10 mmol) in methylamine (15 mL, 40% solution in water). Warm to 50° C. and stir in a sealed vessel overnight. Dilute the mixture with saturated sodium bicarbonate and extract with dichloromethane (3×). Dry the organics over sodium sulfate, filter, and evaporate. Purify by silica gel chromatography, eluting with 0-10% methanol (2N NH$_3$)/CH$_2$Cl$_2$ to give 1.87 g (97%) of 3-hydroxy-4-methylamino-pyrrolidine-1-carboxylic acid tert-butyl ester as a yellow oil.

Dissolve 3-hydroxy-4-methylamino-pyrrolidine-1-carboxylic acid tert-butyl ester (750 mg, 3.26 mmol) in dichloromethane (20 mL) and cool the mixture to 0° C. Add trifluoroacetic acid (4 mL, 52.9 mmol) and warm the mixture to room temperature for one hour. Remove the volatiles via reduced pressure and then apply to a 10 g SCX cartridge. Wash the material with methanol and then elute the material with 2N ammonia in methanol to give 430 mg (100%) of 4-methylamino-pyrrolidin-3-ol as a clear oil.

Dissolve 4-methylamino-pyrrolidin-3-ol (430 mg, 3.29 mmol) in acetonitrile (10 mL) and add 5-bromo-2-fluoropyridine (868 mg, 4.93 mmol) and diisopropylethylamine (0.688 mL, 3.95 mmol). Reflux the mixture for 3 days. Dilute the mixture with saturated sodium bicarbonate and extract with dichloromethane (3×). Combine the organic fractions, dry over sodium sulfate, filter, and evaporate. Purify by silica gel chromatography, eluting with 0-7.5% methanol in dichloromethane with 2N ammonia to give 352 mg (37%) of the title compound as a yellow foam. MS/ES m/z ($^{79}$Br) 272.0 [M+H]$^+$.

Preparation 82

(±)-trans-1-(5-Bromo-pyridin-2-yl)-4-[(3,4-dimethoxy-benzyl)-methyl-amino]-pyrrolidin-3-ol Dissolve 1-(5-bromo-pyridin-2-yl)-4-methylamino-pyrrolidin-3-ol (0.347 g, 1.28 mmol) in dichloroethane (10 mL) and add veratraldehyde (212 mg, 1.28 mmol), sodium triacetoxyborohydride (405 mg, 1.91 mmol) and acetic acid (125 mL, 2.18 μmol). Stir the mixture at room temperature overnight. Dilute with saturated sodium bicarbonate and extract the mixture with dichloromethane (3×). Dry the combined organic portions over sodium sulfate, filter, and evaporate. Purify the resulting residue by silica gel chromatography, eluting with 0-9% methanol (2N NH$_3$)/CH$_2$Cl$_2$ to give 390 mg (72%) of the title compound as a white solid. MS/ES m/z ($^{81}$Br) 424.0 [M+H]$^+$.

Preparation 83

(±)-cis-[1-(5-Bromo-pyridin-2-yl)-4-fluoro-pyrrolidin-3-yl]-(3,4-dimethoxy-benzyl)-methyl-amine Prepare the title compound by essentially following procedures as described in Preparation 71 using (±)-trans-1-(5-bromo-pyridin-2-yl)-4-[(3,4-dimethoxy-benzyl)-methyl-amino]-pyrrolidin-3-ol to give 181 mg (97%) of a clear oil. MS/ES m/z ($^{79}$Br) 424.0 [M+H]$^+$.

Preparation 84

5-[2-(4-Chloro-phenyl)-7-oxo-4,7-dihydro-5H-thieno[2,3-c]pyridin-6-yl]-pyridine-2-carboxylic acid methyl ester Combine 2-(4-chloro-phenyl)-5,6-dihydro-4H-thieno[2,3-c]pyridin-7-one (0.351 g, 1.32 mmol) and 5-bromo-pyridine-2-carboxylic acid methyl ester (Song, J.; Yee, N. K. *J. Org. Chem.* 2001, 66, 605) (0.345 g, 1.59 mmol) in dioxane (20 mL). Treat the solution with Xantphos (38 mg, 0.066 mmol) and Cs$_2$CO$_3$ (0.647 g, 1.97 mmol). Degas the reaction by purging with nitrogen for 5 min. Add Pd$_2$(dba)$_3$ (12 mg, 0.0132 mmol) and reflux the reaction mixture overnight. Dilute with EtOAc (100 mL) and water (100 mL). Collect the insoluble material by filtration. Wash with water (2×20 mL) and EtOAc (2×20 mL) and dry in a vacuum oven to give 0.403 g (76%) of the title compound. LC-MS/ES ($^{35}$Cl) 399.0 [M+H]$^+$.

Example 1

4-[2-(4-Chloro-phenyl)-7-oxo-4,7-dihydro-5H-thieno[2,3-c]pyridin-6-yl]-2-methoxy-N-(2-pyrrolidin-1-yl-ethyl)-benzamide, hydrochloride Mix 5-[2-(4-chloro-phenyl)-7-oxo-4,7-dihydro-5H-thieno[2,3-c]pyridin-6-yl]-pyridine-2-carboxylic acid methyl ester (0.099 g, 0.25 mmol) with 2-pyrrolidin-1-yl-ethylamine (34 mg) in toluene (5 mL). Add Al(CH$_3$)$_3$ (130 μL, 0.26 mmol) and stir the mixture at 60° C. overnight. Cool to 0° C. and quench with water (5 mL). Dilute with EtOAc (20 mL) and filter off the insoluble material. Dilute the filtrate with EtOAc (50 mL), wash with saturated NaHCO$_3$ (2×30 mL), dry over Na$_2$SO$_4$, filter and concentrate. Purify the crude material by chromatography, eluting with 10% CH$_3$OH (2N NH$_3$)/CH$_2$Cl$_2$ to give 0.058 g. Dissolve the material in CH$_2$Cl$_2$ (5 mL) and treat with 1.0 M HCl in EtOH (118 μL). Stir at RT for 5 min and concentrate to give 0.051 g, (39%) of the title compound. LC-MS/ES ($^{35}$Cl) 481.2 [M+H]$^+$.

Example 2

2-(4-Chloro-phenyl)-6-[6-((S)-3-dimethylamino-pyrrolidin-1-yl)-pyridin-3-yl]-6H-thieno[2,3-c]pyridin-7-one, hydrochloride

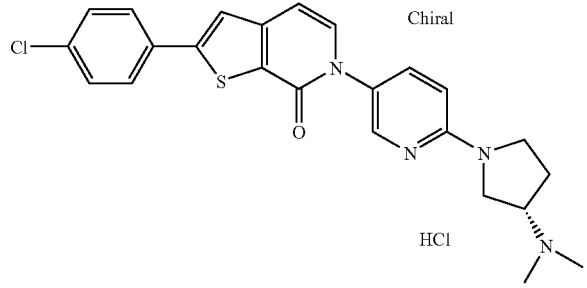

Combine 2-(4-chloro-phenyl)-6H-thieno[2,3-c]pyridin-7-one (0.2575 g, 0.98 mmol), [(S)-1-(5-bromo-pyridin-2-yl)-pyrrolidin-3-yl]-dimethyl-amine (Goodfellow, V.; et. al. US 2005012853) (0.3184 g, 1.18 mmol), and Cs$_2$CO$_3$ (0.64 g, 1.96 mmol) in dioxane (25 mL). Degass the suspension by purging with nitrogen for 5 min. Add CuI (37 mg, 0.20 mmol) and N,N'-dimethylethylenediamine (35 mg). Stir the reaction mixture at 100° C. overnight. Cool to RT and dilute with EtOAc (100 mL). Wash with a solution of H$_2$O/NH$_3$.H$_2$O (2×30 mL/2 mL). Dry the organic layer over Na$_2$SO$_4$, filter and concentrate. Purify the crude material by chromatography by eluting with 2% NH$_3$.H$_2$O, 50% CH$_3$OH/EtOAc to provide 0.258 g. Dissolve the material in CH$_2$Cl$_2$ (5 mL) and treat with 1.0 M HCl in EtOH (0.57 mL) to provide 0.278 g (58%) of the title compound. LC-MS/ES m/z ($^{35}$Cl) 451.2 (M+H)$^+$.

Prepare the following Preparations and Examples in the table below, essentially as described in Example 2, using the appropriate 5,6-dihydro-4H-thieno[2,3-c]pyridin-7-one or 6H-thieno[2,3-c]pyridin-7-one and the appropriate 5-bromopyridine. Use about 0.1 to 0.3 eq of CuI, 1.6 to 2.0 eq of $Cs_2CO_3$, and 0.34 to 0.4 eq of N,N'-dimethylethylenediamine. Prepare (R)-1-(5-bromo-pyridin-2-yl)-pyrrolidin-3-ol according to Stenkamp, D. et al WO 2005103032.

Alternate Workup (Examples 10 to 62): Add to the cooled reaction mixture concentrated $NH_4OH$ (5 mL). After 10 min pour the mixture into water (50 mL). Filter the resulting solid and rinse with water (2×) and then with $Et_2O$ (2×). Purify using chromatography (0 to 10% $MeOH/CH_2Cl_2$) to afford the title compound. Prepare the hydrochloride salt where indicated by adding one equivalent of 1 M hydrogen chloride in ethanol, then precipitating with ether and filtering off the title compounds.

Alternate Workup (Examples 63 to 67, Prep 93): Cool the crude reaction mixture to room temperature and filter, washing the solids with ethyl acetate. Evaporate the solution and purify by silica gel chromatography, eluting with 0-6% methanol (2N $NEt_3$)/$CH_2Cl_2$ to give a white solid. Dissolve the solid in methanol and add ammonium chloride. Evaporate the mixture to give the title compound.

| Ex or Prep | Chemical Name | LC-MS/ES or MS/ES (m/z) or 1H NMR ($CDCl_3$) |
|---|---|---|
| 3 | 2-(4-Chloro-phenyl)-6-[6-((R)-3-dimethylamino-pyrrolidin-1-yl)-5-methyl-pyridin-3-yl]-6H-thieno[2,3-c]pyridin-7-one, hydrochloride | ($^{35}$Cl) 465.3 [M + H]$^+$ |
| 4* | 2-(4-Chloro-phenyl)-6-[6-((R)-3-hydroxy-pyrrolidin-1-yl)-pyridin-3-yl]-5,6-dihydro-4H-thieno[2,3-c]pyridin-7-one, hydrochloride | ($^{37}$Cl) 427.2 [M+] |
| 5 | 2-(4-Chloro-phenyl)-6-[6-((R)-3-dimethylamino-pyrrolidin-1-yl)-pyridin-3-yl]-5,6-dihydro-4H-thieno[2,3-c]pyridin-7-one, hydrochloride | ($^{37}$Cl) 454.3 [M+] |
| 6 | 2-(4-Chloro-phenyl)-6-[6-((S)-3-dimethylamino-pyrrolidin-1-yl)-pyridin-3-yl]-5,6-dihydro-4H-thieno[2,3-c]pyridin-7-one, hydrochloride | ($^{37}$Cl) 454.3 [M+] |
| 7 | 2-(4-Chloro-phenyl)-6-[6-((R)-3-dimethylamino-pyrrolidin-1-yl)-5-methyl-pyridin-3-yl]-5,6-dihydro-4H-thieno[2,3-c]pyridin-7-one, hydrochloride | ($^{37}$Cl) 468.3 [M + H]$^+$ |
| 8** | 2-(4-Chloro-phenyl)-6-(4-dimethylamino-3,4,5,6-tetrahydro-2H-[1,2']bipyridinyl-5'-yl)-6H-thieno[2,3-c]pyridin-7-one, dihydrochloride | ($^{35}$Cl) 465.0 [M + H]$^+$ |
| 9** | 2-(4-Chloro-phenyl)-6-(4-hydroxy-3,4,5,6-tetrahydro-2H-[1,2']bipyridinyl-5'-yl)-6H-thieno[2,3-c]pyridin-7-one, hydrochloride | ($^{35}$Cl) 438.0 [M + 1]$^+$ |
| Prep 85 | 4-{5-[2-(4-Chloro-phenyl)-7-oxo-7H-thieno[2,3-c]pyridin-6-yl]-pyridin-2-yloxy}-piperidine-1-carboxylic acid tert-butyl ester | ($^{37}$Cl) 438.0 [M − $CO_2$tBu]$^+$ |
| Prep 86 | (R)-3-{5-[2-(4-Chloro-phenyl)-7-oxo-7H-thieno[2,3-c]pyridin-6-yl]-pyridin-2-yloxy}-piperidine-1-carboxylic acid tert-butyl ester | ($^{37}$Cl) 438.0 [M − $CO_2$tBu]$^+$ |
| Prep 87 | (S)-3-{5-[2-(4-Chloro-phenyl)-7-oxo-7H-thieno[2,3-c]pyridin-6-yl]-pyridin-2-yloxy}-piperidine-1-carboxylic acid tert-butyl ester | ($^{37}$Cl) 438.0 [M − $CO_2$tBu]$^+$ |
| Prep 88 | ((R)-1-{5-[2-(4-Chloro-phenyl)-7-oxo-4,7-dihydro-5H-thieno[2,3-c]pyridin-6-yl]-pyridin-2-yl}-pyrrolidin-3-yl)-carbamic acid tert-butyl ester | ($^{37}$Cl) 525.2 [M + H]$^+$ |
| Prep 89 | (R)-3-{5-[2-(4-Chloro-phenyl)-7-oxo-7H-thieno[2,3-c]pyridin-6-yl]-pyridin-2-yloxy}-pyrrolidine-1-carboxylic acid tert-butyl ester | ($^{37}$Cl) 468.0 [M − tBu]$^+$ |
| Prep 90 | (S)-3-{5-[2-(4-Chloro-phenyl)-7-oxo-7H-thieno[2,3-c]pyridin-6-yl]-pyridin-2-yloxy}-pyrrolidine-1-carboxylic acid tert-butyl ester | ($^{37}$Cl) 468.0 [M − tBu]$^+$ |
| Prep 91 | 4-{5-[2-(4-Chloro-phenyl)-7-oxo-4,7-dihydro-5H-thieno[2,3-c]pyridin-6-yl]-pyridin-2-yloxy}-piperidine-1-carboxylic acid tert-butyl ester | ($^{35}$Cl) 540.0 [M + 1]$^+$ |
| Prep 92 | 2-(4-Chloro-phenyl)-6-[6-((S)-3-hydroxy-pyrrolidin-1-yl)-pyridin-3-yl]-6H-thieno[2,3-c]pyridin-7-one | ($^{35}$Cl) 424.0 [M + H]$^+$ |
| 10 | 2-(4-Chloro-phenyl)-6-{6-[(R)-3-(2-hydroxy-ethylamino)-pyrrolidin-1-yl]-pyridin-3-yl}-6H-thieno[2,3-c]pyridin-7-one | MS/ES m/z 467.0 [M + H]$^+$. |
| 11 | 2-(4-Cyclopropoxy-phenyl)-6-{6-[(R)-3-(2,2-difluoro-ethylamino)-pyrrolidin-1-yl]-pyridin-3-yl}-6H-thieno[2,3-c]pyridin-7-one, hydrochloride | ($^{35}$Cl) 509.0 [M + H]$^+$ |
| 12 | 2-(4-Chloro-phenyl)-6-{6-[(S)-3-(2,2-difluoro-ethylamino)-pyrrolidin-1-yl]-pyridin-3-yl}-6H-thieno[2,3-c]pyridin-7-one hydrochloride | ($^{35}$Cl) 487.2 [M + H]$^+$ |
| 13 | 6-{6-[(S)-3-(2,2-Difluoro-ethylamino)-pyrrolidin-1-yl]-pyridin-3-yl}-2-(4-fluoro-phenyl)-6H-thieno[2,3-c]pyridin-7-one hydrochloride | ($^{35}$Cl) 471.0 [M + H]$^+$ |
| 14 | 6-{6-[3-(2,2-Difluoro-ethylamino)-pyrrolidin-1-yl]-pyridin-3-yl}-2-(3,4-difluoro-phenyl)-6H-thieno[2,3-c]pyridin-7-one, hydrochloride | 489.0 [M + H]$^+$ |

-continued

| Ex or Prep | Chemical Name | LC-MS/ES or MS/ES (m/z) or 1H NMR (CDCl₃) |
|---|---|---|
| 15 | 2-(4-Chloro-phenyl)-6-[6-((S)-3-hydroxy-pyrrolidin-1-yl)-pyridin-3-yl]-5,6-dihydro-4H-thieno[2,3-c]pyridin-7-one | ($^{37}$Cl) 427.2 [M⁺] |
| 16 | 2-(4-Chloro-phenyl)-6-[6-((3R,3'S)-3-fluoro-[1,3']bipyrrolidinyl-1'-yl)-pyridin-3-yl]-6H-thieno[2,3-c]pyridin-7-one, hydrochloride | δ 1.80-2.00 (m, 1H), 2.00-2.13 (m, 1H), 2.14-2.54 (m, 2H), 3.19-4.50 (m, 9H), 5.15-5.33 (m, 1H), 5.49 (bs, 1H), 6.75 (d, J = 6.9 Hz, 1H), 6.86 (d, J = 9.2 Hz, 1H), 7.24 (d, J = 9.2 hz, 1H), 7.41 (s, 1H), 7.43 (d, J = 8.7 Hz, 2H), 7.64 (d, J = 8.7 Hz, 2H), 8.15 (bs, 1H), 8.28 (bs, 1H). |
| 17 | 2-(4-Chloro-phenyl)-6-[6-((3S,3'R)-3-fluoro-[1,3']bipyrrolidinyl-1'-yl)-pyridin-3-yl]-6H-thieno[2,3-c]pyridin-7-one, hydrochloride | δ 1.80-2.00 (m, 1H), 2.00-2.13 (m, 1H), 2.14-2.54 (m, 2H), 3.19-4.50 (m, 9H), 5.15-5.33 (m, 1H), 5.49 (bs, 1H), 6.75 (d, J = 6.9 Hz, 1H), 6.86 (d, J = 9.2 Hz, 1H), 7.24 (d, J = 9.2 hz, 1H), 7.41 (s, 1H), 7.43 (d, J = 8.7 Hz, 2H), 7.64 (d, J = 8.7 Hz, 2H), 8.15 (bs, 1H), 8.28 (bs, 1H). |
| 18 | 2-(4-Chloro-phenyl)-6-{6-[(R)-3-(2,2-difluoro-ethylamino)-pyrrolidin-1-yl]-pyridin-3-yl}-6H-thieno[2,3-c]pyridin-7-one, hydrochloride | ($^{35}$Cl) 487.0 [M + H]⁺ |
| 19 | 2-(4-Chloro-phenyl)-6-{6-[(R)-3-(2,2-difluoro-ethylamino)-pyrrolidin-1-yl]-pyridin-3-yl}-5,6-dihydro-4H-thieno[2,3-c]pyridin-7-one, hydrochloride | ($^{35}$Cl) 489.0 [M + H]⁺ |
| 20 | 6-{6-[(R)-3-(2,2-Difluoro-ethylamino)-pyrrolidin-1-yl]-pyridin-3-yl}-2-(4-fluoro-phenyl)-6H-thieno[2,3-c]pyridin-7-one, hydrochloride | ($^{35}$Cl) 471.0 [M + H]⁺ |
| 21 | 2-(4-Chloro-phenyl)-6-{6-[(R)-3-(2,2,2-trifluoro-ethylamino)-pyrrolidin-1-yl]-pyridin-3-yl}-6H-thieno[2,3-c]pyridin-7-one, hydrochloride | ($^{35}$Cl) 504.8 [M + H]⁺ |
| 22 | 2-(4-Chloro-phenyl)-6-[6-((R)-3-dicyclopropylamino-pyrrolidin-1-yl)-pyridin-3-yl]-6H-thieno[2,3-c]pyridin-7-one, hydrochloride | ($^{35}$Cl) 503.0 [M + H]⁺ |
| 23 | 2-(4-Chloro-phenyl)-6-[6-(4-methyl-piperazin-1-yl)-pyridin-3-yl]-6H-thieno[2,3-c]pyridin-7-one, hydrochloride | ($^{35}$Cl) 436.8 [M + H]⁺ |
| 24 | 2-(4-Chloro-phenyl)-6-[6-(4-methyl-piperazin-1-yl)-pyridin-3-yl]-5,6-dihydro-4H-thieno[2,3-c]pyridin-7-one, hydrochloride | ($^{35}$Cl) 439.2 [M + H]⁺ |
| 25 | 6-{6-(R)-[3-(2,2-Difluoro-ethylamino)-pyrrolidin-1-yl]-pyridin-3-yl}-2-(4-trifluoromethoxy-phenyl)-6H-thieno[2,3-c]pyridin-7-one, hydrochloride | 537.2 [M + H]⁺ |
| 26 | 6-[6-(R)-(3-Dimethylamino-pyrrolidin-1-yl)-pyridin-3-yl]-2-(4-trifluoromethoxy-phenyl)-6H-thieno[2,3-c]pyridin-7-one, hydrochloride | 501.2 [M + H]⁺ |
| 27 | 6-[6-(R)-(3-Dimethylamino-pyrrolidin-1-yl)-pyridin-3-yl]-2-(4-trifluoromethyl-phenyl)-6H-thieno[2,3-c]pyridin-7-one, hydrochloride | 485.2 [M + H]⁺ |
| 28 | 6-{6-(R)-[3-(2,2-Difluoro-ethylamino)-pyrrolidin-1-yl]-pyridin-3-yl}-2-(4-trifluoromethyl-phenyl)-6H-thieno[2,3-c]pyridin-7-one, hydrochloride | 521.2 [M + H]⁺ |
| 29 | 6-[6-(R)-(3-Dimethylamino-pyrrolidin-1-yl)-pyridin-3-yl]-2-(3-fluoro-4-methoxy-phenyl)-6H-thieno[2,3-c]pyridin-7-one, hydrochloride | 465 [M + H]⁺ |
| 30 | 6-{6-(R)-[3-(2,2-Difluoro-ethylamino)-pyrrolidin-1-yl]-pyridin-3-yl}-2-(3-fluoro-4-methoxy-phenyl)-6H-thieno[2,3-c]pyridin-7-one, hydrochloride | 501 [M + H]⁺ |
| 31 | 6-{6-(R)-[3-(2,2-Difluoro-ethylamino)-pyrrolidin-1-yl]-pyridin-3-yl}-2-(2-fluoro-4-methoxy-phenyl)-6H-thieno[2,3-c]pyridin-7-one, hydrochloride | 501.2 [M + H]⁺ |

-continued

| Ex or Prep | Chemical Name | LC-MS/ES or MS/ES (m/z) or 1H NMR (CDCl$_3$) |
|---|---|---|
| 32 | 6-[6-(R)-(3-Dimethylamino-pyrrolidin-1-yl)-pyridin-3-yl]-2-(2-fluoro-4-methoxy-phenyl)-6H-thieno[2,3-c]pyridin-7-one, hydrochloride | 465 [M + H]$^+$ |
| 33 | 6-[6-(R)-(3-Dimethylamino-pyrrolidin-1-yl)-pyridin-3-yl]-2-(4-fluoro-phenyl)-6H-thieno[2,3-c]pyridin-7-one, hydrochloride | 435.2 [M + H]$^+$ |
| 34 | 6-[6-(3-(S)-Dimethylamino-pyrrolidin-1-yl)-pyridin-3-yl]-2-(2-fluoro-4-methoxy-phenyl)-5,6-dihydro-4H-thieno[2,3-c]pyridin-7-one, hydrochloride | 467.2 [M + H]$^+$ |
| 35 | 6-[6-(R)-(3-Dimethylamino-pyrrolidin-1-yl)-pyridin-3-yl]-2-(2-fluoro-4-methoxy-phenyl)-5,6-dihydro-4H-thieno[2,3-c]pyridin-7-one, hydrochloride | 467.2 [M + H]$^+$ |
| 36 | 6-[6-(S)-(3-Dimethylamino-pyrrolidin-1-yl)-pyridin-3-yl]-2-(4-trifluoromethoxy-phenyl)-5,6-dihydro-4H-thieno[2,3-c]pyridin-7-one, hydrochloride | 503.0 [M + H]$^+$ |
| 37 | 6-[6-(R)-(3-Dimethylamino-pyrrolidin-1-yl)-pyridin-3-yl]-2-(4-trifluoromethoxy-phenyl)-5,6-dihydro-4H-thieno[2,3-c]pyridin-7-one, hydrochloride | 503.0 [M + H]+ |
| 38 | 6-[6-(S)-(3-Dimethylamino-pyrrolidin-1-yl)-pyridin-3-yl]-2-(4-methoxy-phenyl)-5,6-dihydro-4H-thieno[2,3-c]pyridin-7-one, hydrochloride | 449.2 [M + H]$^+$ |
| 39 | 6-[6-(R)-(3-Dimethylamino-pyrrolidin-1-yl)-pyridin-3-yl]-2-(4-methoxy-phenyl)-5,6-dihydro-4H-thieno[2,3-c]pyridin-7-one, hydrochloride | 449.2 [M + H]$^+$ |
| 40 | 6-[6-(S)-(3-Dimethylamino-pyrrolidin-1-yl)-pyridin-3-yl]-2-(4-trifluoromethyl-phenyl)-5,6-dihydro-4H-thieno[2,3-c]pyridin-7-one, hydrochloride | 487.0 [M + H]+ |
| 41 | 6-[6-(R)-(3-Dimethylamino-pyrrolidin-1-yl)-pyridin-3-yl]-2-(4-trifluoromethyl-phenyl)-5,6-dihydro-4H-thieno[2,3-c]pyridin-7-one, hydrochloride | 487.0 [M + H]+ |
| 42 | 6-[6-(S)-(3-Dimethylamino-pyrrolidin-1-yl)-pyridin-3-yl]-2-(3-fluoro-4-methoxy-phenyl)-5,6-dihydro-4H-thieno[2,3-c]pyridin-7-one, hydrochloride | 467.2 [M + H]+ |
| 43 | 6-[6-(R)-(3-Dimethylamino-pyrrolidin-1-yl)-pyridin-3-yl]-2-(3-fluoro-4-methoxy-phenyl)-5,6-dihydro-4H-thieno[2,3-c]pyridin-7-one, hydrochloride | 467.2 [M + H]+ |
| 44 | 2-(4-Cyclopropoxy-phenyl)-6-[6-(S)-(3-dimethylamino-pyrrolidin-1-yl)-pyridin-3-yl]-5,6-dihydro-4H-thieno[2,3-c]pyridin-7-one, hydrochloride | 475.2 [M + H]$^+$ |
| 45 | 2-(3,4-Difluoro-phenyl)-6-[6-(S)-(3-dimethylamino-pyrrolidin-1-yl)-pyridin-3-yl]-5,6-dihydro-4H-thieno[2,3-c]pyridin-7-one, hydrochloride | 455.2 [M + H]+ |
| 46 | 2-(3,4-Difluoro-phenyl)-6-[6-(R)-(3-dimethylamino-pyrrolidin-1-yl)-pyridin-3-yl]-5,6-dihydro-4H-thieno[2,3-c]pyridin-7-one, hydrochloride | 455.2 [M + H]+ |
| 47 | 2-(2,4-Difluoro-phenyl)-6-[6-(S)-(3-dimethylamino-pyrrolidin-1-yl)-pyridin-3-yl]-5,6-dihydro-4H-thieno[2,3-c]pyridin-7-one, hydrochloride | 455.2 [M + H]+ |
| 48 | 2-(2,4-Difluoro-phenyl)-6-[6-(R)-(3-dimethylamino-pyrrolidin-1-yl)-pyridin-3-yl]-5,6-dihydro-4H-thieno[2,3-c]pyridin-7-one, hydrochloride | 455.2 [M + H]+ |
| 49 | 6-[6-(S)-(3-Dimethylamino-pyrrolidin-1-yl)-pyridin-3-yl]-2-(4-fluoro-phenyl)-5,6-dihydro-4H-thieno[2,3-c]pyridin-7-one, hydrochloride | 437.2 [M + H]+ |
| 50 | 6-[6-(R)-(3-Dimethylamino-pyrrolidin-1-yl)-pyridin-3-yl]-2-(4-fluoro-phenyl)-5,6-dihydro-4H-thieno[2,3-c]pyridin-7-one, hydrochloride | 437.2 [M + H]+ |
| 51 | 2-(3,5-Difluoro-phenyl)-6-[6-(R)-(3-dimethylamino-pyrrolidin-1-yl)-pyridin-3-yl]-5,6-dihydro-4H-thieno[2,3-c]pyridin-7-one, hydrochloride | 455.2 [M + H]+ |
| 52 | 2-(3,4-Difluoro-phenyl)-6-[6-(R)-(3-dimethylamino-pyrrolidin-1-yl)-pyridin-3-yl]-6H-thieno[2,3-c]pyridin-7-one, hydrochloride | 453.2 [M + H]$^+$ |
| 53 | 2-(3,4-Dimethoxy-phenyl)-6-[6-(R)-(3-dimethylamino-pyrrolidin-1-yl)-pyridin-3-yl]-6H-thieno[2,3-c]pyridin-7-one, hydrochloride | 477.2 [M + H]$^+$ |
| 54 | 2-(4-Cyclopropoxy-phenyl)-6-[6-(S)-(3-dimethylamino-pyrrolidin-1-yl)-pyridin-3-yl]-6H-thieno[2,3-c]pyridin-7-one, hydrochloride | 473.2 [M + H]$^+$ |
| 55 | 2-(4-Cyclopropoxy-phenyl)-6-[6-(R)-(3-dimethylamino-pyrrolidin-1-yl)-pyridin-3-yl]-6H-thieno[2,3-c]pyridin-7-one, hydrochloride | 473.2 [M + H]$^+$ |
| 56 | 2-(2,4-Difluoro-phenyl)-6-[6-(S)-(3-dimethylamino-pyrrolidin-1-yl)-pyridin-3-yl]-6H-thieno[2,3-c]pyridin-7-one, dihydrochloride | 453.0 [M + H]$^+$ |

-continued

| Ex or Prep | Chemical Name | LC-MS/ES or MS/ES (m/z) or 1H NMR (CDCl₃) |
|---|---|---|
| 57 | 2-(2,4-Difluoro-phenyl)-6-[6-(R)-(3-dimethylamino-pyrrolidin-1-yl)-pyridin-3-yl]-6H-thieno[2,3-c]pyridin-7-one, dihydrochloride | 453.2 [M + H]⁺ |
| 58 | (±)-2-(4-Chloro-phenyl)-6-[6-(4-methyl-morpholine-2-carbonyl)-pyridin-3-yl]-6H-thieno[2,3-c]pyridin-7-one, hydrochloride | ($^{35}$Cl) 466.0 [M + H]⁺ |
| 59 | (±)-2-(4-Chloro-phenyl)-6-[6-(1-methyl-pyrrolidine-3-carbonyl)-pyridin-3-yl]-6H-thieno[2,3-c]pyridin-7-one, hydrochloride | ($^{35}$Cl) 450.0 [M + H]⁺ |
| 60 | (±)-2-(4-Chloro-phenyl)-6-[6-(1-methyl-pyrrolidine-3-carbonyl)-pyridin-3-yl]-5,6-dihydro-4H-thieno[2,3-c]pyridin-7-one, hydrochloride | ($^{35}$Cl) 452.0 [M + H]⁺ |
| 61 | 2-(4-Chloro-phenyl)-6-[6-(4-methyl-[1,4]diazepan-1-yl)-pyridin-3-yl]-6H-thieno[2,3-c]pyridin-7-one, hydrochloride | ($^{35}$Cl) 451 [M + H]⁺ |
| 62 | 2-(4-Chloro-phenyl)-6-[6-(4-methyl-[1,4]diazepan-1-yl)-pyridin-3-yl]-5,6-dihydro-4H-thieno[2,3-c]pyridin-7-one, hydrochloride | ($^{35}$Cl) 453.2 [M + H]⁺ |
| 63 | (±)-trans-2-(4-Chloro-phenyl)-6-[6-(4'-hydroxy-[1,3']bipyrrolidinyl-1'-yl)-pyridin-3-yl]-5,6-dihydro-4H-thieno[2,3-c]pyridin-7-one, hydrochloride | ($^{35}$Cl) 495.0 [M + H]⁺. |
| 64 | (±)-cis-2-(4-Chloro-phenyl)-6-[6-(4'-fluoro-[1,3']bipyrrolidinyl-1'-yl)-pyridin-3-yl]-5,6-dihydro-4H-thieno[2,3-c]pyridin-7-one, hydrochloride | ($^{35}$Cl) 497 [M + H]⁺ |
| 65 | (±)-trans-2-(4-Chloro-phenyl)-6-[6-(3-dimethylamino-4-hydroxy-pyrrolidin-1-yl)-pyridin-3-yl]-5,6-dihydro-4H-thieno[2,3-c]pyridin-7-one, hydrochloride | ($^{35}$Cl) 469 [M + H]⁺ |
| 66 | (±)-cis-2-(4-Chloro-phenyl)-6-[6-(3-dimethylamino-4-fluoro-pyrrolidin-1-yl)-pyridin-3-yl]-5,6-dihydro-4H-thieno[2,3-c]pyridin-7-one, hydrochloride | ($^{35}$Cl) 471 [M + H]⁺ |
| 67 | (±)-trans-2-(4-Chloro-phenyl)-6-[6-(3-dimethylamino-4-hydroxy-pyrrolidin-1-yl)-pyridin-3-yl]-6H-thieno[2,3-c]pyridin-7-one, hydrochloride | ($^{35}$Cl) 467.0 [M + H]⁺ |
| Prep 93 | 2-(4-Chloro-phenyl)-6-(6-{3-[(3,4-dimethoxy-benzyl)-methyl-amino]-4-fluoro-pyrrolidin-1-yl}-pyridin-3-yl)-5,6-dihydro-4H-thieno[2,3-c]pyridin-7-one | ($^{35}$Cl) 607.0 [M + H]⁺ |

*Obtain HCl salt by dissolving free base in CH₃OH and treating with 1.0 M HCl in EtOAc.
**Obtain HCl salt by treating free base with 1.0 M HCl in diethyl ether.

Example 68

2-(4-Chloro-phenyl)-6-[6-((R)-3-dimethylamino-pyrrolidin-1-yl)-pyridin-3-yl]-6H-thieno[2,3-c]pyridin-7-one, hydrochloride

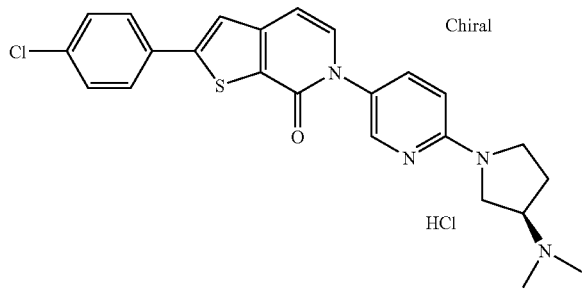

Charge [1-(5-bromo-pyridin-2-yl)-pyrrolidin-3-yl]-dimethyl-amine (6.8 g, 25.2 mmol), 2-(4-chloro-phenyl)-6H-thieno[2,3-c]pyridin-7-one (6.5 g, 24.8 mmol), cesium carbonate (16.3 g, 50.0 mmol), and 1,4-dioxane (230 mL) to a flask. Cool the mixture to 11-13° C. and sparge with subsurface nitrogen for 15-25 min. Charge this mixture with copper (I) iodide (1.0 g, 5.3 mmol) followed by a solution of sym-dimethylethylene diamine (0.9 g, 10.2 mmol) in 1,4-dioxane (5 mL). Sparge this mixture with subsurface nitrogen for 5-10 min and heat to 98° C. under nitrogen. Stir the reaction at 98° C. overnight.

Cool the reaction to 11-13° C., charge with additional [1-(5-bromo-pyridin-2-yl)-pyrrolidin-3-yl]-dimethyl-amine (0.5 g, 1.9 mmol), and sparge with subsurface nitrogen for 10 min. Charge the mixture with additional copper (I) iodide (1.0 g, 5.3 mmol) and sym-dimethylethylene diamine (0.9 g, 10.2 mmol). Sparge the reaction mixture with nitrogen for 5 min and stir at 98° C. overnight.

Bring the reaction to room temperature and charge with water (93 mL) followed by ammonium hydroxide (46 mL). Stir the mixture at room temperature for 15 min and filter. Rinse the solid with water (46 mL) and dry on the filter with vacuum/nitrogen overnight to yield 6.9 g (62%). Purify a portion of the material (3.56 g) by flash chromatography, using 5% MeOH (2N NH₃)/CH₂Cl₂ to give 3.31 g (93%) of 2-(4-chloro-phenyl)-6-[6-(3-dimethylamino-pyrrolidin-1-yl)-pyridin-3-yl]-6H-thieno[2,3-c]pyridin-7-one as a white solid. Dissolve the free base (3.06 g, 6.79 mmol) in a mixture of CH₂Cl₂ (40 mL) and MeOH (1.5 mL). Treat the solution with 1M HCl in ethanol (7.2 mL, 7.2 mmol) and stir the mixture at RT for 1.5 h. Dilute the mixture with ether (50 mL) and collect the solid by filtration. Wash the solid with additional ether (50 mL) and dry under vacuum to give the title compound (3.38 g) as a yellow solid. MS/ES m/z ($^{35}$Cl) 451.0 [M+H]⁺.

Example 69

2-(4-Chloro-phenyl)-6-[6-(piperidin-4-yloxy)-pyridin-3-yl]-6H-thieno[2,3-c]pyridin-7-one hydrochloride

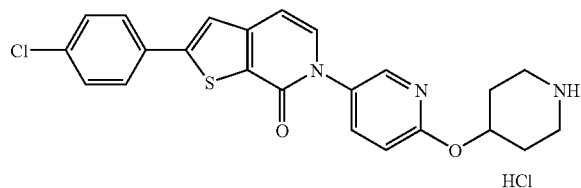

Combine 4-{5-[2-(4-chloro-phenyl)-7-oxo-7H-thieno[2,3-c]pyridin-6-yl]-pyridin-2-yloxy}-piperidine-1-carboxylic acid tert-butyl ester (1.67g, 3.10 mmol) with trifluoroacetic acid (2.31 mL, 31.04 mmol) in dichloromethane (20 mL) and stir at RT overnight. Load the mixture onto an SCX column and wash with methanol and dichloromethane. Elute the product with 2M $NH_3$ in methanol and concentrate in vacuo. Chromatograph the residue (silica gel, eluting with 0-10% 2M $NH_3$ in MeOH:dichloromethane) to yield 996 mg (73%) of 2-(4-chloro-phenyl)-6-[6-(piperidin-4-yloxy)-pyridin-3-yl]-6H-thieno[2,3-c]pyridin-7-one. Add ammonium chloride (45 mg, 0.85 mmol) to a solution of the free base (350 mg, 0.80 mmol) in 15 mL of methanol/dichloromethane (1:1) and sonicate the solution until complete dissolution of $NH_4Cl$. Concentrate in vacuo to yield 379 mg (100%) of the title compound. MS/ES m/z ($^{35}C_1$) 438.0 [M+H]$^+$.

Prepare the examples in the table below, by following the procedure essentially as described in Example 69.

| Ex | Chemical Name | MS/ES m/z |
|---|---|---|
| 70 | 2-(4-Chloro-phenyl)-6-[6-((R)-piperidin-3-yloxy)-pyridin-3-yl]-6H-thieno[2,3-c]pyridin-7-one, hydrochloride | ($^{35}Cl$) 438.0 [M + H]$^+$ |
| 71 | 2-(4-Chloro-phenyl)-6-[6-((S)-piperidin-3-yloxy)-pyridin-3-yl]-6H-thieno[2,3-c]pyridin-7-one, hydrochloride | ($^{35}Cl$) 438.0 [M + H]$^+$ |
| 72 | 2-(4-Chloro-phenyl)-6-[6-((R)-pyrrolidin-3-yloxy)-pyridin-3-yl]-6H-thieno[2,3-c]pyridin-7-one, hydrochloride | ($^{35}Cl$) 424.0 [M + H]$^+$ |
| 73 | 2-(4-Chloro-phenyl)-6-[6-((S)-pyrrolidin-3-yloxy)-pyridin-3-yl]-6H-thieno[2,3-c]pyridin-7-one, hydrochloride | ($^{35}Cl$) 424.0 [M + H]$^+$ |

Example 74

2-(4-Chloro-phenyl)-6-[6-(piperidin-4-yloxy)-pyridin-3-yl]-5,6-dihydro-4H-thieno[2,3-c]pyridin-7-one, hydrochloride Add 4-{5-[2-(4-chloro-phenyl)-7-oxo-4,7-dihydro-5H-thieno[2,3-c]pyridin-6-yl]-pyridin-2-yloxy}-piperidine-1-carboxylic acid tert-butyl ester (5.41 g, 10.02 mmol) to a solution of 1:1 MeOH:dichloromethane (80 mL). Then add 4M HCl in dioxane (18.53 mL, 74 mmol) and stir at RT overnight. Filter the reaction and wash with dichloromethane. Dry thoroughly to yield the title compound quantitatively. MS/ES m/z ($^{35}Cl$) 440.0 [M+H]$^+$.

Example 75

2-(4-Chloro-phenyl)-6-[6-(1-methyl-piperidin-4-yloxy)-pyridin-3-yl]-6H-thieno[2,3-c]pyridin-7-one, hydrochloride

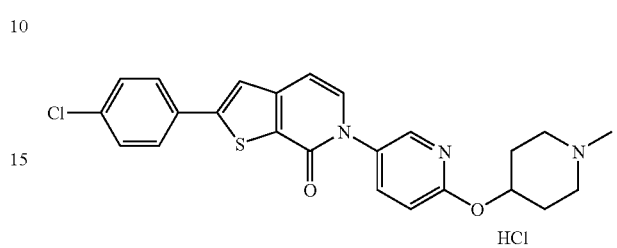

Combine 2-(4-chloro-phenyl)-6-[6-(piperidin-4-yloxy)-pyridin-3-yl]-6H-thieno[2,3-c]pyridin-7-one (500 mg, 1.14 mmol) with acetic acid (0.33 mL, 5.71 mmol) in methanol (40 mL). Cool to 0° C., add formaldehyde (0.25 mL, 3.42 mmol, 37% aqueous solution) and stir for 5 min. Then add sodium cyanoborohydride (179 mg, 2.85 mmol) and warm the reaction to RT with stirring overnight. Concentrate the solution in vacuo and dilute with dichloromethane, saturated aqueous $NaHCO_3$, and water. Separate the organic layer and extract the aqueous layer with dichloromethane. Combine the organic extracts, dry over $MgSO_4$, filter, and concentrate in vacuo. Chromatograph the residue (silica gel, eluting with 0-10% MeOH (2N $NH_3$)/$CH_2Cl_2$ to yield the free base. Add 1 equivalent of ammonium chloride to a solution of the free base in 1:1 methanol/$CH_2Cl_2$ and sonicate the solution until complete dissolution of $NH_4Cl$. Concentrate in vacuo to yield 523 mg (99%) of the title compound. MS/ES m/z ($^{35}Cl$) 452.0 [M+H$^+$].

Prepare the examples in the table below, essentially by following procedures as described in Example 75.

| Ex | Chemical Name | MS/ES m/z |
|---|---|---|
| 76 | 2-(4-Chloro-phenyl)-6-[6-((R)-1-methyl-piperidin-3-yloxy)-pyridin-3-yl]-6H-thieno[2,3-c]pyridin-7-one, hydrochloride | ($^{35}Cl$) 452.0 [M + H]$^+$ |
| 77 | 2-(4-Chloro-phenyl)-6-[6-((S)-1-methyl-piperidin-3-yloxy)-pyridin-3-yl]-6H-thieno[2,3-c]pyridin-7-one,hydrochloride | ($^{35}Cl$) 452 [M + H]$^+$ |
| 78 | 2-(4-Chloro-phenyl)-6-[6-((R)-1-methyl-pyrrolidin-3-yloxy)-pyridin-3-yl]-6H-thieno[2,3-c]pyridin-7-one, hydrochloride | ($^{35}Cl$) 438.0 [M + H]$^+$ |
| 79 | 2-(4-Chloro-phenyl)-6-[6-((S)-1-methyl-pyrrolidin-3-yloxy)-pyridin-3-yl]-6H-thieno[2,3-c]pyridin-7-one, hydrochloride | ($^{35}Cl$) 438.0 [M + H]$^+$ |
| 80 | 2-(4-Chloro-phenyl)-6-[6-(1-methyl-piperidin-4-yloxy)-pyridin-3-yl]-5,6-dihydro-4H-thieno[2,3-c]pyridin-7-one, hydrochloride | ($^{35}Cl$) 454.3 [M + H]$^+$ |

Example 81

6-[6-(1-Acetyl-piperidin-4-yloxy)-pyridin-3-yl]-2-(4-chloro-phenyl)-5,6-dihydro-4H-thieno[2,3-c]pyridin-7-one Add pyridine (0.50 mL, 6.18 mmol) to a mixture of 2-(4-chloro-phenyl)-6-[6-(piperidin-4-yloxy)-pyridin-3-yl]-6H- thieno[2,3-c]pyridin-7-one, hydrochloride (0.741 g, 1.56 mmol) in dichloromethane at room temperature. After stirring for 5 min, add acetyl chloride (0.16 mL, 2.33 mmol) to the mixture and stir overnight at room temperature. Dilute the mixture with water, extract into dichloromethane (3×50 mL), then dry over sodium sulfate, filter, and concentrate. Purify the residue using silica gel flash column chromatography (1-3% methanol/dichloromethane) and concentrate on high vacuum to yield the titled compound (0.678 g, 90%). MS/ES m/z ($^{37}$Cl) 483 [M$^+$].

Prepare the following Examples in the table below, essentially by following procedures as described in Example 81 with the exception that the free base of the starting amines was used.

| Ex | Chemical Name | MS/ES m/z |
|----|---------------|-----------|
| 82 | (R)-6-[6-(1-Acetyl-pyrrolidin-3-yloxy)-pyridin-3-yl]-2-(4-chloro-phenyl)-6H-thieno[2,3-c]pyridin-7-one | ($^{35}$Cl) 466 [M + H]$^+$ |
| 83 | (S)-6-[4-(1-Acetyl-piperidin-3-yloxy)-phenyl]-2-(4-chloro-phenyl)-6H-thieno[2,3-c]pyridin-7-one | ($^{35}$Cl) 480 [M + H]$^+$ |

Example 84

2-(4-Chloro-phenyl)-6-[6-(1-cyclopropyl-pyrrolidin-3(R)-yloxy)-pyridin-3-yl]-6H-thieno[2,3-c]pyridin-7-one, hydrochloride Add sodium cyanoborohydride (0.044 g, 0.703 mmol) to a mixture of 2-(4-chloro-phenyl)-6-[6-(pyrrolidin-3(R)-yloxy)-pyridin-3-yl]-6H-thieno[2,3-c]pyridin-7-one (0.0745 g, 0.176 mmol) and (1-ethoxy-cyclopropoxy)-trimethyl-silane (0.14 mL, 0.703 mmol) in acetic acid (0.05 mL) and methanol (10 mL) at room temperature. Reflux the mixture overnight at 80° C. Dilute the reaction mixture with dichloromethane and wash with 1.0M NaOH. Dilute the organic phase with methanol, dry over sodium sulfate, filter, and concentrate. Purify the mixture using silica gel flash column chromatography, eluting with 2-12% MeOH (2N NH$_3$)/CH$_2$Cl$_2$. Triturate the residue with methanol to yield a white solid. Dissolve the white solid in dichloromethane/methanol, then add ammonium chloride (2 mg) and sonicate the resulting mixture until dissolution of the ammonium chloride. Concentrate the solution, then pump on high vacuum overnight to yield the desired product (0.020 g, 23%). MS/ES m/z ($^{35}$Cl) 464.2 [M+H$^+$].

Example 85

2-(4-Chloro-phenyl)-6-[6-((S)-3-methylamino-pyrrolidin-1-yl)-pyridin-3-yl]-6H-thieno[2,3-c]pyridin-7-one, hydrochloride Prepare the title compound by essentially following the procedure as described for Example 2, using 2-(4-chloro-phenyl)-6H-thieno[2,3-c]pyridin-7-one (0.461 g, 1.759 mmol), and [(S)-1-(5-bromo-pyridin-2-yl)-pyrrolidin-3-yl]-carbamic acid tert-butyl ester (0.660 g, 1.935 mmol) to give the crude amide coupling product, which is used in the next step without purification. Dissolve the material in DMF (20 mL), treat the solution with NaH (60%, 106 mg, 2.64 mmol) and stir at RT for 1 h. Add CH$_3$I (164 μL, 2.64 mmol) and stir the reaction at RT for 3 h. Dilute the reaction with water (100 mL) and extract with EtOAc (3×100 mL). Dry the combined organic layers over Na$_2$SO$_4$, filter and concentrate. Dissolve the resulting crude material in CH$_2$Cl$_2$ (10 mL), treat with TFA (2.0 mL) and stir at RT for 1 h. Remove the excess reagent and solvent in vacuo. Dissolve the resulting residue in CH$_2$Cl$_2$ (50 mL) and wash with saturated NaHCO$_3$ (2×50 mL). Dry the organic portion over Na$_2$SO$_4$, filter and concentrate. Purify the crude material by chromatography (eluting with 2% NH$_3$.H$_2$O, 50% CH$_3$OH/EtOAc) to give 0.569 g of product. Prepare the HCl salt of the material essentially as described in Example 2 to provide 0.608 g (73%) of the title compound. LC-MS/ES m/z ($^{35}$Cl) 437.3 [M+H]$^+$.

Example 86

2-(4-Chloro-phenyl)-6-[6-((R)-3-methylamino-pyrrolidin-1-yl)-pyridin-3-yl]-6H-thieno[2,3-c]pyridin-7-one, hydrochloride Prepare the title compound by essentially following the procedure as described for Example 85, using 2-(4-chloro-phenyl)-6H-thieno[2,3-c]pyridin-7-one (0.530 g, 2.022 mmol), and [(R)-1-(5-bromo-pyridin-2-yl)-pyrrolidin-3-yl]-carbamic acid tert-butyl ester (0.759 g, 2.224 mmol) to give 0.759 g of product. Prepare the HCl salt of the material essentially as described in Example 1 to provide 0.587 g (63%) of the title compound. LC-MS/ES m/z ($^{35}$Cl) 437.3 [M+H]$^+$.

Example 87

2-(4-Chloro-phenyl)-6-[6-((3R,3'R)-3-fluoro-[1,3']bipyrrolidinyl-1'-yl)-pyridin-3-yl]-6H-thieno[2,3-c]pyridin-7-one Dissolve methanesulfonic acid (S)-1-(5-bromo-pyridin-2-yl)-pyrrolidin-3-yl ester (3 g, 9.34 mmol) and (R)-3-fluoro-pyrrolidine hydrochloride (1.00 g, 11.21 mmol) in DMF (50 mL) and add Cs$_2$CO$_3$ (9.13 g, 28.02 mmol). Warm to 70° C. overnight. Dilute with dichloromethane (3×40 mL), wash with H$_2$O (50 mL) and brine. Dry with Na$_2$SO$_4$, filter, and concentrate the organic solution. Purify the crude material by chromatography, eluting with 0-50% EtOAc/hexane, to give 1.14 g (39%) of (3R,3'R)-1'-(5-Bromo-pyridin-2-yl)-3-fluoro-[1,3']bipyrrolidinyl.

Degass a mixture of 2-(4-chloro-phenyl)-6H-thieno[2,3-c]pyridin-7-one (458 mg, 1.75 mmol), (3R,3'R)-1'-(5-bromo-pyridin-2-yl)-3-fluoro-[1,3']bipyrrolidinyl (550 mg, 1.75 mmol) and cesium carbonate (1.14 g, 3.50 mmol) in 1,4-dioxane (20 mL). Add copper (I) iodide (133 mg, 700 μmol) and sym-dimethylethylene diamine (99 μL, 928 μmol). Heat the mixture at 100° C. overnight. Add to the cooled mixture concentrated NH$_4$OH (5 mL). After 10 min, pour the mixture into water (20 mL). Filter the resulting solid and rinse with water (2×), followed by rinsing with Et$_2$O (2×). Purify using chromatography (0 to 5% MeOH/CH$_2$Cl$_2$) to afford 610 mg (71%) of the title compound. $^1$H NMR (400 MHz, CDCl$_3$) δ: 1.95 (m, 1H), 2.24 (m, 3H), 3.59 (m, 8H), 5.18 (d, 1H), 5.40 (brs, 1H), 6.44 (d, 1H), 6.65 (d, 1H), 7.22 (d, 1H), 7.38 (t, 3H), 7.60 (m, 3H), 8.13 (s, 1H).

Example 88

6-[6-((R)-3-Amino-pyrrolidin-1-yl)-pyridin-3-yl]-2-(4-chloro-phenyl)-6H-thieno[2,3-c]pyridin-7-one, hydrochloride

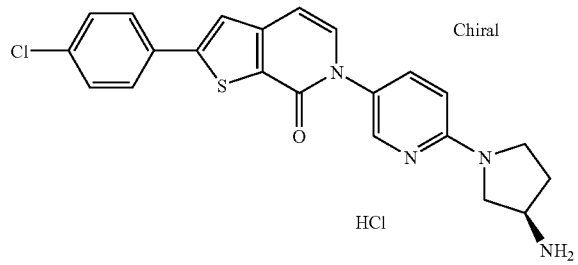

Degass a mixture of 2-(4-chloro-phenyl)-6H-thieno[2,3-c]pyridin-7-one (374 mg, 1.43 mmol), [(R)-1-(5-bromo-pyridin-2-yl)-pyrrolidin-3-yl]-cyclopropyl-amine (404 mg, 1.43 mmol) and cesium carbonate (932 mg, 2.86 mmol) in 1,4-dioxane (20 mL). Add copper (I) iodide (162 mg, 851 μmol) and sym-dimethylethylene diamine (150 mg, 1.70 mmol). Heat the mixture at 100° C. overnight. Dilute with concentrated NH$_4$OH (5 mL) and water (50 mL) and CH$_2$Cl$_2$. Separate the organics and dry with Na$_2$SO$_4$, filter, and concentrate. Purify using chromatography (0 to 10% MeOH/CH$_2$Cl$_2$) to afford 0.384 g (64%) of 6-[6-((R)-3-amino-pyrrolidin-1-yl)-pyridin-3-yl]-2-(4-chloro-phenyl)-6H-thieno[2,3-c]pyridin-7-one.

Prepare the HCl salt by dissolving the free base in MeOH and CH$_2$Cl$_2$ then adding 1N HCl in EtOH and evaporating. Suspend the salt in Et$_2$O and filter to give 0.386 g (93%) of the title compound. MS/ES m/z ($^{35}$Cl) 423.0 [M+H]$^+$.

Example 89

2-(4-Chloro-phenyl)-6-[6-((R)-3-methylamino-pyrrolidin-1-yl)-pyridin-3-yl]-5,6-dihydro-4H-thieno[2,3-c]pyridin-7-one, hydrochloride Dissolve ((R)-1-{5-[2-(4-chloro-phenyl)-7-oxo-4,7-dihydro-5H-thieno[2,3-c]pyridin-6-yl]-pyridin-2-yl}-pyrrolidin-3-yl)-carbamic acid tert-butyl ester (0.367 g, 0.70 mmol) in DMF (10 mL). Treat the mixture with 60% NaH (33.7 mg, 0.84 mmol). Stir the resulting suspension at room temperature for 1 h. Add iodomethane (66 μL, 1.05 mmol) and stir at room temperature for 3 h. Quench the mixture with water (35 mL) and extract with EtOAc (3×40 mL). Wash the combined organic layers with water (3×30 mL), dry with Na$_2$SO$_4$, filter, and concentrate. Dissolve the resulting crude material in CH$_2$Cl$_2$ (5 mL), treat with TFA (3 mL) and stir at room temperature for 1 h. Remove the excess reagent in vacuo. Dilute the residue with CHCl$_3$ (40 mL) and wash with 2.0 M NaOH (30 mL). Treat the cloudy organic layer with CH$_3$OH (1.0 mL), dry with Na$_2$SO$_4$, filter, and concentrate. Purify the crude material by chromatography, eluting with 10% CH$_3$OH (with 2M NH$_3$)/CHCl$_3$ to give 0.222 g (72%) of 2-(4-chloro-phenyl)-6-[6-((R)-3-methylamino-pyrrolidin-1-yl)-pyridin-3-yl]-5,6-dihydro-4H-thieno[2,3-c]pyridin-7-one.

Prepare the hydrochloride salt by dissolving the free base in CH$_2$Cl$_2$ and treating with HCl in ethanol. Precipitate the product out by adding ether and filter the solid to give the title compound. MS/ES m/z ($^{35}$Cl) 439.2 [M+H]$^+$.

Preparation 94

Methanesulfonic acid (S)-1-{5-[2-(4-chloro-phenyl)-7-oxo-4,7-dihydro-5H-thieno[2,3-c]pyridin-6-yl]-pyridin-2-yl}-pyrrolidin-3-yl ester Dissolve 2-(4-chloro-phenyl)-6-[6-((S)-3-hydroxy-pyrrolidin-1-yl)-pyridin-3-yl]-5,6-dihydro-4H-thieno[2,3-c]pyridin-7-one (1.246 g, 2.93 mmol) in CH$_2$Cl$_2$ (25 mL). Cool to 0° C. and treat with Et$_3$N (0.61 mL, 4.39 mmol), followed by MsCl (0.25 mL, 3.22 mmol). Stir at 0° C. for 15 min and at RT for 2 h. Dilute the mixture with CH$_2$Cl$_2$ (50 mL). Wash with H$_2$O (2×40 mL), dry with Na$_2$SO$_4$, filter, and concentrate. Purify the crude material by chromatography, eluting with 10% CH$_3$OH/CH$_2$Cl$_2$ to give 1.21 g (82%) of the title compound. MS/ES m/z ($^{35}$Cl) 504.0 [M+H]$^+$.

Preparation 95

Methanesulfonic acid (S)-1-{5-[2-(4-chloro-phenyl)-7-oxo-7H-thieno[2,3-c]pyridin-6-yl]-pyridin-2-yl}-pyrrolidin-3-yl ester Prepare the title compound by essentially following the procedures as described in Preparation 94 to obtain 0.44 g (62%). MS/ES m/z ($^{35}$Cl) 502.0 [M+H]$^+$.

Example 90

2-(4-Chloro-phenyl)-6-[6-((R)-3-cyclopropylamino-pyrrolidin-1-yl)-pyridin-3-yl]-5,6-dihydro-4H-thieno[2,3-c]pyridin-7-one, hydrochloride Heat methanesulfonic acid (S)-1-{5-[2-(4-chloro-phenyl)-7-oxo-4,7-dihydro-5H-thieno[2,3-c]pyridin-6-yl]-pyridin-2-yl}-pyrrolidin-3-yl ester (1.22 g, 2.40 mmol) and cyclopropyl amine (90.42 mL, 6.01 mmol) in THF (15 mL) in a microwave reactor at 130° C. for 6 h. Dilute the mixture with EtOAc (50 mL) and wash with saturated NaHCO$_3$ (2×20 mL) and brine (20 mL). Dry the organic portion with Na$_2$SO$_4$, filter, and concentrate. Purify the crude material by chromatography, eluting with 1% Et$_3$N in 10% CH$_3$OH/CHCl$_3$ to obtain 0.61 g (55%) of the free base.

Prepare the hydrochloride salt by dissolvling in CH$_2$Cl$_2$ and treating with HCl in ethanol. Precipitate the product out by adding ether. Filter the solid to give 0.266 g (64%) of the title compound. MS/ES m/z ($^{37}$Cl) 466.2 [M$^+$].

Example 91

2-(4-Chloro-phenyl)-6-[6-((R)-3-cyclopropylamino-pyrrolidin-1-yl)-pyridin-3-yl]-6H-thieno[2,3-c]pyridin-7-one, hydrochloride Prepare the title compound by essentially following the procedures as described in the Example 98 using methanesulfonic acid (S)-1-{5-[2-(4-chloro-phenyl)-7-oxo-7H-thieno[2,3-c]pyridin-6-yl]-pyridin-2-yl}-pyrrolidin-3-yl ester to obtain 0.2047 g (67%) of product. MS/ES m/z ($^{35}$Cl) 463.0 [M+H]$^+$.

Example 92

2-(4-Chloro-phenyl)-6-[6-((R)-3-dicyclopropylamino-pyrrolidin-1-yl)-pyridin-3-yl]-5,6-dihydro-4H-thieno[2,3-c]pyridin-7-one, hydrochloride Dissolve ((R)-1-{5-[2-(4-chloro-phenyl)-7-oxo-4,7-dihydro-5H-thieno [2,3-c]pyridin-6-yl]-pyridin-2-yl}-pyrrolidin-3-yl)-carbamic acid tert-butyl ester (0.393 g, 0.750 mmol) in CHCl₃ (5 mL) and treat with TFA (2 mL). Stir the mixture at RT for 30 min. Remove the excess reagent in vacuo. Dissolve the crude material in CH₃OH (10 mL) and treat with HOAc (90.22 mL, 3.93 mmol), and (1-ethoxy-cyclopropoxy)trimethylsilane (0.47 mL, 2.36 mmol). Stir the mixture at RT for 10 min. Add NaBH₃CN (90.36 g, 5.69 mmol) and reflux the reaction overnight. Dilute the mixture with EtOAc (50 mL) and 2.0 M NaOH (920 mL) and then stir at RT for 5 min. Filter and wash the mixture with EtOAc (30 mL). Separate the organic layer and dry with Na₂SO₄, filter, and concentrate. Purify the crude material by chromatography, eluting with 5% CH₃OH (2M NH₃)/CHCl₃ to give 0.35 g (93%) of 2-(4-chloro-phenyl)-6-[6-((R)-3-dicyclopropy-lamino-pyrrolidin-1-yl)-pyridin-3-yl]-5,6-dihydro-4H-thieno[2,3-c]pyridin-7-one.

Prepare the hydrochloride salt by dissolving the free base in methanol and adding 1M HCl in ethanol. Evaporate the solution to give the title compound. MS/ES m/z ($^{35}$Cl) 505.2 [M+H]⁺.

Example 93

2-(4-Chloro-phenyl)-6-(6-{(R)-3-[(2,2-difluoro-ethyl)-methyl-amino]-pyrrolidin-1-yl}-pyridin-3-yl)-6H-thieno[2,3-c]pyridin-7-one, hydrochloride Add sodium cyanoborohydride (716 µmol, 45 mg) to a room temperature mixture of 2-(4-chloro-phenyl)-6-{6-[(R)-3-(2,2-difluoro-ethylamino)-pyrrolidin-1-yl]-pyridin-3-yl}-6H-thieno[2,3-c]pyridin-7-one, hydrochloride (150 mg, 287 µmol), acetic acid (49 µL, 360 µmol,) and formaldehyde (115 µL, 1.53 mmol, 37% aqueous solution) in methanol (9 mL) and stir the mixture for 18 h. Concentrate the mixture and partition between CH₂Cl₂ (5 mL) and 1N NaOH (5 mL). Separate the organic portion and extract the aqueous portion with CH₂Cl₂ (3×). Dry the combined organics over Na₂SO₄, filter, and concentrate to dryness. Purify by chromatography 0% to 5% MeOH (2M NH₃)/CH₂Cl₂ to afford 116 mg (80%) of 2-(4-chloro-phenyl)-6-(6-{(R)-3-[(2,2-difluoro-ethyl)-methyl-amino]-pyrrolidin-1-yl}-pyridin-3-yl)-6H-thieno[2,3-c]pyridin-7-one. Add 1M hydrogen chloride in ethanol (232 µL, 232 µmol) to a solution of 2-(4-chloro-phenyl)-6-(6-{(R)-3-[(2,2-difluoro-ethyl)-methyl-amino]-pyrrolidin-1-yl}-pyridin-3-yl)-6H-thieno[2,3-c]pyridin-7-one (232 µmol, 116 mg) in dichloromethane (2 mL) and stir the mixture at room temperature for 5 min. Dilute the mixture with of Et₂O (8 mL) and filter. Rinse the solid with Et₂O (2×) and dry under vacuum at 80° C. to afford 100 mg (80%) of the title compound. LC-MS/ES m/z ($^{35}$Cl) 501.0 [M+H]⁺.

Example 94

(±)-cis-2-(4-Chloro-phenyl)-6-[6-(3-fluoro-4-methy-lamino-pyrrolidin-1-yl)-pyridin-3-yl]-5,6-dihydro-4H-thieno[2,3-c]pyridin-7-one, hydrochloride Dissolve 2-(4-chloro-phenyl)-6-(6-{3-[(3,4-dimethoxy-benzyl)-methyl-amino]-4-fluoro-pyrrolidin-1-yl}-pyridin-3-yl)-5,6-dihydro-4H-thieno[2,3-c]pyridin-7-one (94 mg, 0.155 mmol) in trifluoroacetic acid (6 mL) and reflux the mixture overnight. Evaporate the solution and apply the residue to a 10 g SCX column with methanol. Wash the column with methanol and elute the crude material with 2N ammonia in methanol. Further purify by silica gel chromatography, eluting with 0-10% methanol (2N NEt₃)/CH₂Cl₂ to give a yellow solid.

Dissolve the solid (27 mg, 59 µmol) in ethanol (2 mL) and add hydrogen chloride (44 µL, 177 µmol, 4M in dioxane). Evaporate the mixture to give 30 mg (38%) of the title compound as a white solid. MS/ES m/z ($^{35}$Cl) 457.0 [M+H]⁺.

Example 95 trans-2-(4-Chloro-phenyl)-6-[6-(3-dimethylamino-4-hydroxy-pyrrolidin-1-yl)-pyridin-3-yl]-6H-thieno[2,3-c]pyridin-7-one, hydrochloride, Isomer 1 and

Example 96 trans-2-(4-Chloro-phenyl)-6-[6-(3-dimethylamino-4-hydroxy-pyrrolidin-1-yl)-pyridin-3-yl]-6H-thieno[2,3-c]pyridin-7-one, hydrochloride, Isomer 2

Purify the enatiomers of (±)2-(4-chloro-phenyl)-6-[6-(3-dimethylamino-4-hydroxy-pyrrolidin-1-yl)-pyridin-3-yl]-6H-thieno[2,3-c]pyridin-7-one using a 3×25 cm Chiralpak™ AD-H 5 µm column eluting with 30% acetonitrile/70% methanol with 0.2% dimethylethylamine to afford two trans isomers. Isomer 1: $T_R$=7.06 min; Isomer 2: $T_R$=7.98 min.

Dissolve each isomer in methanol (3 mL) and add ammonium chloride, then evaporate the mixture to give the title compounds as white solids. LC-MS/ES m/z ($^{35}$Cl) 467.0 [M+H]⁺. Isomer 1: LC-MS/ES m/z ($^{35}$Cl) 467.0 [M+H]⁺; Isomer 2: LC-MS/ES m/z ($^{35}$Cl) 467.0 [M+H]⁺.

We claim:
1. A compound of formula:

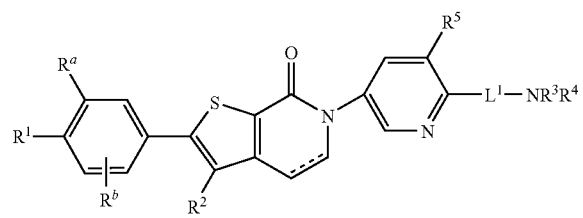

wherein:
"-----" is optionally a bond to form a double bond;
$R^1$ is independently selected from the group consisting of hydrogen, $C_1$-$C_4$ alkyl, halo, $C_1$-$C_4$ haloalkyl, $C_1$-$C_4$ alkoxy, $C_1$-$C_4$ haloalkoxy, and —O—$C_3$-$C_4$ cycloalkyl;
$R^a$ and $R^b$ are independently hydrogen, fluoro, chloro, or methoxy;
$R^2$ is hydrogen or methyl;
$L^1$ is selected from the group consisting of a bond, —OCH$_2$CH$_2$—, —OCH$_2$CH$_2$CH$_2$—, —C(O)NCH$_2$CH$_2$—, —C(O)CH$_2$CH$_2$—, NHC(O)CH$_2$—, and —NHC(O)CH$_2$CH$_2$—; —NHC(O)CH$_2$CH$_2$CH$_2$—, and —C(O)NHCH$_2$CH$_2$CH$_2$
—$R^3$ and $R^4$ combine together with the nitrogen atom to which they are attached to form an optionally substituted 4 to 7-member heterocyclic ring; or one of $R^3$ and $R^4$ combines with $L^1$ at a position α, β, γ, or, δ to the nitrogen of N$R^3R^4$ to form a nitrogen containing 4 to 7-member heterocyclic ring with $L^1$; wherein each 4 to 7 member nitrogen containing heterocyclic ring formed by $R^3$ and $R^4$ or $L^1$ and either of $R^3$ and $R^4$ is optionally substituted with one or two groups independently selected from the group consisting of oxo, hydroxy, —O$R^6$, $C_1$-$C_4$ alkyl, halo, $C_1$-$C_4$ haloalkyl, —$C_1$-$C_3$ alkylalcohol, —C(O)$C_1$-$C_3$ alkyl, $C_3$-$C_6$ cycloalkyl, N$R^6R^{6'}$, and $C_1$-$C_4$ alkylN$R^6R^{6'}$;
$R^5$ is hydrogen, halo, cyano, methyl, and methoxy;
$R^6$ and $R^{6'}$ are independently selected from the group consisting of hydrogen, $C_1$-$C_4$ alkyl, —$C_1$-$C_3$ alkylalcohol, —$C_1$-$C_3$ haloalkyl, and $C_3$-$C_4$ cycloalkyl, or $R^6$ and $R^{6'}$ combine together with the nitrogen atom to which they are attached to form a 4 to 6 member nitrogen containing heterocyclic ring optionally substituted with a group selected from halo, $C_1$-$C_2$ alkyl, and hydroxy;
or a pharmaceutically acceptable salt, or enantiomer, diastereomer or mixture of diastereomers thereof.

2. A compound according to claim 1 wherein:
$R^1$ is chloro, methoxy, fluoro, trifluoromethyl, or cyclopropoxy;
$R^a$ and $R^b$ are independently hydrogen, fluoro, or methoxy;
$R^2$ is hydrogen;
$L^1$ is selected from the group consisting of a bond, —C(O)CH$_2$CH$_2$—, —NHC(O)CH$_2$CH$_2$—, —NHC(O)CH$_2$CH$_2$CH$_2$—, —C(O)NHCH$_2$CH$_2$—, and —C(O)NHCH$_2$CH$_2$CH$_2$—;
$R^3$ and $R^4$ combine together and with the nitrogen atom to which they are attached form an optionally substituted 4 to 7 member nitrogen containing heterocyclic ring; or one of $R^3$ and $R^4$ combine with $L^1$ at a position α, β, or γ to the nitrogen of N$R^3R^4$ to form a 4 to 7 member nitrogen containing heterocyclic ring with $L^1$; wherein each 4 to 7-member nitrogen containing heterocyclic ring formed by $R^3$ and $R^4$ or $L^1$ and either of $R^3$ and $R^4$ is selected from azetidinyl, pyrrolidinyl, morpholino, piperidinyl, piperazinyl, and diazepanyl, and wherein each 4 to 7 member nitrogen containing heterocyclic ring is optionally substituted with one or two groups independently selected from the group consisting of OH, OC$_1$-$C_3$ alkyl, OC$_1$-$C_2$ haloalkyl, NHC$_1$-$C_2$ alkylalcohol, NH$_2$, NHCH$_3$, N(CH$_3$)$_2$, NHcyclopropyl, N(cyclopropyl)$_2$, amino-substituted pyrrolidinyl, fluoro-substituted pyrrolidinyl, C(O)CH$_3$, and NHC$_2$-$C_3$ haloalkyl; and
$R^5$ is hydrogen or methyl.

3. A compound according to claim 1 wherein:
$R^1$ is chloro, methoxy, fluoro, trifluoromethyl, or cyclopropoxy;
$R^a$ and $R^b$ are independently hydrogen, fluoro, or methoxy;
$R^2$ is hydrogen;
$L^1$ is a bond;
$R^3$ and $R^4$ combine together and with the nitrogen atom to which they are attached to form a 4 to 7 member nitrogen containing heterocyclic ring selected from the group consisting of pyrrolidinyl, morpholino, piperidinyl, and piperazinyl, each optionally substituted with one or two groups independently selected from the group consisting of OH, fluoro, OC$_1$-$C_3$ alkyl, OC$_1$-$C_2$ haloalkyl, NHC$_1$-$C_2$ alkylalcohol, NH$_2$, NHCH$_3$, N(CH$_3$)$_2$, NHcyclopropyl, N(cyclopropyl)$_2$, fluoro-substituted pyrrolidinyl, C(O)CH$_3$, and NHC$_2$-$C_3$ haloalkyl;
$R^5$ is hydrogen or methyl.

4. A compound according to claim 1 wherein:
$R^1$ is chloro, methoxy, fluoro, trifluoromethyl, or cyclopropoxy;
$R^a$ and $R^b$ are independently hydrogen fluoro or methoxy
$R^2$ is hydrogen;
$L^1$ is selected from the group consisting of a bond, —C(O)CH$_2$CH$_2$—, —NHC(O)CH$_2$CH$_2$—, —NHC(O)CH$_2$CH$_2$CH$_2$—, —C(O)NHCH$_2$CH$_2$—, and —C(O)NHCH$_2$CH$_2$CH$_2$—.
$R^3$ and $R^4$ combine together and with the nitrogen atom to which they are attached form an optionally substituted 4 to 7 member nitrogen containing heterocyclic ring; or one of $R^3$ and $R^4$ combine with $L^1$ at a position α, β, or γ to the nitrogen of N$R^3R^4$ to form a 4 to 6 member nitrogen containing heterocyclic ring with $L^1$; wherein each 4 to 7-member nitrogen containing heterocyclic ring formed by $R^3$ and $R^4$ or $L^1$ and either of $R^3$ and $R^4$ is selected from azetidinyl, pyrrolidinyl, morpholino, piperidinyl, piperazinyl, and diazepanyl, each 4 to 7 member nitrogen containing heterocyclic ring is optionally substituted with one or two groups independently selected from the group consisting of OH, fluoro, $OC_1$-$C_3$ alkyl, $OC_1$-$C_2$ haloalkyl, $NHC_1$-$C_2$ alkylalcohol, $NH_2$, $NHCH_3$, $N(CH_3)_2$, NHcyclopropyl, N(cyclopropyl)$_2$, amino-substituted pyrrolidinyl, fluoro-substituted pyrrolidinyl, $C(O)CH_3$, and $NHC_2$-$C_3$ haloalkyl; and $R^5$ is hydrogen or methyl.

5. A compound according to claim 1 wherein:

$R^1$ is chloro, methoxy, fluoro, trifluoromethyl, trifluoromethoxy, or cyclopropoxy;

$R^a$ and $R^b$ are independently hydrogen, fluoro, or methoxy;

$R^2$ is hydrogen;

$L^1$ is selected from the group consisting of a bond, —$OCH_2CH_2$—, —$OCH_2CH_2CH_2$—, —$NHC(O)CH_2$—, —$NHC(O)CH_2CH_2$—, —$C(O)NHCH_2CH_2$, and —$C(O)NHCH_2CH_2CH_2$—;

$R^3$ and $R^4$ combine together and with the nitrogen atom to which they are attached form an optionally substituted 4 to 7 member nitrogen containing heterocyclic ring; or one of $R^3$ and $R^4$ combine with $L^1$ at a position α, β, γ to the nitrogen of $NR^3R^4$ to form a 4 to 6 member nitrogen containing heterocyclic ring with $L^1$; wherein each 4 to 7-member wherein each 4 to 7 member nitrogen containing heterocyclic ring formed by $R^3$ and $R^4$ or $L^1$ and either of $R^3$ and $R^4$ is selected from pyrrolidinyl, morpholino, piperidinyl, and piperazinyl, and wherein each 4 to 7 member nitrogen containing heterocyclic ring is optionally substituted with one or two groups independently selected from the group consisting of OH, fluoro, $OC_1$-$C_3$ alkyl, $OC_1$-$C_2$ haloalkyl, $NHC_1$-$C_2$ alkylalcohol, $NH_2$, $NHCH_3$, $N(CH_3)_2$, NHcyclopropyl, N(cyclopropyl)$_2$, amino-substituted pyrrolidinyl, fluoro-substituted pyrrolidinyl, $C(O)CH_3$, and $NHC_2$-$C_3$ haloalkyl;

$R^5$ is hydrogen.

6. A compound according to claim 1 wherein:

$R^1$ is chloro, methoxy, fluoro, trifluoromethyl, or cyclopropoxy;

$R^a$ and $R^b$ are independently hydrogen, fluoro, or methoxy;

$R^2$ is hydrogen;

$L^1$ is a bond;

$R^3$ and $R^4$ combine with each other and with the nitrogen atom to which they are attached to form a 4 to 7 member heterocyclic ring selected from pyrrolidinyl, morpholino, piperidinyl, and piperazinyl, each optionally substituted with one or two groups independently selected from OH, fluoro, $OC_1$-$C_3$ alkyl, $OC_1$-$C_2$ haloalkyl, $NHC_1$-$C_2$ alkylalcohol, $NH_2$, $NHCH_3$, $N(CH_3)_2$, NHcyclopropyl, N(cyclopropyl)$_2$, amino-substituted pyrrolidinyl, fluoro-substituted pyrrolidinyl, $C(O)CH_3$, $NR^6R^{6'}$, $NHCH_2CHF_2$, and $NHCH_2CH_2F$;

$R^6$ and $R^{6'}$ are independently hydrogen, methyl, ethyl, 2-fluoroethyl, 2,2-difluoroethyl, cyclopropyl, cyclobutyl, or $R^6$ and $R^{6'}$ combine to form a 4 to 6 member nitrogen containing heterocyclic ring optionally substituted with a group selected from hydroxy, fluoro, and methyl.

7. A compound according to claim 1 wherein:

$R^1$ is chloro, methoxy, fluoro, trifluoromethyl, or cyclopropoxy;

$R^a$ and $R^b$ are independently hydrogen, fluoro, or methoxy;

$R^2$ is hydrogen;

$L^1$ is $OCH_2CH_2$—, —$NHC(O)CH_2$—, —$NHC(O)CH_2CH_2$—, or —$C(O)NHCH_2CH_2$—;

$R^3$ and $R^4$ combine with each other to form a 4 or 7 member heterocyclic ring selected from pyrrolidinyl, morpholino, piperidinyl, and piperazinyl wherein each 4 to 7 member nitrogen containing heterocyclic ring is optionally substituted with one or two groups independently selected from OH, $NR^6R^{6'}$, halo, $C_1$-$C_3$ alkyl and $C_1$-$C_3$ haloalkyl;

$R^5$ is hydrogen;

$R^6$ and $R^{6'}$ are independently hydrogen, methyl, ethyl, 2-fluoroethyl, 2,2-difluoroethyl, cyclopropyl, cyclobutyl, or $R^6$ and $R^{6'}$ combine to form a 4 to 6 member heterocyclic ring optionally substituted with a group selected from hydroxy, fluoro, and methyl.

8. A compound according to claim 1 wherein:

$R^1$ chloro, methoxy, fluoro, trifluoromethyl, or cyclopropoxy;

$R^a$ and $R^b$ are independently hydrogen, fluoro, or methoxy;

$R^2$ is hydrogen;

$L^1$ is a bond;

$R^3$ and $R^4$ combine with each other to form a 4 to 7 member nitrogen containing heterocyclic ring selected from pyrrolidinyl, morpholino, piperidinyl, and piperazinyl wherein each nitrogen containing heterocyclic ring is optionally substituted with one or two groups independently selected from OH, $NR^6R^{6'}$, halo, $C_1$-$C_3$ alkyl and $C_1$-$C_3$ haloalkyl;

$R^5$ is hydrogen or methyl;

$R^6$ and $R^{6'}$ are independently hydrogen, $CH_2CHF_2$, methyl, cyclopropyl or cyclobutyl.

9. A compound according to claim 1 wherein:

$R^1$ is chloro, methoxy, fluoro, trifluoromethyl, or cyclopropoxy;

$R^a$ and $R^b$ are independently hydrogen, fluoro, or methoxy;

$R^2$ is hydrogen;

$L^1$ is $OCH_2CH_2$—, or —$OCH_2CH_2CH_2$—;

$R^3$ and $R^4$ combine with each other to form a 4 or 7 member heterocyclic ring selected from pyrrolidinyl, morpholino, piperidinyl, diazepanyl, and piperazinyl wherein each 4 to 7 member nitrogen containing heterocyclic ring is optionally substituted with one or two groups independently selected from OH, $NR^6R^{6'}$, halo, $C_1$-$C_3$ alkyl and $C_1$-$C_3$ haloalkyl;

$R^5$ is hydrogen;

$R^6$ and $R^{6'}$ are independently hydrogen, methyl, ethyl, 2-fluoroethyl, 2,2-difluoroethyl, cyclopropyl, cyclobutyl, or $R^6$ and $R^{6'}$ combine to form a 4 to 6 member heterocyclic ring optionally substituted with a group selected from hydroxy, fluoro, and methyl.

10. A compound according to claim 1 wherein:

$R^1$ is chloro, methoxy, fluoro, trifluoromethyl, or cyclopropoxy;

$R^a$ and $R^b$ are independently hydrogen, fluoro, or methoxy;

$R^2$ is hydrogen;

$L^1$ is —$NHC(O)CH_2$—, —$NHC(O)CH_2CH_2$—, or —$C(O)NHCH_2CH_2$—;

$R^3$ and $R^4$ combine with each other to form a 4 or 7 member heterocyclic ring selected from pyrrolidinyl, morpholino, piperidinyl, and piperazinyl wherein each 4 to 7 member nitrogen containing heterocyclic ring is optionally substituted with one or two groups independently selected from OH, $NR^6R^{6'}$, halo, $C_1$-$C_3$ alkyl and $C_1$-$C_3$ haloalkyl;

$R^5$ is hydrogen;

$R^6$ and $R^{6'}$ are independently hydrogen, methyl, ethyl, 2-fluoroethyl, 2,2-difluoroethyl, cyclopropyl, cyclobutyl, or R⁶ and R⁶' combine to form a 4 to 6 member heterocyclic ring optionally substituted with a group selected from hydroxy, fluoro, and methyl.

11. A compound according to claim 1 wherein:
R¹ is chloro, fluoro, trifluoromethyl, or cyclopropoxy;
Rᵃ and Rᵇ are independently hydrogen, fluoro, or methoxy;
R² is hydrogen;
L¹ is selected from the group consisting of a bond, —OCH₂CH₂—, —NHC(O)CH₂—, —NHC(O)CH₂CH₂—, and —C(O)NHCH₂CH₂—;
R³ and R⁴ combine with each other and with the nitrogen atom to which they are attached to form a 4 to 7 member nitrogen containing heterocyclic ring; or one of R³ and R⁴ combine with L₁ at a position α, β, γ from the nitrogen of NR³R⁴ to form a heterocyclic ring;
wherein each 4 to 7-member nitrogen containing heterocyclic ring formed by the combination of R³ and R⁴ or L¹ and either of R³ and R⁴ is selected from azetidinyl, pyrrolidinyl, morpholino, piperidinyl, and piperazinyl, and wherein each 4 to 7 member nitrogen containing heterocyclic ring is optionally substituted with one or two groups independently selected from the group consisting of methyl, fluoro, OH, OCH₃, NHCH₂CH₂F, NH₂, NHCH₃, N(CH₃)₂, NHcyclopropyl, and N(cyclopropyl)₂; and
R⁵ is hydrogen.

12. A compound selected from the group consisting of:
2-(4-Chloro-phenyl)-6-[6-((S)-3-dimethylamino-pyrrolidin-1-yl)-pyridin-3-yl]-6H-thieno[2,3-c]pyridin-7-one, hydrochloride;
2-(4-Chloro-phenyl)-6-[6-((R)-3-dimethylamino-pyrrolidin-1-yl)-5-methyl-pyridin-3-yl]-6H-thieno[2,3-c]pyridin-7-one, hydrochloride;
2-(4-Chloro-phenyl)-6-[6-((R)-3-dimethylamino-pyrrolidin-1-yl)-pyridin-3-yl]-5,6-dihydro-4H-thieno[2,3-c]pyridin-7-one, hydrochloride;
2-(4-Chloro-phenyl)-6-[6-((R)-3-dimethylamino-pyrrolidin-1-yl)-5-methyl-pyridin-3-yl]-5,6-dihydro-4H-thieno[2,3-c]pyridin-7-one, hydrochloride;
2-(4-Chloro-phenyl)-6-(4-dimethylamino-3,4,5,6-tetrahydro-2H-[1,2]bipyridinyl-5'-yl)-6H-thieno[2,3-c]pyridin-7-one, dihydrochloride;
6-{6-[(S)-3-(2,2-Difluoro-ethylamino)-pyrrolidin-1-yl]-pyridin-3-yl}-2-(4-fluoro-phenyl)-6H-thieno[2,3-c]pyridin-7-one hydrochloride;
2-(4-Chloro-phenyl)-6-{6-[(R)-3-(2,2-difluoro-ethylamino)-pyrrolidin-1-yl]-pyridin-3-yl}-6H-thieno[2,3-c]pyridin-7-one, hydrochloride;
2-(4-Chloro-phenyl)-6-[6-(4-methyl-piperazin-1-yl)-pyridin-3-yl]-6H-thieno[2,3-c]pyridin-7-one, hydrochloride;
6-[6-(R)-(3-Dimethylamino-pyrrolidin-1-yl)-2-(4-trifluoromethoxy-phenyl)-6H-thieno[2,3-c]pyridin-7-one, hydrochloride;
6-[6-(R)-(3-Dimethylamino-pyrrolidin-1-yl)-pyridin-3-yl]-2-(3-fluoro-4-methoxy-phenyl)-6H-thieno[2,3-c]pyridin-7-one, hydrochloride;
6-[6-(R)-(3-Dimethylamino-pyrrolidin-1-yl)-pyridin-3-yl]-2-(2-fluoro-4-methoxy-phenyl)-6H-thieno[2,3-c]pyridin-7-one, hydrochloride;
6-[6-(R)-(3-Dimethylamino-pyrrolidin-1-yl)-pyridin-3-yl]-2-(4-fluoro-phenyl)-6H-thieno[2,3-c]pyridin-7-one, hydrochloride;
6-[6-(3-(S)-Dimethylamino-pyrrolidin-1-yl)-pyridin-3-yl]-2-(2-fluoro-4-methoxy-phenyl)-5,6-dihydro-4H-thieno[2,3-c]pyridin-7-one, hydrochloride;
6-[6-(R)-(3-Dimethylamino-pyrrolidin-1-yl)-pyridin-3-yl]-2-(2-fluoro-4-methoxy-phenyl)-5,6-dihydro-4H-thieno[2,3-c]pyridin-7-one, hydrochloride;
6-[6-(S)-(3-Dimethylamino-pyrrolidin-1-yl)-pyridin-3-yl]-2-(4-trifluoromethoxy-phenyl)-5,6-dihydro-4H-thieno[2,3-c]pyridin-7-one, hydrochloride;
6-[6-(R)-(3-Dimethylamino-pyrrolidin-1-yl)-pyridin-3-yl]-2-(4-trifluoromethoxy-phenyl)-5,6-dihydro-4H-thieno[2,3-c]pyridin-7-one, hydrochloride;
6-[6-(S)-(3-Dimethylamino-pyrrolidin-1-yl)-pyridin-3-yl]-2-(4-methoxy-phenyl)-5,6-dihydro-4H-thieno[2,3-c]pyridin-7-one, hydrochloride;
6-[6-(R)-(3-Dimethylamino-pyrrolidin-1-yl)-pyridin-3-yl]-2-(4-methoxy-phenyl)-5,6-dihydro-4H-thieno[2,3-c]pyridin-7-one, hydrochloride;
6-[6-(S)-(3-Dimethylamino-pyrrolidin-1-yl)-pyridin-3-yl]-2-(4-trifluoromethyl-phenyl)-5,6-dihydro-4H-thieno[2,3-c]pyridin-7-one, hydrochloride;
6-[6-(R)-(3-Dimethylamino-pyrrolidin-1-yl)-pyridin-3-yl]-2-(4-trifluoromethyl-phenyl)-5,6-dihydro-4H-thieno[2,3-c]pyridin-7-one, hydrochloride;
6-[6-(S)-(3-Dimethylamino-pyrrolidin-1-yl)-pyridin-3-yl]-2-(3-fluoro-4-methoxy-phenyl)-5,6-dihydro-4H-thieno[2,3-c]pyridin-7-one, hydrochloride;
6-[6-(R)-(3-Dimethylamino-pyrrolidin-1-yl)-pyridin-3-yl]-2-(3-fluoro-4-methoxy-phenyl)-5,6-dihydro-4H-thieno[2,3-c]pyridin-7-one, hydrochloride;
2-(4-Cyclopropoxy-phenyl)-6-[6-(S)-(3-dimethylamino-pyrrolidin-1-yl)-pyridin-3-yl]-5,6-dihydro-4H-thieno[2,3-c]pyridin-7-one, hydrochloride;
6-[6-(S)-(3-Dimethylamino-pyrrolidin-1-yl)-pyridin-3-yl]-2-(4-fluoro-phenyl)-5,6-dihydro-4H-thieno[2,3-c]pyridin-7-one, hydrochloride;
6-[6-(R)-(3-Dimethylamino-pyrrolidin-1-yl)-pyridin-3-yl]-2-(4-fluoro-phenyl)-5,6-dihydro-4H-thieno[2,3-c]pyridin-7-one, hydrochloride;
2-(3,4-Difluoro-phenyl)-6-[6-(R)-(3-dimethylamino-pyrrolidin-1-yl)-pyridin-3-yl]-6H-thieno[2,3-c]pyridin-7-one, hydrochloride;
2-(4-Cyclopropoxy-phenyl)-6-[6-(S)-(3-dimethylamino-pyrrolidin-1-yl)-pyridin-3-yl]-6H-thieno[2,3-c]pyridin-7-one, hydrochloride;
2-(4-Cyclopropoxy-phenyl)-6-[6-(R)-(3-dimethylamino-pyrrolidin-1-yl)-pyridin-3-yl]-6H-thieno[2,3-c]pyridin-7-one, hydrochloride 2-(2,4-Difluoro-phenyl)-6-[6-(S)-(3-dimethylamino-pyrrolidin-1-yl)-pyridin-3-yl]-6H-thieno[2,3-c]pyridin-7-one, dihydrochloride;
2-(2,4-Difluoro-phenyl)-6-[6-(R)-(3-dimethylamino-pyrrolidin-1-yl)-pyridin-3-yl]-6H-thieno[2,3-c]pyridin-7-one, dihydrochloride;
(±)-trans-2-(4-Chloro-phenyl)-6-[6-(3-dimethylamino-4-hydroxy-pyrrolidin-1-yl)-pyridin-3-yl]-6H-thieno[2,3-c]pyridin-7-one, hydrochloride;
2-(4-Chloro-phenyl)-6-[6-((R)-3-dimethylamino-pyrrolidin-1-yl)-pyridin-3-yl]-6H-thieno[2,3-c]pyridin-7-one, hydrochloride;
2-(4-Chloro-phenyl)-6-[6-((R)-pyrrolidin-3-yloxy)-pyridin-3-yl]-6H-thieno[2,3-c]pyridin-7-one, hydrochloride;
2-(4-Chloro-phenyl)-6-[6-(S)-3-methylamino-pyrrolidin-1-yl)-pyridin-3-yl]-6H-thieno[2,3-c]pyridin-7-one, hydrochloride;

2-(4-Chloro-phenyl)-6-[6-((R)-3-methylamino-pyrrolidin-1-yl)-pyridin-3-yl]-6H-thieno[2,3-c]pyridin-7-one, hydrochloride;

6-[6-((R)-3-Amino-pyrrolidin-1-yl)-pyridin-3-yl]-2-(4-chloro-phenyl)-6H-thieno[2,3-c]pyridin-7-one, hydrochloride;

2-(4-Chloro-phenyl)-6-[6-((R)-3-methylamino-pyrrolidin-1-yl)-pyridin-3-yl]-5,6-dihydro-4H-thieno[2,3-c]pyridin-7-one, hydrochloride;

2-(4-Chloro-phenyl)-6-[6-(R)-3-cyclopropylamino-pyrrolidin-1-yl)-pyridin-3-yl]-5,6-dihydro-4H-thieno[2,3-c]pyridin-7-one, hydrochloride; and (±)-cis-2-(4-Chloro-phenyl)-6-[6-(3-fluoro-4-methylamino-pyrrolidin-1-yl)-pyridin-3-yl]-5,6-dihydro-4H-thieno[2,3-c]pyridin-7-one, hydrochloride.

13. The Compound 2-(4-Chloro-phenyl)-6-[6-((R)-3-dimethylamino-pyrrolidin-1-yl)-pyridin-3-yl]-6H-thieno[2,3-c]pyridin-7-one, hydrochloride

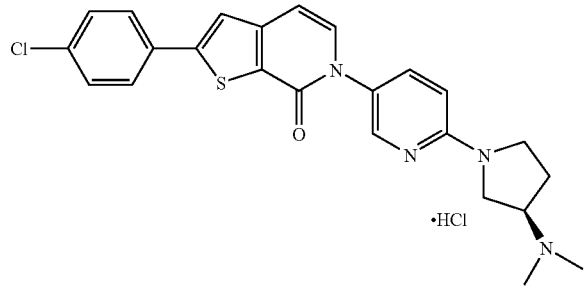

14. A pharmaceutical composition comprising a compound according to claim 1 and a pharmaceutically acceptable carrier and/or diluent.

* * * * *

UNITED STATES PATENT AND TRADEMARK OFFICE
CERTIFICATE OF CORRECTION

| | | |
|---|---|---|
| PATENT NO. | : 8,101,764 B2 | Page 1 of 1 |
| APPLICATION NO. | : 12/296557 | |
| DATED | : January 24, 2012 | |
| INVENTOR(S) | : Albert Kudzovi Amegadzie et al. | |

It is certified that error appears in the above-identified patent and that said Letters Patent is hereby corrected as shown below:

In the issued patent, please note the following corrections:

First page, Column 2 (Abstract), lines 4-5, delete "diasteromers" and insert --diastereomers--, thereof.

In Column 55, line 38, Claim 1, delete "$CH_2CH_2$" and insert --$CH_2CH_2$—;--, therefor.

In Column 55, line 39, Claim 1, delete "—$R^3$" and insert --$R^3$--, therefor.

In Column 56, line 56, Claim 4, delete "methoxy" and insert --methoxy;--, therefor.

In Column 56, line 61, Claim 4, delete "$CH_2CH_2$—." and insert --$CH_2CH_2$—;--, therefor.

In Column 57, line 26, Claim 5, delete "β, γ" and insert --β, or γ--, therefor.

In Column 58, line 17, Claim 8, delete "$R^1$" and insert --$R^1$ is--, therefor.

In Column 59, line 15, Claim 11, delete "$L_1$" and insert --$L^1$--, therefor.

In Column 59, line 15, Claim 11, delete "β, γ" and insert --β, or γ--, therefor.

In Column 59, line 42, Claim 12, delete "[1,2]" and insert --[1,2']--, therefor.

In Column 59, line 46, Claim 12, delete "7-one" and insert --7-one,--, therefor.

In Column 60, line 48, Claim 12, delete "hydrochloride" and insert --hydrochloride;--, therefor.

In Column 60, lines 48-50, Claim 12, delete "2-(2,4-Difluoro-phenyl)-6-[6-(S)-(3-dimethylamino-pyrrolidin-1-yl)-pyridin-3-yl]-6H-thieno[2,3-c]pyridin-7-one, dihydrochloride;" and insert the same on Column 60, line 49 as a new paragraph.

Signed and Sealed this
Third Day of April, 2012

David J. Kappos
*Director of the United States Patent and Trademark Office*